(12) United States Patent
Deng et al.

(10) Patent No.: US 9,573,119 B2
(45) Date of Patent: *Feb. 21, 2017

(54) PROCESS FOR PREPARING V—TI—P CATALYSTS FOR SYNTHESIS OF 2,3-UNSATURATED CARBOXYLIC ACIDS

(71) Applicant: EASTMAN CHEMICAL COMPANY, Kingsport, TN (US)

(72) Inventors: Liu Deng, Kingsport, TN (US); David William Norman, Kingsport, TN (US); Gerald Charles Tustin, Kingsport, TN (US); Bharat Venkata Boppana, Johnson City, TN (US); Melissa Page Steffey, Nickelsville, VA (US)

(73) Assignee: EASTMAN CHEMICAL COMPANY, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/859,751

(22) Filed: Sep. 21, 2015

(65) Prior Publication Data
US 2016/0009626 A1    Jan. 14, 2016

Related U.S. Application Data

(63) Continuation-in-part of application No. 14/626,111, filed on Feb. 19, 2015, now Pat. No. 9,493,390, which
(Continued)

(51) Int. Cl.
*C07C 51/377* (2006.01)
*B01J 27/198* (2006.01)
(Continued)

(52) U.S. Cl.
CPC .............. *B01J 27/198* (2013.01); *B01J 21/063* (2013.01); *B01J 35/002* (2013.01); *B01J 37/031* (2013.01); *C07C 51/09* (2013.01); *B01J 2523/00* (2013.01)

(58) Field of Classification Search
None
See application file for complete search history.

(56) References Cited

U.S. PATENT DOCUMENTS 3,086,026 A    4/1963   Wiebusch
3,226,337 A    12/1965  Riemenschneider et al.
(Continued)

FOREIGN PATENT DOCUMENTS

CN    1106315 A    8/1995
CN    1121441 A    5/1996
(Continued)

OTHER PUBLICATIONS

Ai, Applied Catalysis, 54 (1989) 29-36.*
(Continued)

*Primary Examiner* — Karl J Puttlitz
(74) *Attorney, Agent, or Firm* — Steven A. Owen

(57) ABSTRACT

The invention relates to a catalyst composition comprising a mixed oxide of vanadium, titanium, and phosphorus. The titanium component is derived from a water-soluble, redox-active organo-titanium compound. The catalyst composition is highly effective at facilitating the vapor-phase condensation of formaldehyde with acetic acid to generate acrylic acid, particularly using an industrially relevant aqueous liquid feed. Additionally, the catalyst composition is catalytically active towards the formation of acrylic acid from methylene diacetate and methacrylic acid from methylene dipropionate; both reactions are carried out with high space time yields.

17 Claims, 6 Drawing Sheets

Related U.S. Application Data is a continuation of application No. 13/826,180, filed on Mar. 14, 2013, now Pat. No. 8,993,801, which is a continuation-in-part of application No. 13/234,313, filed on Sep. 16, 2011, now Pat. No. 8,765,629.

(51) Int. Cl.

| | | |
|---|---|---|
| B01J 37/03 | (2006.01) | |
| B01J 21/06 | (2006.01) | |
| B01J 35/00 | (2006.01) | |
| C07C 51/09 | (2006.01) | |

(56) References Cited

U.S. PATENT DOCUMENTS

| | | |
|---|---|---|
| 3,657,331 A | 4/1972 | Ackermann et al. |
| 3,684,741 A | 8/1972 | Friedrichsen et al. |
| 3,894,971 A | 7/1975 | Reuter et al. |
| 3,926,846 A | 12/1975 | Ono et al. |
| 3,933,888 A | 1/1976 | Schlaefer |
| 4,040,913 A | 8/1977 | Clovis et al. |
| 4,085,143 A | 4/1978 | Holmes |
| 4,092,332 A | 5/1978 | Freerks et al. |
| 4,151,116 A | 4/1979 | McDermott |
| 4,165,438 A | 8/1979 | Schneider |
| 4,177,161 A | 12/1979 | Umemura et al. |
| 4,276,197 A | 6/1981 | Vartuli et al. |
| 4,312,787 A | 1/1982 | Dolhyj et al. |
| 4,333,858 A | 6/1982 | Decker et al. |
| 4,339,598 A | 7/1982 | Guttmann et al. |
| 4,382,876 A | 5/1983 | Neubold et al. |
| 4,447,638 A | 5/1984 | Gaffney et al. |
| 4,490,476 A | 12/1984 | Piccolini et al. |
| 4,515,904 A | 5/1985 | Edwards |
| 4,581,471 A | 4/1986 | Barlow et al. |
| 4,599,144 A | 7/1986 | Baleiko et al. |
| 4,677,225 A | 6/1987 | Niizuma et al. |
| 4,736,062 A | 4/1988 | Hagen et al. |
| 4,743,706 A | 5/1988 | Guttmann et al. |
| 4,784,981 A | 11/1988 | Alpers et al. |
| 4,801,571 A | 1/1989 | Montag et al. |
| 4,942,258 A | 7/1990 | Smith |
| 4,943,659 A | 7/1990 | Hagen |
| 4,973,569 A | 11/1990 | Bowman et al. |
| 4,990,662 A | 2/1991 | Hagen et al. |
| 5,039,644 A | 8/1991 | Lachman et al. |
| 5,169,820 A | 12/1992 | Ueda et al. |
| 5,241,114 A | 8/1993 | Smith et al. |
| 5,496,787 A | 3/1996 | Hatano et al. |
| 5,506,187 A | 4/1996 | Haddad et al. |
| 5,710,328 A | 1/1998 | Spivey et al. |
| 5,792,722 A | 8/1998 | Haddad et al. |
| 5,808,148 A | 9/1998 | Gogate et al. |
| 5,877,330 A | 3/1999 | Kishimoto et al. |
| 5,932,746 A | 8/1999 | Herron et al. |
| 5,998,657 A | 12/1999 | Gogate et al. |
| 6,265,618 B1 | 7/2001 | Zoeller et al. |
| 6,329,549 B1 | 12/2001 | Waller et al. |
| 6,429,332 B1 | 8/2002 | Tanimoto et al. |
| 6,525,216 B1 | 2/2003 | Nishimura et al. |
| 6,652,823 B2 | 11/2003 | Teunissen |
| 6,670,501 B1 | 12/2003 | Harrison et al. |
| 6,812,351 B2 | 11/2004 | Weiguny et al. |
| 6,858,561 B2 | 2/2005 | Bortinger et al. |
| 6,903,047 B2 | 6/2005 | Kourtakis et al. |
| 6,956,004 B2 | 10/2005 | Albonetti et al. |
| 7,015,357 B2 | 3/2006 | Yada et al. |
| 7,060,649 B2 | 6/2006 | Weiguny et al. |
| 7,157,599 B2 | 1/2007 | Goto et al. |
| 7,547,655 B2 | 6/2009 | Lan |
| 7,638,457 B2 | 12/2009 | Ghelfi et al. |
| 8,765,629 B2 | 7/2014 | Norman et al. |
| 8,883,672 B2 | 11/2014 | Norman et al. |
| 8,981,172 B2 | 3/2015 | Norman |
| 8,993,801 B2 | 3/2015 | Boppana et al. |

| | | |
|---|---|---|
| 2002/0183199 A1 | 12/2002 | Bogan, Jr. |
| 2004/0006244 A1 | 1/2004 | Manzer |
| 2004/0014990 A1 | 1/2004 | Storck et al. |
| 2004/0162217 A1 | 8/2004 | Albonetti et al. |
| 2004/0241067 A1 | 12/2004 | Oki et al. |
| 2005/0137422 A1 | 6/2005 | Hazin et al. |
| 2009/0209665 A1 | 8/2009 | Fu et al. |
| 2010/0016644 A1 | 1/2010 | Forkner |
| 2010/0069650 A1 | 3/2010 | Hibst et al. |
| 2010/0076233 A1 | 3/2010 | Cortright et al. |
| 2010/0087663 A1 | 4/2010 | Hibst et al. |
| 2010/0105926 A1 | 4/2010 | Hibst et al. |
| 2010/0105927 A1 | 4/2010 | Hibst et al. |
| 2011/0213174 A1 | 9/2011 | Dubois |
| 2012/0071687 A1 | 3/2012 | Herzog et al. |
| 2012/0071688 A1 | 3/2012 | Herzog et al. |
| 2012/0277466 A1 | 11/2012 | Nagaki et al. |
| 2012/0289743 A1 | 11/2012 | Nagaki et al. |
| 2013/0072696 A1 | 3/2013 | Norman |
| 2013/0072716 A1 | 3/2013 | Norman et al. |
| 2013/0102455 A1 | 4/2013 | Haddad et al. |
| 2013/0237724 A1 | 9/2013 | Boppana et al. |

FOREIGN PATENT DOCUMENTS

| | | |
|---|---|---|
| DE | 1294956 | 5/1969 |
| DE | 102004014932 A1 | 10/2004 |
| EP | 0147156 B1 | 8/1988 |
| EP | 2135671 A2 | 12/2009 |
| EP | 2340888 A1 | 7/2011 |
| GB | 1462724 A | 1/1977 |
| JP | 48-049736 B2 | 7/1973 |
| JP | S57-144039 A | 9/1982 |
| JP | 58-151313 | 9/1983 |
| JP | 58-188834 A | 11/1983 |
| JP | 61-229840 A | 10/1986 |
| JP | 64-066141 A | 3/1989 |
| JP | 64-068334 A | 3/1989 |
| JP | 64-068335 A | 3/1989 |
| JP | 64-068336 | 3/1989 |
| JP | 64-068337 A | 3/1989 |
| JP | 05-017392 A | 1/1993 |
| JP | 1996-259494 A | 10/1996 |
| JP | 2003-326168 | 11/2003 |
| JP | 2010-254887 A | 11/2010 |
| RO | 114084 B1 | 1/1999 |
| RO | 117512 B1 | 4/2002 |
| WO | WO 2006/072447 A1 | 7/2006 |
| WO | WO 2010-046227 A1 | 4/2010 |
| WO | WO 2012/148837 A1 | 11/2012 |
| WO | WO 2012/154396 A1 | 11/2012 |

OTHER PUBLICATIONS

Ai, Applied Catalysis, 59 (1990) 227-235.*
Ai, Proc. 9th Intern. Congress on Catalysis,1988.*
"Nitrogen" in Kirk-Othmer Encyclopedia of Chemical Technology, Published Online: May 13, 2005, Copyright © 2001 by John Wiley & Sons, Inc., pp. 1-23.*
Abon, M., et al.; "Evolution of a VPO Catalyst in n-Butane Oxidation Reaction during the Activation Time"; Journal of Catalysis; 1995; pp. 28-36; vol. 156; Academic Press, Inc.
Al, Mamoru; "Vapor-Phase Aldol Condensation of Formaldehyde with Propionic Acid on Vanadium Pentoxide—Phosphorus Pentoxide"; Applied Catalysis; 1988; pp. 221-330; vol. 36; Elsevier Science Publishers; The Netherlands Al__AC__1988.
Al, M.; "Preparation of High-Surface-Area Titanium-Vanadium Binary Pyrophosphate Catalysts"; Applied Catalysis; 1989; pp. 51-61; vol. 48; Elsevier Science Publishers; The Netherlands Al__AC__1989__48.
Al, Mamoru; "Effect of the Composition of Vanadium-Titanium Binary Phosphate on Catalytic Performance in Vapor-Phase Aldol Condensation"; Applied Catalysis; 1989; pp. 29-36; vol. 54; Elsevier Science Publishers; The Netherlands Al__AC__1989__54.

(56) References Cited

OTHER PUBLICATIONS

AI, Mamoru; "Reaction of Acetic Acid with Methanol over Vanadium-Titanium Binary Phosphate Catalysts in the Presence of Oxygen"; Applied Catalysis; 1990; pp. 227-235; vol. 59; Elsevier Science Publishers; The Netherlands AI_AC_1990_59.

AI, Mamoru; "Reaction of Propionic Acid with Methylal Over Vanadium-Silicon-Phosphorus Oxide"; Applied Catalysis; 1990; pp. 365-373; vol. 63; Elsevier Science Publishers; The Netherlands AI_AC_1990_63.

AI, Mamoru, et al.; "Production of methacrylic acid by vapor-phase aldol condensation of propionic acid with formaldehyde over silica-supported metal phosphate catalysts"; Applied Catalysis A: General; 2003; pp. 185-191; vol. 252; Elsevier AI_AC_2003.

AI, Mamoru; "Formation of methyl methacrylate by condensation of methyl propionate with formaldehyde over silica-supported cesium hydroxide catalysts"; Applied Catalysis A: General; 2005; pp. 211-215; Elsevier AI_AC_2005.

AI, Mamoru; "The Effects of the Reaction Variables on the Yields of Acrylic Acid and Methyl Acrylate in the Reaction of Acetic Acid with Methanol in the Presence of Oxygen"; Bulletin Chemical Society Japan; Jan. 1990; pp. 199-202; vol. 63, No. 1; The Chemical Society of Japan AI_BCSJ_1990_63_Effects.

AI, Mamoru; "The Production of Methacrylic Acid by the Vapor-Phase Aldol Condensation over V—Si—P Ternary Oxide Catalyst"; Bulletin Chemical Society Japan; Apr. 1990; pp. 1217-1220; vol. 63, No. 4; The Chemical Society of Japan AI_BCSJ_1990_63_Production.

AI, Mamoru; "Reaction of Methyl Propionate with Methylal over V—Si—P Ternary Oxide Catalysts"; Bulletin Chemical Society Japan; Dec. 1990; pp. 3722-3724; vol. 63, No. 12; The Chemical Society of Japan AI_BCSJ_1990_63_Reaction.

AI, Mamoru; "Formation of Acrylaldehyde by Vapor-Phase Aldol Condensation II. Phosphate Catalysts"; Bulletin Chemical Society Japan; Apr. 1991; pp. 1346-1350; vol. 64, No. 4; The Chemical Society of Japan AI_BCSJ_1991.

AI, M..; "Chapter 5. Vapor Phase Condensation Reactions Using Formaldehyde or Methanol"; Catalysis; 1996; pp. 152-198; vol. 12; The Royal Society of Chemistry AI_C_1996.

AI, Mamoru; "Formation of methyl methacrylate from methyl propionate and methanol"; Catalysis Today; 2006; pp. 398-402; vol. 111; Elsevier AI_CT_2006.

AI, Mamoru; "Vapor-Phase Aldol Condensation of Formaldehyde with Acetic Acid on $V_2O_5$—$P_2O_5$ Catalysts"; Journal of Catalysis; Apr. 1987; pp. 201-208; vol. 107; Academic Press AI_JOC_1987.

AI, Mamoru: "Vapor-Phase Reaction of Methanol with Methyl Acetate and Acetic Acid in the Presence of Oxygen"; Journal of Catalysis; Feb. 1988; pp. 194-200; vol. 112; Academic Press AI_JOC_1988_112.

AI, Mamoru; "Effects of Organic Compounds Used in Preparing V/Ti Binary Phosphate Catalysts"; Journal of Catalysis; 1988; pp. 562-566; vol. 113; Academic Press, Inc. AI_JOC_1988_113.

AI, Mamoru; "The Production of Methacrylic Acid by the Vapor-Phase Aldol Condensation of Propionic Acid with Formaldehyde"; Journal of Catalysis; 1990; pp. 293-296; vol. 124; Academic Press, Inc. AI_JOC_1990_124.

AI, Mamoru; "Comparison of catalytic properties for partial oxidation between heteropolyacids and phosphates of vanadium and iron"; Journal of Molecular Catalysis A: Chemical; 1996; pp. 3-13; vol. 114; Elsevier AI_JOMC_1996.

AI, Mamoru; "Catalytic Activity for Vapor-Phase Aldol Condensation and Acid-Base Properties of Metal-Oxide Catalysts"; New Frontiers in Catalysis; Jul. 1992; pp. 1199-1210; Elsevier Science Publishers B.V. AI_NFC_1992.

AI, Mamoru; "Vapor-Phase Aldol Condensation of Formaldehyde with Acetic Acid, Propionic Acid, and their Derivatives on $(VO)_2P_2O_7$—$TiP_2O_7$ Catalysts"; Proc. $9^{th}$ Intern. Congress on Catalysis; 1988; pp. 1562-1569; Canada, Ottawa AI_P9ICC_1988.

AI, Mamoru; "Preparation of high surface area titanium-vanadium binary pyrophosphate catalysts"; Shokubai; 1988; pp. 420-423 (abstract only); vol. 30, No. 6 AI_S_1988.

AI, M.; "Reaction of Methyl Acetate with Methylal in the Presence of Oxygen"; Studies in Surface Science and Catalysis; 1992; pp. 101-108; vol. 72; Elsevier Science Publishers B. V. AI_SSSC_1992.

Bartley, Jonathan K., et al.; "Chapter 12. Vanadium Phosphate Catalysts"; Metal Oxide Catalysis; 2009; pp. 499-537; WILEY-VCH Verlag. GmbH & Co. KgaA; Weinheim.

Bish, D. L. and Howard, S. A.; "Quantitative Phase Analysis Using the Rietveld Method"; Journal of Applied Crystallography; 1988; pp. 86-91; vol. 21; International Union of Crystallography.

Marcu, Ioan-Cezar, et al.; "Effects of the method of preparing titanium pyrophosphate catalyst on the structure and catalytic activity in oxidative dehydrogenation of n-butane"; Journal of Molecular Catalysis A; Chemical; Apr. 2003; pp. 241-250; vol. 203; Elsevier.

Murthy, N. S, et al., "General procedure for evaluating amorphous scattering and crystallinity from X-ray diffraction scans of semicrystalline polymers". H. Polymers; 1990; pp. 996-1002; vol. 31.

Rietveld, H. M.; "A profile refinement method for nuclear and magnetic structures"; Journal of Applied Crystallography; Jun. 1969; pp. 65-71; vol. 2, Part 2 (Abstract).

Scherrer, P.; "Bestimmung der Grösse und der inneren Struktur von Kolloidteilchen mittels Röntgenstrahlen"; Nachrichten von der Königlichen Gesellschaft der Wissenschaften zu Göttingen; Jahre 1918; pp. 98-100.

Yoshitake, Hideaki and Tatumi, Takashi; "Vandium Oxide Incorporated into Mesoporous Titania with a BET Surface Area above 1000 $m^2.g^{-1}$: Preparation, Spectroscopic Characterization and Catalytic Oxidation"; Chemistry of Materials; Feb. 2003; pp. 1695-1702; vol. 15; American Chemical Society.

Co-pending U.S. Appl. No. 13/234,313; filed Sep. 16, 2011; now U.S. Publication No. 2013-0072715; Norman et al.

Co-pending U.S. Appl. No. 13/826,180, filed Mar. 14, 2013; Boppana et al.

Co-pending U.S. Appl. No. 13/234,323, filed Sep. 16, 2011; now U.S. Publication No. 2013-0072716; Norman and King.

Co-pending U.S. Appl. No. 13/234,277, filed Sep. 16, 2011; now U.S. Publication No. 2013-0072696; Norman.

Notification of Transmittal of the International Search Report and the Written Opinion of the International Searching Authority, or the Declaration date of mailing Dec. 11, 2012 received in corresponding International Application No. PCT/US2012/053365.

Notification of Transmittal of the International Search Report and the Written Opinion of the International Searching Authority, or the Declaration date of mailing Jan. 2, 2013 received in corresponding International Application No. PCT/US2012/053359.

Notification of Transmittal of the International Search Report and the Written Opinion of the International Searching Authority, or the Declaration date of mailing Jan. 2, 2013 received in corresponding International Application No. PCT/US2012/052989.

Office Action notification date Sep. 9, 2013 received in co-pending U.S. Appl. No. 13/234,313.

Office Action notification date Nov. 1, 2013 received in co-pending U.S. Appl. No. 13/234,323.

Office Action notification date Nov. 8, 2013 received in co-pending U.S. Appl. No. 13/234,277.

Office Action notification dated Jan. 30, 2014 received in co-pending U.S. Appl. No. 13/234,313.

Notice of Allowance dated Mar. 10, 2014 received in co-pending U.S. Appl. No. 13/234,313.

Office Action dated Jun. 20, 2014 received in co-pending U.S. Appl. No. 13/234,277.

Notice of Allowance dated Jul. 14, 2014 received in co-pending U.S. Appl. No. 13/234,323.

Office Action dated Oct. 7, 2014 received in co-pending U.S. Appl. No. 13/826,180.

Otake, Masayuki; "Method for the Manufacture of Composite Oxide Catalyst"; English translation of JP S64-4817, Publication Date is Jan. 26, 1989.

Co-pending U.S. Appl. No. 14/509,517, filed Oct. 8, 2014.

Notice of Allowance dated Feb. 2, 2015 received in co-pending U.S. Appl. No. 13/826,180.

(56) References Cited

OTHER PUBLICATIONS

Notice of Allowance dated Feb. 2, 2015 received in co-pending U.S. Appl. No. 13/234,277.
Co-pending U.S. Appl. No. 14/626,111, filed Feb. 19, 2015.
Office Action dated Mar. 24, 2015 received in co-pending U.S. Appl. No. 14/626,111.
Notice of Allowance dated Sep. 28, 2015 received in co-pending U.S. Appl. No. 14/626,111.
Office Action dated Nov. 30, 2015 received in co-pending U.S. Appl. No. 14/626,111.
Tong, Xin et al.; "Photocatalytic Activity of TiOx with Micrometer-Sized Macropores"; Acta Physico-Chimica Sinica (Wuli Huaxue Xuebao), 27 (8); 2011; pp. 1941-1946 (English Abstract).
Notice of Allowance dated Jun. 22, 2016 received in co-pending U.S. Appl. No. 14/626,111.
Notice of Allowance dated Oct. 3, 2016 received in co-pending U.S. Appl. No. 14/626,111.

* cited by examiner

PROCESS FOR PREPARING V—TI—P CATALYSTS FOR SYNTHESIS OF 2,3-UNSATURATED CARBOXYLIC ACIDS

CROSS REFERENCE TO RELATED APPLICATION

This application is a continuation-in-part of U.S. Non-Provisional patent application Ser. No. 14/626,111 filed Feb. 19, 2015, which is a continuation of U.S. Non-Provisional patent application Ser. No. 13/826,180 filed Mar. 14, 2013, now U.S. Pat. No. 8,993,801, which is a continuation-in-part of U.S. Non-Provisional patent application Ser. No. 13/234,313 filed Sep. 16, 2011, now U.S. Pat. No. 8,765,629, the entireties of which are incorporated herein by reference.

FIELD OF THE INVENTION

The invention generally relates to the field of catalysis and, in particular, to mixed oxide catalysts for the preparation of 2,3-unsaturated carboxylic acids with oxygen in the diluent gas. The invention further relates to the preparation of 2,3-unsaturated carboxylic acids using a methylene dialkanoate feed with a mixed oxide catalyst with oxygen in the diluent gas.

BACKGROUND OF THE INVENTION 2,3-Unsaturated carboxylic acids and esters can be prepared from the reaction of a formaldehyde ($H_2CO$) source and a saturated carboxylic acid or ester containing one less carbon atom. Thus, acrylic and methacrylic acid derivatives can be prepared from the condensation of a formaldehyde source with acetic or propionic acid derivatives, respectively. The reaction produces one equivalent of water for each equivalent of carboxylic acid derivative reacted.

Although a number of catalysts have been proposed for this reaction, catalysts containing acidic vanadium and phosphorus oxides are among the most efficient, especially when a third component such as titanium or silicon is present in the catalyst. Water, however, tends to inhibit the condensation reaction with these catalysts. The use of formalin—which typically contains about 37 weight percent formaldehyde in water—as a starting material, therefore, is less efficient. Methanol can also be an inhibitor for the condensation reaction, and, since formalin can also contain methanol, the efficiency can be further lowered. When a carboxylic acid is the reactant, the presence of methanol in formalin can create a mixture of acids and methyl esters. And when an ester is the reactant, the water in formalin can create a mixture of acids and esters.

Industrial grade aqueous formaldehyde contains about 55 weight percent formaldehyde. It is relatively inexpensive and, therefore, is an economical source of this reactant. Thus, there is a need in the art for catalysts that are capable of condensing formaldehyde with alkanoic acids or esters in the vapor phase and that are tolerant of water in the feedstock. Ideally, such catalysts would also provide a high conversion of formaldehyde along with a high selectivity to the acrylic product.

The conventional process for these aldol condensation reactions combines a formaldehyde source, such as trioxane, with a carboxylic acid to form water, the 2,3-unsaturated carboxylic acid, and formaldehyde. The formaldehyde can react with itself at any time during the reaction to form paraformaldehyde. This by-product formation of paraformaldehyde can contribute to yield losses and increased maintenance costs as the paraformaldehyde deposits on equipment and piping.

Conventional Feed

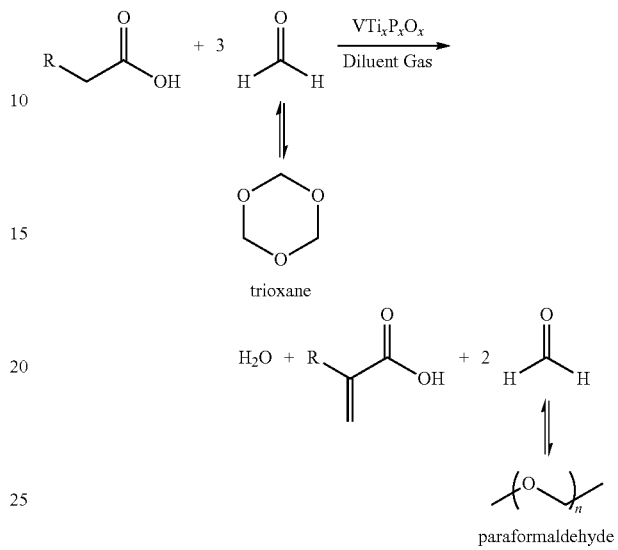

The problems caused by paraformaldehyde create the need to make 2,3-unsaturated carboxylic acids without producing significant paraformaldehyde. One solution is to introduce a methylene unit by an alternative feed that does not utilize or produce formaldehyde which can polymerize to paraformaldehyde. A methylene dialkanoate feed can be used as such an alternative feed.

Methylene Dialkanoate Feed

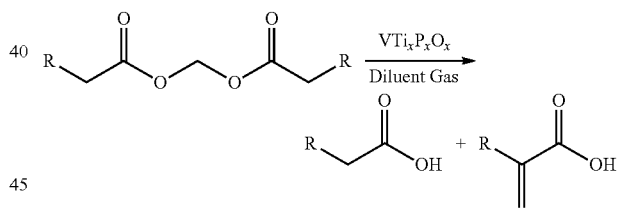

The use of a methylene dialkanoate feed can also lead to improved space time yield (STY) while operating at decreased temperatures, even in the presence of extraneous water when compared to the conventional reaction process. These reaction improvements come as a surprise since acrylic acid production from conventional feeds comprising acetic acid and formaldehyde (as trioxane) are negatively impacted by water and reduced temperature. The practical utility of these benefits are increased catalyst lifetime and maintained STY when water is introduced to the reaction system from impure gas lines or generated via by-product chemistry.

Although the V—Ti—P catalysts of the present invention function with the presence of water, improved STY can be seen by attenuating the effects of water. One approach to reduce the presence of water in the feed is to replace aqueous formaldehyde with anhydrous formaldehyde (trioxane, $C_3H_6O_3$). Despite this replacement, the molar addition of trioxane with acetic acid still includes one mole of a latent molecular water, thereby limiting the maximum attainable rate. To further offset the effect of water, methylene dialkanoates, such as methylene diacetate (MDA) and methylene dipropionate (MDP) can be synthesized from formaldehyde and utilized as a feed towards the production of acrylic acid and methacrylic acid, respectively. These methylene dialkanoates are molecularly equivalent to one mole of formaldehyde and two moles of the corresponding carboxylic acid but without the latent molecular water (i.e. one mole of latent water is not produced). MDA and MDP form acrylic acid and methacrylic acid, respectively, over the V—Ti—P catalyst at a surprisingly high reaction rate and yield.

Vanadium-titanium-phosphorus (V—Ti—P) mixed oxides are the best known catalysts for generating acrylic acid from the condensation of formaldehyde and acetic acid. But the preparation of these catalysts can be dangerous and is not amenable to scale-up. Typically, the titanium component is incorporated into these catalysts by first hydrolyzing liquid titanium chloride. This step, unfortunately, generates large quantities of hydrochloric acid fumes. Thus, there is also a need in the art for methods of preparing V—Ti—P mixed oxide catalysts that are safer and more amenable to industrial production.

The reactions catalyzed by vanadium-titanium-phosphorus catalysts usually produce few undesired side reactions and offer high yields. However, one of the drawbacks with V—Ti—P condensation catalysts is they can quickly deactivate during the reaction due to coking on the catalyst. Although the V—Ti—P catalyst can typically be regenerated by removing the coke at an elevated temperature in the presence of oxygen, the lifetime of the reactive catalyst between regenerations can be limited and short. It has been shown that co-feeding oxygen can help stabilize the condensation catalyst over a short period of time, i.e. 8 hours. However, inferior yields to acrylic acid were also observed. Thus, there is a need to extend the reactive lifetime of the V—Ti—P catalyst while maintaining the high conversion and selectivity by co-feeding oxygen at certain concentrations to the reactor.

The present invention addresses these needs as well as others that will be apparent from the following description and claims.

SUMMARY OF THE INVENTION

In a first aspect, the present invention provides a catalyst composition comprising a mixed oxide of vanadium (V), titanium (Ti), and phosphorus (P). The titanium component of the catalyst composition is derived from a water-soluble, redox-active organo-titanium compound.

In a second aspect, the present invention provides a method for preparing a catalyst composition comprising a mixed oxide of vanadium (V), titanium (Ti), and phosphorus (P). The method comprises the steps of:
(a) providing an aqueous solution comprising a water-soluble, redox-active organo-titanium compound;
(b) adding a vanadium compound and a phosphorus compound to the aqueous titanium solution to form a mixture of catalyst components;
(c) heat-treating the mixture;
(d) removing water from the heat-treated mixture to obtain a solid residue comprising the catalyst components; and
(e) calcining the solid residue at an elevated temperature in the presence of air to obtain the catalyst composition.

In a third aspect, the present invention provides a process for preparing a 2,3-unsaturated carboxylic acid. The process comprises the step of contacting a formaldehyde source with a carboxylic acid in the presence of a condensation catalyst under vapor-phase condensation conditions to obtain the 2,3-unsaturated carboxylic acid. The condensation catalyst comprises a mixed oxide of vanadium (V), titanium (Ti), and phosphorus (P). The titanium component of the condensation catalyst is derived from a water-soluble, redox-active organo-titanium compound.

In a fourth aspect, the present invention provides a process for preparing a 2,3-unsaturated carboxylic acid. The process comprises the steps of contacting a methylene dialkanoate and a diluent gas with a condensation catalyst under vapor-phase condensation conditions to obtain the 2,3-unsaturated carboxylic acid. The condensation catalyst comprises a mixed oxide of vanadium (V), titanium (Ti), and phosphorus (P). The methylene dialkanoate has the general formula (I):

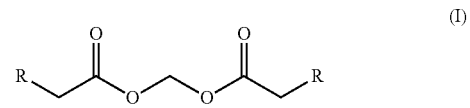

wherein R is selected from the group consisting of hydrogen and an alkyl group having 1 to 8 carbon atoms.

In a fifth aspect, the present invention provides a process for preparing a 2,3-unsaturated carboxylic acid. The process comprises the step of contacting a methylene dialkanoate and a diluent gas with a condensation catalyst under vapor-phase condensation conditions to obtain the 2,3-unsaturated carboxylic acid. The condensation catalyst comprises a mixed oxide of vanadium (V), titanium (Ti), and phosphorus (P). The titanium component is derived from a water-soluble, redox-active organo-titanium compound. The methylene dialkanoate has the general formula (I):

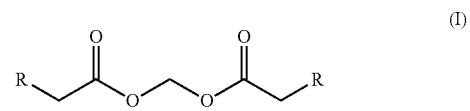

wherein R is selected from the group consisting of hydrogen, methyl, ethyl, propyl, and isopropyl.

In a sixth aspect, the present invention provides a process for preparing a 2,3-unsaturated carboxylic acid comprising: contacting a formaldehyde source, a carboxylic acid, and a diluent gas with a condensation catalyst under vapor-phase condensation conditions to obtain the 2,3-unsaturated carboxylic acid; wherein the condensation catalyst comprises a mixed oxide of vanadium (V), titanium (Ti), and phosphorus (P); wherein the diluent gas comprises from about 3 mol % to about 5 mol % oxygen, based on the total moles of feed; and wherein the process has a selectivity of greater than about 40% and a conversion of greater than about 40%.

In a seventh aspect, the present invention provides a process for preparing acrylic acid comprising: contacting a formaldehyde source, acetic acid, and a diluent gas with a condensation catalyst under vapor-phase condensation conditions to obtain the acrylic acid; wherein the condensation catalyst comprises a mixed oxide of vanadium (V), titanium (Ti), and phosphorus (P); wherein the diluent gas comprises from about 3 mol % to about 5 mol % oxygen, based on the total moles of feed; and wherein the process has a selectivity of greater than 40% and a conversion of greater than 40%.

In an eighth aspect, the present invention provides a process for preparing methacrylic acid comprising: contacting a formaldehyde source, propionic acid, and a diluent gas with a condensation catalyst under vapor-phase condensation conditions to obtain the methacrylic acid; wherein the condensation catalyst comprises a mixed oxide of vanadium (V), titanium (Ti), and phosphorus (P); wherein the diluent gas comprises from about 3 mol % to about 5 mol % oxygen, based on the total moles of feed; and wherein the process has a selectivity of greater than 40% and a conversion of greater than 40%.

DETAILED DESCRIPTION OF THE INVENTION

Figure 1:
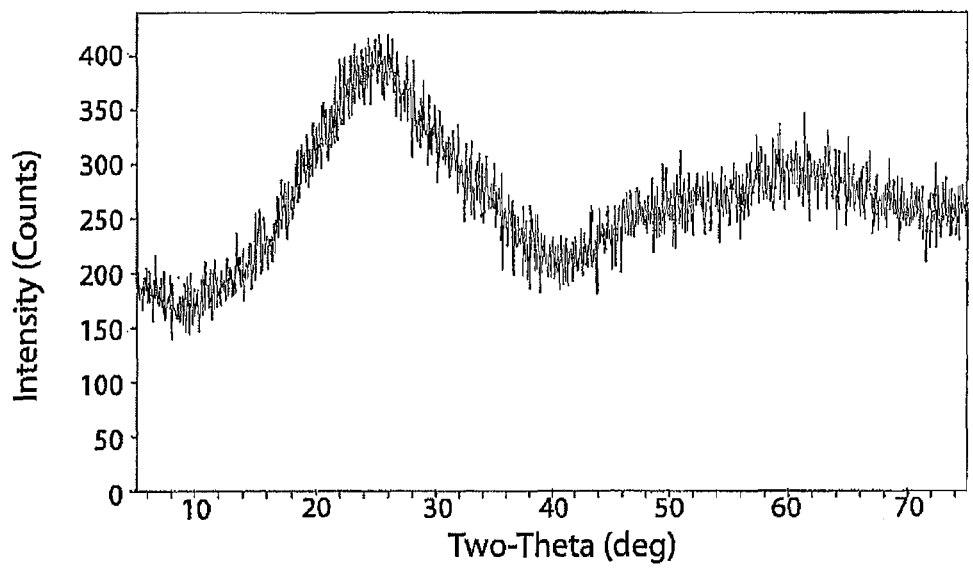
FIG. 1 is a graph showing the X-ray diffraction pattern of the amorphous catalyst prepared via Method A in Example 1.

It has been surprisingly discovered that V—Ti—P mixed oxide catalysts can be prepared from a water-soluble, redox-active organo-titanium source. Employing such a titanium source can provide an inherently safer, and more practical and rapid route to V—Ti—P materials. In addition, it has been surprisingly discovered that the resulting catalysts can have a higher surface area and acidity, and can be more active for acrylic acid formation when an aqueous formaldehyde source and acetic acid are used as the feed. Moreover, it has been surprisingly discovered that the resulting catalyst can be even more active for the formation of acrylic acid and methacrylic acid from MDA and MDP, respectively.

Thus, in a first aspect, the present invention provides a catalyst composition comprising a mixed oxide of vanadium (V), titanium (Ti), and phosphorus (P). The titanium component of the catalyst composition is derived from a water-soluble, redox-active organo-titanium compound (sometimes referred to herein as simply "water-soluble titanium compound," "organo-titanium compound," or "titanium compound").

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

By "water-soluble," it is meant that the organo-titanium compound can dissolve in water at 20° C. and 1 atm absolute (101.325 kPa) to form a homogeneous solution of at least 1 weight percent of the organo-titanium compound. Preferably, the compound can dissolve in water to form a homogeneous solution of at least 25 weight percent. More preferably, the compound can dissolve in water to form a homogeneous solution of at least 40 weight percent.

By "redox-active," it is meant that the organic ligand of the organo-titanium compound is capable of reducing the oxidation state of vanadium from +5 to +4, +5 to +3, or +4 to +3. Alternatively, the organo-titanium compound is "redox-active" if the derivative of the organo-titanium compound, in the aqueous mixture used to make the catalyst, is capable of reducing the oxidation state of vanadium from +5 to +4, +5 to +3, or +4 to +3.

Examples of water-soluble, redox-active organo-titanium compounds include titanium lactates, titanium alkanolamines, and titanium acetylacetonates. Such compounds are commercially available, such as from Dorf Ketal under the trade name TYZOR®. Practical examples of such compounds include titanium(IV) bis(ammonium lactate)dihydroxide (TBALDH), titanium diethanolamine, titanium triethanolamine, and titanium acetylacetonate. In one aspect, the organo-titanium compound comprises titanium(IV) bis(ammonium lactate)dihydroxide.

The catalyst composition according to the present invention can have the general formula $VTi_aP_bO_c$, wherein a=0.3 to 6.0, preferably 1.0 to 4.0; b=2.0 to 13.0, preferably 4.0 to 10.0; and c is the number of atoms required to satisfy the valences of the components other than oxygen.

The catalyst composition of the invention can be supported on an oxide support. Suitable oxide supports include silica, alumina, titanium oxide, zirconium oxide, and titanium or zirconium pyrophosphates. Other oxide supports may be used provided that they are inert to the desired catalytic reaction. The supports should be physically robust and pre-shaped. The term "pre-shaped" is used in this context to mean that the shape of the final catalyst is essentially the same as the starting support. The pre-shaped oxides typically can have average particle diameter sizes ranging from about 0.1 millimeter (mm) to about 20 mm. They can be in any common form such as extrudates, compressed pellets, or bulk solid that has been pulverized to the desired mesh size. They may also be in a variety of shapes such as rods, stars, cylinders, spheres, or broken chunks.

The catalyst composition according to the present invention can be primarily amorphous in structure. One skilled in the art recognizes that an amorphous catalyst composition can have a small amount of crystalline structure caused, for example, by impurities. By "amorphous" or "primarily amorphous" it is meant that the catalyst composition contains less than 10 weight percent crystalline material. The percent crystallinity is calculated based on the integrated intensities of an X-Ray diffraction from the individual diffraction patterns with peaks of crystallite size greater than 30 Å defined as crystalline and peaks of crystallite size less than or equal to 30 Å defined as amorphous.

In accordance with a second aspect of the invention, the catalyst composition according to the present invention can be prepared using the following general steps:
(f) providing an aqueous solution comprising the water-soluble, redox-active organo-titanium compound;
(g) adding a vanadium compound and a phosphorus compound to the aqueous titanium solution to form a mixture of catalyst components;
(h) heat-treating the mixture;
(i) removing water from the heat-treated mixture to obtain a solid residue comprising the catalyst components; and
(j) calcining the solid residue at an elevated temperature in the presence of air to obtain the catalyst composition.

The aqueous solution containing the water-soluble titanium compound may be obtained directly from commercial sources or may be made by dissolving the titanium compound in water. The concentration of the aqueous titanium solution can vary over a wide range. For example, the solution can have a titanium compound concentration in the range of 25 to 75 wt %, or 30 to 70 wt %, or 50 to 60 wt %.

The mode of adding the vanadium compound and the phosphorus compound to the aqueous titanium solution is not particularly limiting. For example, the vanadium compound and the phosphorus compound may be blended together to form a physical mixture or a reaction product, before being added to the aqueous titanium solution. Alternatively, the V and P compounds may be added sequentially in any order or simultaneously to the aqueous titanium solution. Thus, as used herein, the expression "adding a vanadium compound and a phosphorus compound" can refer to the addition of the vanadium compound and the phosphorus compound separately or collectively as a physical mixture or as a reaction product of the two.

Similarly, the heat-treating step and the water-removing step may be conducted sequentially or simultaneously. For example, in the case of water removal by distillation or evaporation, the heat-treating step can take place during the distillation or evaporation.

The heat-treating step may be conducted over a wide temperature range, such as from above ambient up to 200° C. or higher. The purpose of the heat-treating step is to facilitate mixing and/or reaction among the catalyst precursors. Depending on the catalyst precursors and the temperature employed, the heat-treating step may be carried out from several minutes to hours or days.

The water-removal step may be accomplished in a number of ways. For example, as mentioned above, water may be removed by distillation or evaporation. Alternatively, as discussed in more detail below, the catalyst components can be precipitated out of solution by adding an anti-solvent to the mixture to precipitate out the catalyst components and separating the precipitate from the liquid to obtain the solid residue. The water can then be removed by decanting or filtration.

Following the water-removal step, which may include a subsequent drying step, the resulting solid residue may be crushed and sieved to obtain a desired particle size. The sieved catalyst particles can then be calcined in one or more stages in air prior to use. The calcining temperature is normally in the range of 200° C. to 800° C. Preferably, the calcining temperature ranges from 300° C. to 500° C. The calcining step is typically carried out for 1 to 10 hours, and preferably for 2 to 8 hours. Upon calcining, the mixed oxide catalyst according to the invention is formed.

In addition to the water-soluble titanium compounds mentioned above, the catalyst precursors may be ammonium salts, halides, oxyacids, oxyacid salts, hydroxides, or oxides of vanadium, titanium, and phosphorus. In one aspect of the invention the catalyst composition is prepared with the organo-titanium compound comprising titanium(IV) bis(ammonium lactate)dihydroxide.

The vanadium compound is preferably water soluble. Examples of such compounds include vanadium trichloride, vanadium(IV) sulfate oxide hydrate, and ammonium vanadate optionally treated with aqueous oxalic acid and/or lactic acid. Other water-soluble vanadium sources can also be used.

The phosphorus compound is also preferably water soluble. The compound should be converted to phosphorus oxides when calcined. Such phosphorus compounds include phosphoric acid, phosphorous acid, and ammonium salts of these acids.

A reducing compound can be added to the reaction mixture to impart additional surface area to the resulting catalyst composition. Lactic acid is preferred for this purpose, but other compounds bearing bifunctional groups (i.e., bifunctional compounds) such as citric acid, glycolic acid, oxalic acid, ethylene glycol, butane diol, hexane diol, or pentane diol may also be used. Use of these surface area reagents is optional, but is generally preferred. In one aspect of the invention, the bifunctional compound can be added to the mixture of catalyst components before the heat-treating step (c). In one aspect of the invention, the bifunctional compound comprises lactic acid.

A practical example of a method for preparing the catalyst composition according to the invention includes mixing a 50 wt % aqueous solution of TBALDH with a solution of ammonium metavanadate and phosphoric acid in water and, optionally, lactic acid; heating the mixture at 130° C. under agitation; removing water from the heat-treated mixture by distillation; and calcining the resulting residue at 300° C. and then at 450° C. in air.

Alternatively, according to another embodiment of the invention, the catalyst composition may be prepared as described above except that a water-miscible non-solubilizing solvent, or "anti-solvent," is added to the reaction/heat-treating vessel to precipitate out the majority of the catalyst components after the heat-treating step. In this way, energy intensive water removal by distillation can be avoided, and the catalyst composition may instead be collected by filtration followed by calcination. The anti-solvent may be polar compounds such as alcohols, ketones, aldehydes, ethers, or esters. Alcohols such as ethanol are preferred as the anti-solvent.

The catalyst composition can have the general formula $VTi_aP_bO_c$, wherein a=0.3 to 6.0, preferably 1.0 to 4.0; b=2.0 to 13.0, preferably 4.0 to 10.0; and c is the number of atoms required to satisfy the valences of the components other than oxygen.

The catalyst composition of the invention can be supported on an oxide support. Suitable oxide supports include silica, alumina, titanium oxide, zirconium oxide, and titanium or zirconium pyrophosphates. Other oxide supports may be used provided that they are inert to the desired catalytic reaction. The supports should be physically robust and pre-shaped. The term "pre-shaped" is used in this context to mean that the shape of the final catalyst is essentially the same as the starting support. The pre-shaped oxides typically can have average particle diameter sizes ranging from about 0.1 millimeter (mm) to about 20 mm. They can be in any common form such as extrudates, compressed pellets, or bulk solid that has been pulverized to the desired mesh size. They may also be in a variety of shapes such as rods, stars, cylinders, spheres, or broken chunks. Many of these oxide supports are available commercially, and their use simplifies the preparation of the catalyst composition of the invention, although this is not a requirement of the invention.

In supported embodiments, the titanium and the vanadium components can be loaded onto the support separately or together. A preferred technique is to dissolve the desired amount of ammonium vanadate and oxalic acid or lactic acid in the aqueous TBALDH solution. This solution can be diluted if desired and then used to impregnate the oxide support using the incipient wetness technique. The impregnated support is then dried at about 110° C. The resulting material likely contains a homogeneous dispersion of the two metals since drying the solution at 110° C. produces a homogeneous glass. The dried support containing the vanadium and titanium is then impregnated with the desired amount of the aqueous solution of the phosphorus compound.

The order of impregnation normally is not critical. Excellent results can be obtained by co-impregnation with vanadium and titanium followed by impregnation with phosphorus after drying as illustrated above.

Excellent results can also be obtained using incipient wetness techniques for all of the impregnations. If a higher loading is required, more solution than required for incipient wetness can be used followed by evaporation of the solvent. If desired, the solutions can be applied to the outer regions of the oxide support.

After the vanadium, titanium, and phosphorus components have been applied to the support, the catalyst can be calcined, for example, at about 450° C.

The ternary V—Ti—P catalyst composition disclosed herein is primarily amorphous, as determined by X-ray diffraction analysis. Interestingly, the invention V—Ti—P catalyst composition prepared with TBALDH, for example, produces acrylic acid in significantly higher yield (>20%) than the V—Ti—P material prepared with tetrachlorotitanium when a 55 weight percent aqueous formaldehyde feed is used, even though both catalysts are amorphous materials. This result suggests that the microstructure or the homogeneity of the invention catalyst is considerably different than that of the prior art catalyst.

In addition to higher yield, using a water-soluble titanium source offers several advantages over using titanium chloride. For example, the formation of gaseous hydrochloric acid can be avoided; the discrete titanium(IV) precursor is a solute in water rather than a cumbersome heterogeneous gel; and the resulting V—Ti—P catalyst is formed with an inherently higher specific surface area.

The propensity for a water-soluble titanium compound, such as TBALDH, to form an active V—Ti—P catalyst comes as a surprise, since titanium sources other than $TiCl_4$ have been shown to produce inferior catalysts for acrylic acid production. See, for example, M. Ai, *Applied Catalysis*, Vol. 48, pp. 51-61 (1989). For example, when titanium dioxide is employed as a titanium precursor, the resulting material fails to generate acrylic acid from formaldehyde and acetic acid. It has been reported elsewhere that $TiO_2$ can form catalytically active materials for acrylate production (M. Abon et al., *J. Catalysis*, Vol. 156, pp. 28-36 (1995)); however, this result could not be reproduced.

Also unexpected is the fact that exogenous lactic acid is no longer required in the catalyst synthesis, for example, when TBALDH is used. When lactic acid is omitted from the catalyst preparation involving tetrachlorotitanium, the resulting material is highly crystalline, as determined by X-ray diffraction, but is relatively inactive toward acrylic acid synthesis. However, V—Ti—P materials prepared with TBALDH, for example, in the absence of lactic acid are amorphous and are considerably more active and selective. Avoiding lactic acid addition is appealing, since it minimizes the amount of steps in the catalyst synthesis and results in less organic material that must be combusted during air calcination.

In a third aspect, the present invention provides a process for preparing a 2,3-unsaturated carboxylic acid, such as acrylic acid or methacrylic acid. Reference to "carboxylic acid" in this context includes the corresponding carboxylic acid ester, such as acrylate and methacrylate.

The process of the invention comprises the step of contacting a formaldehyde source with a carboxylic acid in the presence of a condensation catalyst under vapor-phase condensation conditions to obtain the 2,3-unsaturated carboxylic acid. The condensation catalyst comprises a mixed oxide of vanadium (V), titanium (Ti), and phosphorus (P). The titanium component of the condensation catalyst is derived from a water-soluble, redox-active organo-titanium compound, as described herein.

The 2,3-unsaturated carboxylic acid can be prepared with good yield, conversion, and selectivity. By "yield" it is meant the (moles of product)/(moles of reactant fed)*100. For example, the % yield of acrylic acid from formaldehyde is the (moles of acrylic acid)/(moles of formaldehyde fed) *100. By "conversion" it is meant the (moles of reactant fed−moles of unreacted reactant)/(moles of reactant fed) *100. For example, the % formaldehyde conversion is (moles of formaldehyde fed−moles of unreacted formaldehyde)/(moles of formaldehyde fed)*100. By "selectivity" it is meant (moles of product)/(moles of reactant fed−moles of unreacted reactant)*100. For example, % selectivity to acrylic acid from formaldehyde is (moles of acrylic acid)/ (moles of formaldehyde fed−moles of unreacted formaldehyde)*100. One skilled in the art recognizes that yield is also equal to conversion times selectivity. When comparing examples, such as, Example B has an 80% formaldehyde conversion and Example C has a 60% formaldehyde conversion, the formaldehyde conversion of Example B is said to be 20% higher than Example C. In other words, comparisons are simply the mathematical difference in the percentages from one example to another.

The formaldehyde source for use in the present invention is not particularly limiting. It can be anhydrous formaldehyde itself, 1,3,5-trioxane (sometimes referred to herein as simply "trioxane"), dimethoxymethane. Alternatively, the formaldehyde source may be an aqueous solution of formaldehyde. The aqueous formaldehyde solution can contain, for example, from 30 to 65 weight percent formaldehyde. Examples of such solutions include formalin (37 wt % formaldehyde) and industrial grade aqueous formaldehyde (55 wt % formaldehyde). The aqueous formaldehyde solution may be obtained commercially, by oxidation of methanol, or by blending water with trioxane, for example, in a molar ratio of approximately 4:1.

The carboxylic acid should have at least 2 hydrogen atoms in the position alpha to the carboxylic acid group. The carboxylic acid is preferably an aliphatic carboxylic acid having 2 to 4 carbon atoms. Acetic and propionic acids are preferred carboxylic acids. The most preferred carboxylic acid is acetic acid. The term "carboxylic acid" in this context includes the corresponding carboxylic acid ester, when formation of the 2,3-unsaturated carboxylic acid ester is desired. Examples of such carboxylic acid esters include acetate and propionate.

The description of the catalyst composition and the process for making the catalyst composition herein above, such as, for example, the description of vanadium, titanium, phosphorus, and alkali metal compounds, the catalyst formula, the alkali metals, the pre-shaped supports, the water removal step, and the bifunctional compound, apply to the process for preparing a 2,3-unsaturated carboxylic acid.

The molar ratio of the formaldehyde component to the carboxylic acid component may be from 0.1 to 10, preferably from 0.2 to 5, and more preferably from 0.2 to 2. The molar ratio of water to the formaldehyde component may be from 0 to 5, preferably from 0 to 3, and more preferably from 0 to 1.5.

The process can be operated at a temperature from 200° C. to 400° C., preferably from 225° C. to 375° C., and more preferably from 275° C. to 375° C.

The process can be run at a pressure from 0.1 to 10 bars absolute (bara), preferably from 0.5 to 5 bara, and more preferably from 1 to 1.5 bara.

In certain embodiments of the process of the invention, the liquid feed rate can range from 1.0 to 1000 mL/kg catalyst/minute, and preferably from 10 to 100 mL/kg catalyst/minute.

In other embodiments of the process of the invention, the reactants can be fed to the condensation reactor with oxygen along with an inert carrier gas such as nitrogen or oxygen-depleted air. Gases recycled from the process can be used. The inert gas component can be present at concentrations ranging from 0 to 90 mole % of the total feed, preferably from 25 to 85 mole %, and more preferably from 30 to 80 mole %. The concentration of the oxygen component can range from 0.5 to 6 mole %, preferably from 2 to 5 mole %, and more preferably from 3 to 4 mole %. Low levels of oxygen allow for coke to build up on the catalyst. On the other hand, high levels of oxygen can lead to excessive combustion of reactants and products.

In the oxygen co-feed embodiments, the space velocity should preferably range from 50 to 400 moles of feed/(kg catalyst-hr), more preferably from 100 to 300 moles of feed/(kg catalyst-hr), and most preferably from 125 and 200 moles of feed/(kg catalyst-hr). The term "moles of feed" is meant to be inclusive of all of the species being fed to the catalyst including organics, water, oxygen, and inerts. These embodiments of the invention take advantage of the combined effects of feeding the correct levels of oxygen, water, and elevated space velocity to increase rate and selectivity without significantly affecting the yield. Any differences in formaldehyde conversion are primarily the result of formaldehyde destruction when the space velocity is too low. In the event of inhibitory coke formation, the catalyst may be regenerated between reaction runs in air at, for example, 400° C.

Generally, increasing the space velocity of reactants increases the rate of a reaction, but this is normally accompanied with a corresponding decrease in the yield and conversion. It has been unexpectedly discovered that certain conditions of the process can actually allow for increased rate without a decrease in yield as the space velocity is increased.

Inhibitors such as hydroquinone may be added to the 2,3-unsaturated carboxylic acid product to minimize polymerization.

In a fourth aspect, the present invention provides a process for preparing a 2,3-unsaturated carboxylic acid. The process comprises the steps of contacting a methylene dialkanoate and a diluent gas with a condensation catalyst under vapor-phase condensation conditions to obtain the 2,3-unsaturated carboxylic acid. The condensation catalyst comprises a mixed oxide of vanadium (V), titanium (Ti), and phosphorus (P). The methylene dialkanoate has the general formula (I):

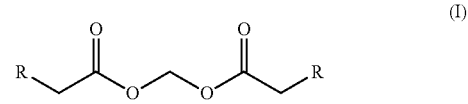

wherein R is selected from the group consisting of hydrogen and an alkyl group having 1 to 8 carbon atoms.

By "methylene dialkanoate," it is meant that a —$CH_2$—, methylene group, is bonded to two alkanoate, carboxylate, groups. The alkanoate group should have at least 2 hydrogen atoms bonded to a carbon atom in the position alpha to the carboxylate carbon. Acetate and propionate are preferred alkanoates.

By "diluent gas," it is meant a gas which is introduced so that this gas quantitatively lowers the concentration of the reactants in feed. The composition of the "diluent gas" can be an inert carrier gas and/or oxygen; some examples of an inert gas include nitrogen, argon, oxygen depleted air, or air.

By "condensation catalyst," it is meant a homogeneous or heterogeneous catalyst that can combine reactant molecules with the concomitant elimination of water or other by-product molecules.

By "an alkyl group with 1 to 8 carbon atoms," it is meant any saturated hydrocarbon with 1 up to and including 8 carbons atoms. Some examples of alkyl groups include methyl, ethyl, propyl, iso-propyl, butyl, isobutyl, tert-butyl, pentyl, hexyl, heptyl, and octyl.

The condensation catalyst comprises a mixed oxide of vanadium (V), titanium (Ti), and phosphorus (P). These catalysts can be made by methods well known to one skilled in the art. The process can be carried out using a catalyst having the general formula $VTi_aP_bO_c$, wherein a=0.3 to 6.0, preferably 1.0 to 4.0; b=2.0 to 13.0, preferably 4.0 to 10.0; and c is the number of atoms required to satisfy the valences of the components other than oxygen.

In another aspect of the invention the $VTi_aP_bO_c$ catalyst can be the inventive catalyst wherein the titanium component is derived from a water-soluble, redox-active organo-titanium compound. Examples of water-soluble, redox-active organo-titanium compounds useful in the $VTi_aP_bO_c$ catalyst include titanium lactates, titanium alkanolamines, and titanium acetylacetonates. Such compounds are commercially available, such as from Dorf Ketal under the trade name TYZOR®. Practical examples of such compounds include titanium(IV) bis(ammonium lactate)dihydroxide (TBALDH), titanium diethanolamine, titanium triethanolamine, and titanium acetylacetonate. In one aspect, the organo-titanium compound comprises titanium(IV) bis(ammonium lactate)dihydroxide.

The molar ratio of water to the methylene dialkanoate component may be between about 0 and 5, preferably between 0 and 1, and most preferably at 0.

The process for preparing 2,3-unsaturated carboxylic acids can be operated at a temperature between about 150° C. and 400° C., preferably between 200° C. and 375° C. and most preferably between 220° C. and 320° C. The process is normally operated at a pressure between about 0.1 and 10 bars absolute (bara), preferably between 0.5 and 5 bara and most preferably between about 1 and 1.5 bara.

The process for preparing 2,3-unsaturated carboxylic acids can be performed when the methylene dialkanoate is methylene dipropionate. This process can also be performed when the methylene dialkanoate is methylene diacetate. Experiments performed with methylene diacetate or methylene dipropionate produced no detectable paraformaldehyde in the process's reaction product and produced higher space time yields than conventional feeds.

The methylene dialkanoate is contacted with the condensation catalyst in the presence of a diluent gas. This diluent gas can be an inert carrier gas and/or oxygen. Gases recycled from the process can be used. The diluent gas component can be present at concentrations between 1 and 90 mole percent based on the total moles of the methylene dialkanoate and diluent gas, preferably between about 25 and 75 mole percent, and most preferably between about 30 and 65 mole percent.

The oxygen concentration can be between about 0.5 to 20 mole % based on the total moles of diluent gas, preferably between 2 and 10 mole %, and most preferably between about 4 and 6 mole %. Low levels of oxygen allow for coke to build up on the catalyst. High levels of oxygen can lead to excessive combustion of reactants and products.

The space time yield is preferably between about 0.1 and 200 moles of 2,3 unsaturated carboxylic acid/(kg catalyst-hr), more preferably between about 1 and 50 moles of 2,3 unsaturated carboxylic acid/(kg catalyst-hr) and most preferably between about 2 and 10 moles of 2,3 unsaturated carboxylic acid/(kg catalyst-hr). In the event of inhibitory coke formation, the catalyst may be regenerated between reaction runs in air at 400° C.

In a fifth aspect, the present invention provides a process for preparing a 2,3-unsaturated carboxylic acid. The process comprises the step of contacting a methylene dialkanoate and diluent gas with a condensation catalyst under vapor-phase condensation conditions to obtain the 2,3-unsaturated carboxylic acid. The condensation catalyst comprises a mixed oxide of vanadium (V), titanium (Ti), and phosphorus (P). The titanium component is derived from a water-soluble, redox-active organo-titanium compound. The methylene dialkanoate has the general formula (I):

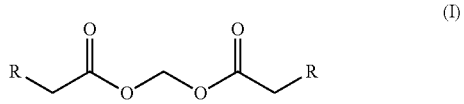

(I)

wherein R is selected from the group consisting of hydrogen, methyl, ethyl, propyl, and isopropyl.

The description of the catalyst composition, the process for making the inventive catalyst composition, and the processes for preparing a 2,3-unsaturated carboxylic acid herein above, such as, for example, the description of vanadium, titanium, phosphorus, and alkali metal compounds, the catalyst formula, the alkali metals, the pre-shaped supports, the water removal step, and the bifunctional compound, apply to the process for preparing a 2,3-unsaturated carboxylic acid.

For example, the process can be carried out using a catalyst having the general formula $VTi_aP_bO_c$, wherein a=0.3 to 6.0, preferably 1.0 to 4.0; b=2.0 to 13.0, preferably 4.0 to 10.0; and c is the number of atoms required to satisfy the valences of the components other than oxygen.

Examples of water-soluble, redox-active organo-titanium compounds useful in the $VTi_aP_bO_c$ catalyst include titanium lactates, titanium alkanolamines, and titanium acetylacetonates. Such compounds are commercially available, such as from Dorf Ketal under the trade name TYZOR®. Practical examples of such compounds include titanium(IV) bis(ammonium lactate)dihydroxide (TBALDH), titanium diethanolamine, titanium triethanolamine, and titanium acetylacetonate. In one aspect, the organo-titanium compound comprises titanium(IV) bis(ammonium lactate)dihydroxide.

The molar ratio of water to the methylene dialkanoate component may be between about 0 and 5, preferably between 0 and 1, and most preferably at 0.

The process for preparing 2,3-unsaturated carboxylic acids can be operated at a temperature between about 150° C. and 400° C., preferably between 200° C. and 375° C. and most preferably between 220° C. and 320° C. The process is normally operated at a pressure between about 0.1 and 10 bars absolute (bara), preferably between 0.5 and 5 bara and most preferably between about 1 and 1.5 bara.

The process for preparing 2,3-unsaturated carboxylic acids can be performed when the methylene dialkanoate is methylene dipropionate. This process can also be performed when the methylene dialkanoate is methylene diacetate. Experiments performed with methylene diacetate or methylene dipropionate produced no detectable paraformaldehyde in the process's reaction product and produced higher space time yields than comparable conventional feeds.

The methylene dialkanoate is fed with a diluent gas to achieve contact with the condensation catalyst. This diluent gas can be an inert carrier gas and/or oxygen. Gases recycled from the process can be used. The diluent gas component can be present at concentrations between 1 and 90 mole percent based on the total moles of the methylene dialkanoate and diluent gas, preferably between about 25 and 75 mole percent, and most preferably between about 30 and 65 mole percent.

The oxygen concentration can be between about 0.5 to 20 mole based on the total moles of diluent gas, preferably between 2 and 10 mole %, and most preferably between about 4 and 6 mole %. Low levels of oxygen allow for coke to build up on the catalyst. High levels of oxygen can lead to excessive combustion of reactants and products.

The space time yield should preferably range between about 0.1 and 200 moles of 2,3 unsaturated carboxylic acid/(kg catalyst-hr), more preferably between about 1 and 50 moles of 2,3 unsaturated carboxylic acid/(kg catalyst-hr) and most preferably between about 2 and 10 moles of 2,3 unsaturated carboxylic acid/(kg catalyst-hr). In the event of inhibitory coke formation, the catalyst may be regenerated between reaction runs in air at 400° C.

In a sixth aspect, the present invention is a process for preparing a 2,3-unsaturated carboxylic acid comprising: contacting a formaldehyde source, a carboxylic acid, and a diluent gas with a condensation catalyst under vapor-phase condensation conditions to obtain the 2,3-unsaturated carboxylic acid; wherein the condensation catalyst comprises a mixed oxide of vanadium (V), titanium (Ti), and phosphorus (P); wherein the diluent gas comprises from about 3 mol % to about 5 mol % oxygen, based on the total moles of feed; and wherein the process has a selectivity of greater than about 40% and a conversion of greater than about 40%.

The formaldehyde source used in the present invention is not particularly limiting. It can be anhydrous formaldehyde itself, 1,3,5-trioxane (sometimes referred to herein as simply "trioxane"), dimethoxymethane. Alternatively, the formaldehyde source may be an aqueous solution of formaldehyde. The aqueous formaldehyde solution can contain, for example, from 30 to 65 weight percent formaldehyde. Examples of such solutions include formalin (37 wt % formaldehyde) and industrial grade aqueous formaldehyde (55 wt % formaldehyde). The aqueous formaldehyde solution may be obtained commercially, by oxidation of methanol, or by blending acetic acid with trioxane, for example, in a molar ratio of approximately 4:1.

The carboxylic acid should have at least 2 hydrogen atoms in the position alpha to the carboxylic acid group. The carboxylic acid is preferably an aliphatic carboxylic acid having 2 to 4 carbon atoms. Acetic and propionic acids are preferred carboxylic acids. The most preferred carboxylic acid is acetic acid. The term "carboxylic acid" in this context includes the corresponding carboxylic acid ester, when formation of the 2,3-unsaturated carboxylic acid ester is desired. Examples of such carboxylic acid esters include acetate and propionate.

The molar ratio of the formaldehyde component to the carboxylic acid component may be from 0.1 to 10, preferably from 0.2 to 5, and more preferably from 0.2 to 2. The molar ratio of water to the formaldehyde component may be from 0 to 5, preferably from 0 to 3, and more preferably from 0 to 1.5.

The process can be operated at a temperature from 200° C. to 400° C., preferably from 225° C. to 375° C., and more preferably from 275° C. to 375° C.

The process can be run at a pressure from 0.1 to 10 bars absolute (bara), preferably from 0.5 to 5 bara, and more preferably from 1 to 1.5 bara.

In certain embodiments of the process of the invention, the liquid feed rate can range from 1.0 to 1000 mL/kg catalyst/minute, and preferably from 10 to 100 mL/kg catalyst/minute.

In other embodiments of the process of the invention, the reactants can be fed to the condensation reactor with oxygen along with an inert carrier gas such as nitrogen or oxygen-depleted air. Gases recycled from the process can be used. The inert gas component can be present at concentrations ranging from 0 to 90 mole % of the total feed, preferably from 25 to 85 mole %, and more preferably from 30 to 80 mole %. The concentration of the oxygen component can range from 3 to 5 mole %, from 3 to 4 mole %, and more preferably from 3.5 to 4 mole %. In one embodiment, the concentration of the oxygen component can be about 3.6 mole %, about 3.7 mole %, about 3.8 mole %, or about 3.9 mole %. Each of these mole % values are based on the total moles of feed including each of the added liquids and diluent gases. Too low or nonexistent levels of oxygen allow for coke to build up on the catalyst. On the other hand, high levels of oxygen can lead to excessive combustion of reactants and products.

In the oxygen co-feed embodiments, the space velocity should preferably range from 50 to 400 moles of feed/(kg catalyst-hr), more preferably from 100 to 300 moles of feed/(kg catalyst-hr), and most preferably from 125 and 200 moles of feed/(kg catalyst-hr). The term "moles of feed" is meant to be inclusive of all of the species being fed to the catalyst including organics, water, oxygen, and inerts. These embodiments of the invention take advantage of the combined effects of feeding the correct levels of oxygen, water, and elevated space velocity to increase rate and selectivity without significantly affecting the yield. Any differences in formaldehyde conversion are primarily the result of formaldehyde destruction when the space velocity is too low. In the event of inhibitory coke formation, the catalyst may be regenerated between reaction runs in air at, for example, 400° C.

The formaldehyde conversion of the process can have a conversion of greater than about 50%, greater than about 55%, greater than about 60%, greater than about 65%, greater than about 70%, greater than about 75%, greater than about 80%, greater than about 90%, or greater than about 95%.

The formaldehyde selectivity of the process can have a selectivity of greater than about 50%, greater than about 55%, greater than about 60%, greater than about 65%, greater than about 70%, greater than about 75%, greater than about 80%, greater than about 90%, or greater than about 95%.

Depending on the amount of oxygen used in the reaction and process, the combination of the conversion and selectivity of the process can be any combination of the different values listed above for the selectivity and conversion.

The catalyst composition according to the present invention can have the general formula $VTi_aP_bO_c$, wherein a=0.3 to 6.0, preferably 1.0 to 4.0; b=2.0 to 13.0, preferably 4.0 to 10.0; and c is the number of atoms required to satisfy the valences of the components other than oxygen.

Examples of water-soluble, redox-active organo-titanium compounds useful in the $VTi_aP_bO_c$ catalyst include titanium lactates, titanium alkanolamines, and titanium acetylacetonates. Such compounds are commercially available, such as from Dorf Ketal under the trade name TYZOR®. Practical examples of such compounds include titanium(IV) bis(ammonium lactate)dihydroxide (TBALDH), titanium diethanolamine, titanium triethanolamine, and titanium acetylacetonate. In one aspect, the organo-titanium compound comprises titanium(IV) bis(ammonium lactate)dihydroxide.

In one embodiment the formaldehyde source used in the present invention can be a methylene dialkanoate which has the following general formula (I):

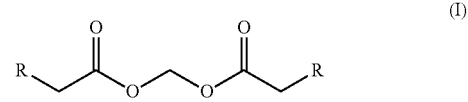

wherein R is selected from the group consisting of hydrogen and an alkyl group having 1 to 8 carbon atoms. By "methylene dialkanoate," it is meant that a —$CH_2$—, methylene group, is bonded to two alkanoate, carboxylate, groups. The alkanoate group should have at least 2 hydrogen atoms bonded to a carbon atom in the position alpha to the carboxylate carbon. Acetate and propionate are preferred alkanoates.

LISTING OF NON-LIMITING EMBODIMENTS

Embodiment A is a catalyst composition comprising a mixed oxide of vanadium (V), titanium (Ti), and phosphorus (P), wherein the titanium component is derived from a water-soluble, redox-active organo-titanium compound.

The catalyst composition of Embodiment A which has the general formula $VTi_aP_bO_c$, wherein a is a number from 0.3 to 6.0, b is a number from 2.0 to 13.0, and c is the number of atoms required to satisfy the valences of V, Ti, and P; or wherein a ranges from 1.0 to 4.0 and b ranges from 4.0 to 10.0.

The catalyst composition of Embodiment A or Embodiment A with one or more of the intervening features wherein the organo-titanium compound comprises titanium(IV) bis(ammonium lactate)dihydroxide.

The catalyst composition of Embodiment A or Embodiment A with one or more of the intervening features which further comprises a pre-shaped support.

The catalyst composition of Embodiment A or Embodiment A with one or more of the intervening features which further comprises a pre-shaped support, wherein the pre-shaped support comprises silica, alumina, titanium oxide, titanium pyrophosphate, zirconium oxide, or zirconium pyrophosphate.

The catalyst composition of Embodiment A or Embodiment A with one or more of the intervening features which further comprises a pre-shaped support, wherein the pre-shaped support has a particle size ranging from 0.1 mm to 20 mm.

Embodiment B is a method for preparing a catalyst composition comprising a mixed oxide of vanadium (V), titanium (Ti), and phosphorus (P). The method comprises the steps of:
(k) providing an aqueous solution comprising a water-soluble, redox-active organo-titanium compound;
(l) adding a vanadium compound and a phosphorus compound to the aqueous titanium solution to form a mixture of catalyst components;
(m) heat-treating the mixture;
(n) removing water from the heat-treated mixture to obtain a solid residue comprising the catalyst components; and
(o) calcining the solid residue at an elevated temperature in the presence of air to obtain the catalyst composition.

The method of Embodiment B wherein the water removing step (d) comprises distillation or evaporation.

The method of Embodiment B wherein the water removing step (d) comprises adding an anti-solvent to the mixture to precipitate out the catalyst components and separating the precipitate from the liquid to obtain the solid residue.

The method of Embodiment B wherein the water removing step (d) comprises adding an anti-solvent to the mixture to precipitate out the catalyst components and separating the precipitate from the liquid to obtain the solid residue, and wherein the precipitate is separated from the liquid by filtration.

The method of Embodiment B wherein the water removing step (d) comprises adding an anti-solvent to the mixture to precipitate out the catalyst components and separating the precipitate from the liquid to obtain the solid residue, wherein the precipitate is separated from the liquid by filtration, and wherein the anti-solvent is a polar compound selected from alcohols, ketones, aldehydes, ethers, and esters; or wherein the anti-solvent is an alcohol.

The method of Embodiment B or Embodiment B with one or more of the intervening features wherein the catalyst composition has the general formula $VTi_aP_bO_c$, wherein a is a number from 0.3 to 6.0, b is a number from 2.0 to 13.0, and c is the number of atoms required to satisfy the valences of V, Ti, and P; or wherein a ranges from 1.0 to 4.0, and b ranges from 4.0 to 10.0.

The method of Embodiment B or Embodiment B with one or more of the intervening features wherein the organo-titanium compound comprises titanium(IV) bis(ammonium lactate)dihydroxide.

The method of Embodiment B or Embodiment B with one or more of the intervening features wherein the catalyst composition further comprises a pre-shaped support.

The method of Embodiment B or Embodiment B with one or more of the intervening features which further comprises a pre-shaped support, wherein the pre-shaped support comprises silica, alumina, titanium oxide, titanium pyrophosphate, zirconium oxide, or zirconium pyrophosphate.

The method of Embodiment B or Embodiment B with one or more of the intervening features which further comprises a pre-shaped support, wherein the pre-shaped support has a particle size ranging from 0.1 mm to 20 mm.

The method of Embodiment B or Embodiment B with one or more of the intervening features wherein the catalyst composition further comprises a pre-shaped support, and wherein the pre-shaped support is added to the mixture of catalyst components before the heat-treating step (c).

The method of Embodiment B or Embodiment B with one or more of the intervening features which further comprises adding a bifunctional compound to the mixture of catalyst components before the heat-treating step (c), wherein the bifunctional compound comprises citric acid, lactic acid, glycolic acid, oxalic acid, ethylene glycol, butane diol, pentane diol, or hexane diol; or wherein the bifunctional compound comprises lactic acid.

Embodiment C is a process for preparing a 2,3-unsaturated carboxylic acid. The process comprises the step of contacting a formaldehyde source with a carboxylic acid in the presence of a condensation catalyst under vapor-phase condensation conditions to obtain the 2,3-unsaturated carboxylic acid. The condensation catalyst comprises a mixed oxide of vanadium (V), titanium (Ti), and phosphorus (P). The titanium component of the condensation catalyst is derived from a water-soluble, redox-active organo-titanium compound.

The process of Embodiment C wherein the formaldehyde source comprises formaldehyde, 1,3,5-trioxane, or dimethoxymethane, and the carboxylic acid comprises acetic acid or propionic acid.

The process of Embodiment C or Embodiment C with one or more of the intervening features wherein the formaldehyde source comprises an aqueous solution of formaldehyde, 1,3,5-trioxane, or dimethoxymethane, and the carboxylic acid comprises acetic acid or propionic acid.

The process of Embodiment C or Embodiment C with one or more of the intervening features wherein the formaldehyde source comprises an aqueous solution of formaldehyde, 1,3,5-trioxane, or dimethoxymethane, and the carboxylic acid comprises acetic acid or propionic acid, and wherein the aqueous solution comprises from 30 to 65 weight percent formaldehyde.

The process of Embodiment C or Embodiment C with one or more of the intervening features wherein the organo-titanium compound comprises titanium(IV) bis(ammonium lactate)dihydroxide.

The process of Embodiment C or Embodiment C with one or more of the intervening features wherein the catalyst composition further comprises a pre-shaped support.

The process of Embodiment C or Embodiment C with one or more of the intervening features which further comprises a pre-shaped support, wherein the pre-shaped support comprises silica, alumina, titanium oxide, titanium pyrophosphate, zirconium oxide, or zirconium pyrophosphate.

The process of Embodiment C or Embodiment C with one or more of the intervening features which further comprises a pre-shaped support, wherein the pre-shaped support has a particle size ranging from 0.1 mm to 20 mm.

The process of Embodiment C or Embodiment C with one or more of the intervening features wherein the condensation conditions comprise a total feed space velocity of 50 to 400 moles of feed/(kg catalyst·hr); or the total feed space velocity ranges from 100 to 300 moles of feed/(kg catalyst·hr); or the total feed space velocity ranges from 125 to 200 moles of feed/(kg catalyst·hr).

This invention can be further illustrated by the following working examples, although it will be understood that these examples are included merely for purposes of illustration and are not intended to limit the scope of the invention. Unless otherwise indicated or the context indicates otherwise, all percentages are by weight.

Embodiment D is a process for preparing a 2,3-unsaturated carboxylic acid. The process comprises the step of contacting a methylene dialkanoate and a diluent gas with a condensation catalyst under vapor-phase condensation conditions to obtain the 2,3-unsaturated carboxylic acid. The condensation catalyst comprises a mixed oxide of vanadium (V), titanium (Ti), and phosphorus (P). The methylene dialkanoate has the general formula (I):

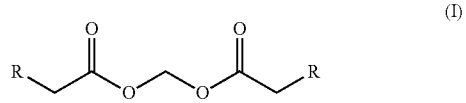

(I)

wherein the R is selected from the group consisting of hydrogen and an alkyl group having 1 to 8 carbons.

The process of Embodiment D wherein the condensation catalyst has the formula $VTi_aP_bO_c$, wherein a is a number from 0.3 to 6.0, b is a number from 2.0 to 13.0, and c is the number of atoms required to satisfy the valences of the components other than oxygen.

The process of Embodiment D or Embodiment D with one or more of the intervening features wherein the titanium component is derived from a water-soluble, redox-active organo-titanium compound.

The process of Embodiment D or Embodiment D with one or more of the intervening features wherein the organo-titanium compound comprises titanium(IV) bis(ammonium lactate)dihydroxide.

The process of Embodiment D or Embodiment D with one or more of the intervening features wherein the methylene dialkanoate is methylene dipropionate.

The process of Embodiment D or Embodiment D with one or more of the intervening features wherein the methylene dialkanoate is methylene diacetate.

The process of Embodiment D or Embodiment D with one or more of the intervening features wherein the contacting occurs with 1 mole to 90 mole % diluent gases, based on the total moles of the methylene dialkanoate and the diluent gas.

The process of Embodiment D or Embodiment D with one or more of the intervening features wherein the diluent gas comprises from about 0.5 mole % to about 20 mole % oxygen, based on the total moles of diluent gas.

The process of Embodiment D or Embodiment D with one or more of the intervening features wherein the space time yield of the 2,3 unsaturated carboxylic acid is from about 0.1 and 200 moles of 2,3 unsaturated carboxylic acid/(kg catalyst-hr), more preferably between about 1 and 50 moles of 2,3 unsaturated carboxylic acid/(kg catalyst-hr) and most preferably between about 2 and 10 moles of 2,3 unsaturated carboxylic acid/(kg catalyst-hr).

The process of Embodiment D or Embodiment D with one or more of the intervening features wherein the catalyst composition further comprises a pre-shaped support.

The process of Embodiment D or Embodiment D with one or more of the intervening features which further comprises a pre-shaped support, wherein the pre-shaped support comprises silica, alumina, titanium oxide, titanium pyrophosphate, zirconium oxide, or zirconium pyrophosphate.

The process of Embodiment D or Embodiment D with one or more of the intervening features which further comprises a pre-shaped support, wherein the pre-shaped support has a particle size ranging from 0.1 mm to 20 mm.

Embodiment E is a process for preparing a 2,3-unsaturated carboxylic acid. The process comprises the step of contacting a methylene dialkanoate and a diluent gas with a condensation catalyst under vapor-phase condensation conditions to obtain the 2,3-unsaturated carboxylic acid. The condensation catalyst comprises a mixed oxide of vanadium (V), titanium (Ti), and phosphorus (P). The titanium component is derived from a water-soluble, redox-active organo-titanium compound. The methylene dialkanoate has the general formula (I):

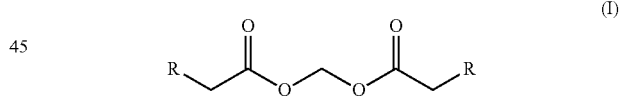

(I)

wherein the R is selected from the group consisting of hydrogen, methyl, ethyl, propyl, and isopropyl.

The process of Embodiment E wherein the organo-titanium compound comprises titanium(IV) bis(ammonium lactate)dihydroxide.

The process of Embodiment E or Embodiment E with one or more of the intervening features wherein the condensation catalyst has the formula $VTi_aP_bO_c$, wherein a is a number from 0.3 to 6.0, b is a number from 2.0 to 13.0, and c is the number of atoms required to satisfy the valences of the components other than oxygen.

The process of Embodiment E or Embodiment E with one or more of the intervening features wherein the methylene dialkanoate is methylene dipropionate.

The process of Embodiment E or Embodiment E with one or more of the intervening features wherein the methylene dialkanoate is methylene diacetate.

The process of Embodiment E or Embodiment E with one or more of the intervening features wherein the contacting occurs with between 1 and 90 mole percent based on the total moles of the methylene dialkanoate and diluent gas, preferably between about 25 and 75 mole percent, and most preferably between about 30 and 65 mole percent.

The process of Embodiment E or Embodiment E with one or more of the intervening features wherein the diluent gas comprises from about 0.5 to 20 mole % oxygen, based on the total moles of diluent gas, preferably between 2 and 10 mole %, and most preferably between about 4 and 6 mole %.

The process of Embodiment E or Embodiment E with one or more of the intervening features wherein the space time yield of the 2,3 unsaturated carboxylic acid is from about 0.1 and 200 moles of 2,3 unsaturated carboxylic acid/(kg catalyst-hr), more preferably between about 1 and 50 moles of 2,3 unsaturated carboxylic acid/(kg catalyst-hr) and most preferably between about 2 and 10 moles of 2,3 unsaturated carboxylic acid/(kg catalyst-hr).

The process of Embodiment E or Embodiment E with one or more of the intervening features wherein the catalyst composition further comprises a pre-shaped support.

The process of Embodiment E or Embodiment E with one or more of the intervening features which further comprises a pre-shaped support, wherein the pre-shaped support comprises silica, alumina, titanium oxide, titanium pyrophosphate, zirconium oxide, or zirconium pyrophosphate.

The process of Embodiment E or Embodiment E with one or more of the intervening features which further comprises a pre-shaped support, wherein the pre-shaped support has a particle size ranging from 0.1 mm to 20 mm.

Embodiment F is a process for preparing a 2,3-unsaturated carboxylic acid. The process comprises the step of contacting a formaldehyde source, a carboxylic acid, and a diluent gas with a condensation catalyst under vapor-phase condensation conditions to obtain the 2,3-unsaturated carboxylic acid. The condensation catalyst comprises a mixed oxide of vanadium (V), titanium (Ti), and phosphorus (P). The diluent gas comprises from about 3 mol % to about 5 mol % oxygen, based on the total moles of feed. The process has a selectivity of greater than about 40% and a conversion of greater than about 40%.

The method of Embodiment F wherein the diluent gas comprises from about 3 mol % to about 4 mol % oxygen, based on the total moles of feed (liquids and diluent gas).

The method of Embodiment F or Embodiment F with one or more of the intervening features wherein the diluent gas comprises from about 3.5 mol % to about 4 mol % oxygen, based on the total moles of feed (liquids and diluent gas).

The method of Embodiment F or Embodiment F with one or more of the intervening features wherein the process has a selectivity of greater than about 60% and a conversion of greater than about 50%.

The method of Embodiment F or Embodiment F with one or more of the intervening features wherein the condensation catalyst has the formula $VTi_aP_bO_c$, wherein a is a number from 0.3 to 6.0, b is a number from 2.0 to 13.0, and c is the number of atoms required to satisfy the valences of the components other than oxygen.

The method of Embodiment F or Embodiment F with one or more of the intervening features wherein the titanium component is the residue of a water-soluble, redox-active organo-titanium compound.

The method of Embodiment F or Embodiment F with one or more of the intervening features wherein the organo-titanium compound comprises titanium(IV) bis(ammonium lactate) dihydroxide.

The method of Embodiment F or Embodiment F with one or more of the intervening features wherein the formaldehyde source is a methylene dicarboxylate having the general formula (I):

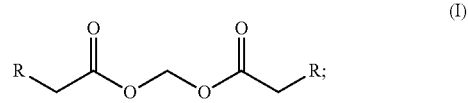

and
wherein R is selected from the group consisting of a hydrogen, methyl, ethyl, propyl, iso-propyl, and an alkyl group having 1 to 8 carbons.

The method of Embodiment F or Embodiment F with one or more of the intervening features wherein the condensation reaction has a total space feed velocity of from 50 to 400 moles of feed/(kg catalyst·hr).

The method of Embodiment F or Embodiment F with one or more of the intervening features wherein the space time yield of the 2,3 unsaturated carboxylic acid is from about 0.1 to about 200 moles of 2,3 unsaturated carboxylic acid per kg catalyst per hour.

Embodiment G is a process for preparing acrylic acid. The process comprises the step of contacting a formaldehyde source, acetic acid, and a diluent gas with a condensation catalyst under vapor-phase condensation conditions to obtain the acrylic acid. The condensation catalyst comprises a mixed oxide of vanadium (V), titanium (Ti), and phosphorus (P). The diluent gas comprises from about 3 mol % to about 5 mol % oxygen, based on the total moles of feed. The process has a selectivity of greater than 40% and a conversion of greater than 40%.

The process of Embodiment G wherein the diluent gas comprises from about 3.5 mol % to about 4 mol % oxygen, based on the total moles of feed (liquids and diluent gas).

The method of Embodiment G or Embodiment G with one or more of the intervening features wherein the process has a selectivity of greater than 60% and a conversion of greater than 50%.

The method of Embodiment G or Embodiment G with one or more of the intervening features wherein the titanium component is the residue of a water-soluble, redox-active organo-titanium compound and wherein the organo-titanium compound comprises titanium(IV) bis(ammonium lactate) dihydroxide.

The method of Embodiment G or Embodiment G with one or more of the intervening features wherein the formaldehyde source comprises a methylene diacetate having the general formula (I):

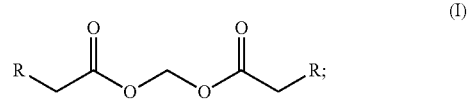

and
wherein R is a hydrogen.

Embodiment H is a process for preparing methacrylic acid. The process comprises the step of contacting a formaldehyde source, propionic acid, and a diluent gas with a condensation catalyst under vapor-phase condensation conditions to obtain the methacrylic acid. The condensation catalyst comprises a mixed oxide of vanadium (V), titanium (Ti), and phosphorus (P). The diluent gas comprises from about 3 mol % to about 5 mol % oxygen, based on the total moles of feed. The process has a selectivity of greater than 40% and a conversion of greater than 40%.

The process of Embodiment H wherein the diluent gas comprises from about 3.5 mol % to about 4 mol % oxygen, based on the total moles of feed.

The method of Embodiment H or Embodiment H with one or more of the intervening features wherein the process has a selectivity of greater than 60% and a conversion of greater than 50%.

The method of Embodiment H or Embodiment H with one or more of the intervening features wherein the titanium component is the residue of a water-soluble, redox-active organo-titanium compound and wherein the organo-titanium compound comprises titanium(IV) bis(ammonium lactate) dihydroxide.

The method of Embodiment H or Embodiment H with one or more of the intervening features wherein the formaldehyde source comprises a methylene dipropionate having the general formula (I):

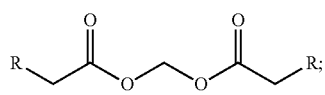

(I)

and
wherein R is a methyl group.

EXAMPLES

Materials

D/L-Lactic acid (90 wt %), ammonium metavanadate (99+ wt % $NH_4VO_3$), phosphoric acid (85 wt % $H_3PO_4$), titanium(IV) bis(ammonium lactate)dihydroxide (50 wt % solution in water), tetrachlorotitanium (99 wt $TiCl_4$), and titanium dioxide colloidal suspension in water (23.38 wt % $TiO_2$) were purchased from commercial suppliers and used as received.

ABBREVIATIONS

XRD=Powder X-ray Diffraction, XRF=X-ray Fluorescence Spectroscopy, TPD=Temperature Programmed Desorption, SCCM=standard cubic centimeters per minute; MeOAc=methyl acetate, MeOH=methanol, MA=methyl acrylate, H2CO=formaldehyde, HOAc=acetic acid, HOPr=propionic acid, mmol=millimoles, prod=product, AA=acrylic acid, BSTFA=N,O-bis(trimethylsilyl)trifluoroacetamide, and TMSCI=trimethylsilyl chloride.

XRD Measurements

All XRD measurements were performed on a Rigaku Miniflex X-Ray Diffraction Spectrometer using a Copper anode X-Ray tube operated at 30 kV and 15 mA. Diffraction patterns were collected from 5 degree two theta angle to 75 degree two theta angle with a sampling width of 0.02 degrees and a scan speed of 1.00 degrees/min.

Crystallite size was calculated based on the measurement of the full width half maximum for peaks in the diffraction pattern and use of the Scherrer equation (P. N. Scherrer, *Ges. Wiss. Gottingen, Math.—Phys*. KI. 2, 96-100 (1918)). Quantitative phase analysis was calculated using a refinement algorithm base on the Rietveld method (H. M. Rietveld, *J. Applied Crystallography* 21, 86-91 (1988)). Percent crystallinity was calculated based on integrated intensities from the individual diffraction patterns with peaks of crystallite size greater than 30 Å defined as crystalline and peaks of crystallite size less than or equal to 30 Å defined as amorphous (N. S. Murthy et al., *Polymers* 31, 996-1002 (1990)).

Temperature Desorption Measurements

TPD determinations were conducted using a Mass Spectrometer attached to the outlet of a Micrometrics Autochem II 2920 analyzer. The determination of total acidity and total basicity using isopropanol as the probe molecule is performed as follows. Approximately 0.05 grams of sample is weighed into a quartz U tube which is placed in a ceramic furnace. The sample is subjected to a programmed temperature cycle that consists of a heat cycle to 450° C. under 10% oxygen in Helium, a cooling step to 40° C. Isopropanol is dosed on the sample using the vapor generator of the Micromeritics Autochem 2920 Analyzer. The vapor generator operates by bubbling helium through a flask containing isopropanol at room temperature. The resulting "vapor-saturated" helium is transferred through a heated sample loop and injected over the sample. After saturating the surface of the sample, dry helium is passed over the sample to remove any physisorbed vapor. Then a final heating to ~450° C. at 20° C./min in a flowing stream of He at which time mass spectral data is collected from the gas flowing through the sample.

Gas Chromatography Measurements

Liquid product samples were collected over a measured time period, weighed, and analyzed by gas chromatography. Samples were weighed into a gas chromatography (GC) vial to a recorded weight of 0.1XXX (where X is the actual number shown on the balance). Then, a LEAP unit was used to robotically add 200 μL of internal standard (0.7325 g dodecane in 100 mL pyridine), followed by 1.0 mL of BSTFA (w/ TMSCI). The vials were then placed on a heat plate at 80° C. for 30 minutes. To separate all components, each sample was injected on two columns running in parallel on one instrument, a Shimadzu 2010 gas chromatograph with an AOC-20 autosampler. Gas Chromatography measurements were used to quantify all components in the liquid product except formaldehyde.

Liquid Chromatography Measurements.

Quantitation of formaldehyde in the liquid product was performed using high performance liquid chromatography after reaction mixture samples were subjected to acid hydrolysis in aqueous 25% v/v $H_2SO_4$ at 80° C. for 30 minutes. The acid hydrolysate was reacted with dinitrophenylhydrazine then analyzed using a Phenomenex Luna C8 column using a 1:1 water:acetonitrile mobile phase under isocratic conditions. Separation and detection of the 2,4-dinitrophenylhydrazone derivative of formaldehyde was carried out using an Agilent 1100 HPLC system with a UV-Vis Detector monitoring at 360 nm. The formaldehyde concentration in the liquid product was calculated based on calibration using external standards prepared from formalin. Quantitation of formaldehyde in the liquid feed was calculated based upon the ratio of water to trioxane and the liquid feed flow rate.

Example 1

Preparation of an Amorphous V—Ti—P Catalyst Via Method a and Reactor Screening with an Anhydrous Liquid Feed 1. Preparation of V(IV) $H_3PO_4$ Solution The orange-beige ammonium metavanadate (9.75 g) was suspended in 50 mL of lactic acid and 200 mL of deionized water in a 500-mL single-necked round-bottomed flask. After heating at 70° C. for 1 hour, 85% orthophosphoric acid (52.5 g) was added to the clear blue vanadium solution at 70° C. over a 15-minute period to give a blue-green solution. Residual reactants were washed into the reaction flask with a minimal amount of water.

2. Preparation of V—Ti—P Catalyst

The 50 wt % titanium(IV) bis(ammonium lactate)dihydroxide solution (109.19 g) was added to a 1-L three-necked kettle reactor equipped with a condenser and a mechanical stirrer. The V/P solution from step 1 above was slowly poured into the Ti solution to give a blue suspension. The V/P flask was rinsed with 30 mL of water and the contents were added to the reaction flask. The mixture was then stirred at 700 to 800 rpm at 130° C. for 16 hours to give a blue to blue-green suspension. The water was then removed via distillation over 4 to 6 hr (oil bath set at 130° C.), and the resulting damp pale green solid was transferred to a ceramic dish and heated in air at 300° C. for 16 hours in a muffle furnace. The resulting solid was then crushed and sieved through an 8×14 mesh. The 8×14 meshed material was then calcined for 6 hours at 450° C. in air (60 SCCM) in a quartz tube furnace to give pale green irregularly shaped pellets. The surface properties and bulk composition of the catalyst prepared in this example are summarized in Table 1.

3. Preparation of Acrylic Acid

The vapor-phase condensation experiment with molar ratio 12 acetic acid/1 trioxane feed was performed at 325° C., 0.083 mL liquid feed/minute, and 80 SCCM $N_2$ for three hours. The performance of the catalyst is summarized in Table 3. In Table 3, the term "Product, g" refers to the mass of the liquid products recovered. The term "Reactants fed, g" includes only those reactants fed as liquids to the reactor: trioxane and acetic acid.

The condensation reaction of acetic acid and trioxane (the formaldehyde source) was performed in a 25-mm outer diameter (21 mm inner diameter) quartz reactor tube with length=61 cm (24 inches). Heat to the reactor was provided by a Barnstead International electric tube furnace (type F21100). Liquid products were collected in a three-necked flask fitted to a water-cooled condenser, which was attached to a dry-ice condenser with a trap. The third neck of the flask was fitted with a stopper which allowed for the addition of a few crystals of hydroquinone inhibitor. Hydroquinone crystals were added at the beginning of the collection of each sample. The base of the receiver flask was fitted with a stopcock to allow for draining of the liquid products.

The quartz reactor had indentations 20 cm (8 inches) up from the base of the tube. The region of the reactor with the indentations was situated near the base of the heated section of the furnace. The reactor was also fitted with a thermowell that extended from the top of the reactor to about an inch below the indentations. The reactor was first loaded with quartz chips to about 2.5 inches in height above the indentations to allow the catalyst to be positioned in the middle of the furnace. The reactor was then loaded with a 5.0 g charge of catalyst. The thermocouple in the thermowell was placed near the center of the catalyst bed. Sufficient quartz chips (about 2.5 inches) were added to the region above the catalyst charge to reach the top of the heated region of the furnace. The performance of this catalyst is summarized in Table 3.

This example illustrates that the TBALDH compound is a suitable precursor for the synthesis of a catalytically active V—Ti—P material, providing acrylic acid in good yield and in high purity under standard screening conditions. The molar composition of the catalyst was nearly identical to that of the catalyst used in Comparative Example 1 below, however the catalyst in Comparative Example 1 has only 60% of the surface area compared to the catalyst of Example 1. The total acid sites were higher for the catalyst of Example 1 as compared to the catalyst of Comparative Example 1; 92.5 (μmol/g) compared to 64.2 (μmol/g), respectively. Powder x-ray diffraction analysis of the catalyst reveals that it is primarily amorphous (FIG. 1).

Comparative Example 1

Preparation of an Amorphous V—Ti—P Catalyst Via Method B and Reactor Screening with an Anhydrous Liquid Feed The catalyst in this example was prepared according to the methods described in M. Ai, *Applied Catalysis*, Vol. 48, pp. 51-61 (1989) and JP 1989-068335A.

1. $Ti(OH)_4$ gel Preparation

A 5-L three-necked round bottomed flask was charged with 300 mL of water ice and 300 mL of deionized water. The flask was fitted with a 125-mL addition funnel and vented to an aqueous saturated sodium bicarbonate solution. Tetrachlorotitanium (34.6 g) was then added slowly to the vigorously stirred water/ice mix. The reactor atmosphere was flushed into the scrubber solution with an air flow to remove gaseous HCl. The pH of the resulting colorless solution was between 0 and 1.

Once the solution warmed to room temperature, it was diluted with 2.5 L of deionized water and the pH was adjusted to between 10 and 11 by the addition of 200 mL of 5.0 M ammonium hydroxide. A bright white solid formed immediately. This material was filtered and washed with 2×1 L of water to give white pieces of a paste-like substance, which was air dried for up to five hours to give a white material with a gel-like consistency.

2. Preparation of V(IV) $H_3PO_4$ Solution

A V/P solution was prepared following the procedure of Example 1, step 1.

3. Preparation of V—Ti—P Catalyst

The hydroxide gel from step 1 above was suspended in 200 mL of water in a 1-L three-necked kettle reactor equipped with a condenser and mechanically stirred at 700 to 800 rpm long enough to obtain a homogeneous white suspension. The V/P solution from step 2 above was slowly poured into the gel suspension to give a blue suspension. The V/P flask was rinsed with 50 mL of water and the contents were added to the reaction flask. The mixture was then stirred at 700 to 800 rpm at 130° C. for 16 hours to give a blue to blue-green suspension.

Figure 2:
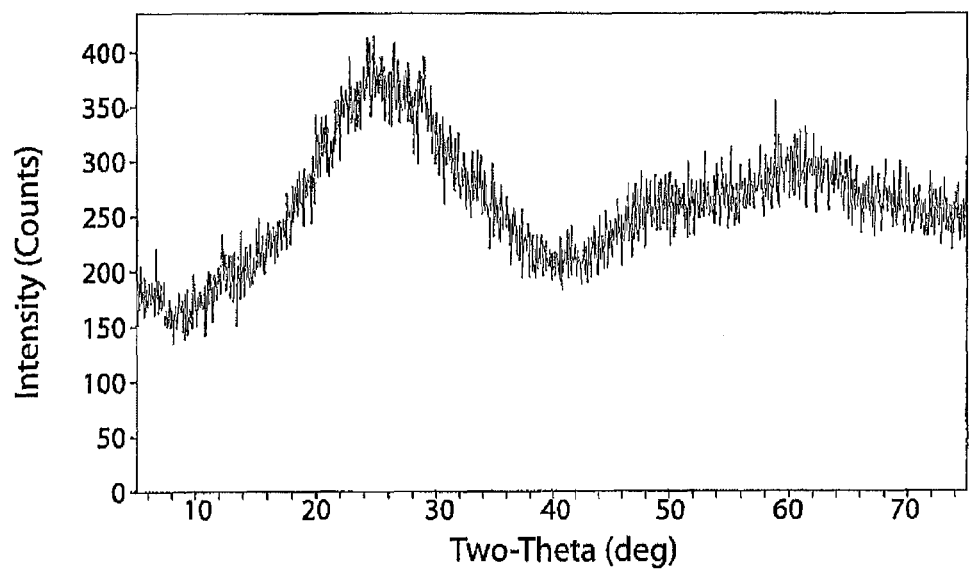
FIG. 2 is a graph showing the X-ray diffraction pattern of the amorphous catalyst prepared via Method B in Comparative Example 1.

The water was then removed via distillation over 6 hr (oil bath set at 130° C.) and the resulting damp pale green solid was transferred to a ceramic dish and heated in air at 300° C. for 16 hours in a muffle furnace. The resulting solid was then crushed and sieved through an 8×14 mesh. The 8×14 meshed material was then calcined for 6 hours at 450° C. in air (60 SCCM) in a quartz tube furnace to give pale green irregularly shaped pellets. The surface properties and bulk composition of the catalyst prepared in this example are summarized in Table 1. Powder X-ray diffraction analysis of the catalyst reveals that it is primarily amorphous (FIG. 2).

4. Preparation of Acrylic Acid

The condensation reaction of acetic acid and trioxane (the formaldehyde source) in this example was performed as described in Example 1 except that a 25-mm outer diameter (21 mm inner diameter) quartz reactor tube with length=107 cm (42 inches) was used. Heat to the reactor was provided by a Lindberg 3-element electric furnace having a heated zone 61 cm (24 inches) in length. Liquid products were collected in a three-necked flask fitted to a water cooled condenser, which was attached to a dry ice condenser with a trap. The third neck of the flask was fitted with a stopper which allowed for the addition of a few crystals of hydroquinone inhibitor. Hydroquinone crystals were added at the beginning of the collection of each sample. The base of the receiver flask was fitted with a stopcock to allow for draining of the liquid products. Liquid samples were collected over a measured time period, weighed, and analyzed by gas chromatography.

The quartz reactor had indentations 30.5 cm (12 inches) up from the base of the tube. The region of the reactor with the indentations was situated near the base of the heated section of the furnace. The reactor was also fitted with a thermowell that extended from the top of the reactor to about an inch below the indentations. The reactor was first loaded with quartz chips to about 10 inches in height above the indentations to allow the catalyst to be positioned in the middle of the 3-element furnace. The reactor was then loaded with a 5.0 g charge of catalyst. The thermocouple in the thermowell was placed 1.5 inches up from the base of the catalyst bed. Sufficient quartz chips were added to the region above the catalyst charge to reach the top of the heated region of the 3-element furnace. The performance of the catalyst is summarized in Table 3.

This example demonstrates that the preparation method according to the prior art was reproducible and that the resulting catalyst performed similarly to the invention catalyst described in Example 1. Under an inert atmosphere and using an anhydrous liquid feed, both catalysts produced acrylic acid in good yield. The acetic acid accountability was nearly identical in both cases. Both catalysts were also amorphous and had a similar bulk composition. Despite these superficial similarities, the microstructure of the catalysts in this example and Example 1 differed considerably as evidenced by the contrast in surface area and acidity measurements.

Comparative Example 2

Preparation of a Mixed Crystalline-Amorphous V—Ti—P Catalyst via Method C and Reactor Screening with an Anhydrous Liquid Feed 1. Preparation of V(IV) $H_3PO_4$ Solution A V/P solution was prepared following the procedure of Example 1, step 1.

2. Preparation of V—Ti—P Catalyst

A 23.38 wt % titanium dioxide colloidal dispersion (41.3 g) and 100 mL of deionized water were added to a 1-L three-necked kettle reactor equipped with a condenser and a mechanical stirrer. The V/P solution from step 1 above was slowly poured into the suspension to give a blue suspension. The V/P flask was rinsed with 25 mL of water and the contents were added to the reaction flask. The mixture was then stirred at 700 to 800 rpm at 130° C. for 16 hours to give a blue-green suspension. The water was then removed via distillation over 6 hr (oil bath set at 130° C.) and the resulting damp pale green solid was transferred to a ceramic dish and heated in air at 300° C. for 16 hours in a muffle furnace. The resulting solid was then crushed and sieved through an 8×14 mesh. The 8×14 meshed material was then calcined for 6 hours at 450° C. in air (60 SCCM) in a quartz tube furnace to give dark grey irregularly shaped pellets. The surface properties and bulk composition of the catalyst prepared in this example are summarized in Table 1. The vapor-phase condensation experiment and the product analysis were carried out as described in Example 1. The performance of the catalyst is summarized in Table 3.

Figure 3:
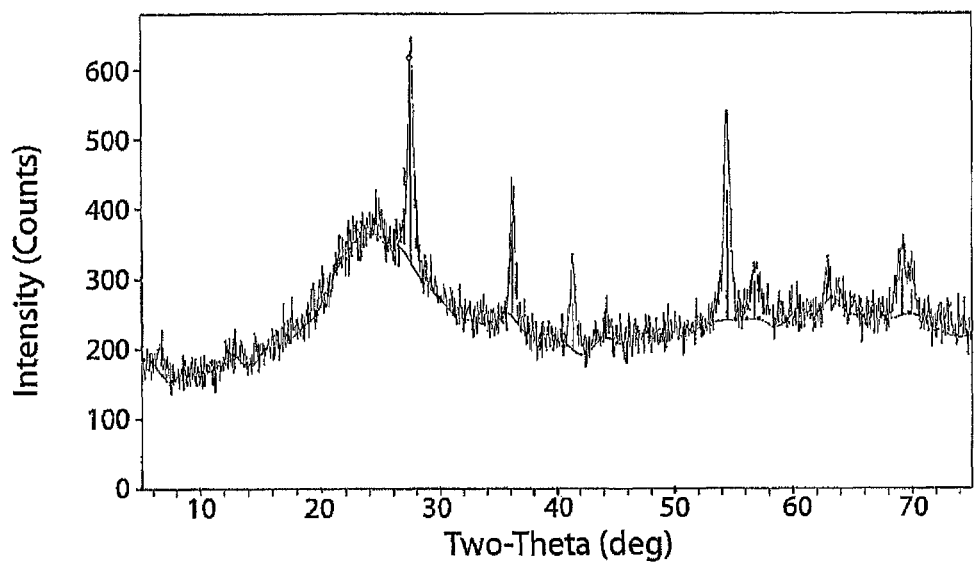
FIG. 3 is a graph showing the X-ray diffraction pattern of the mixed amorphous-crystalline ($TiO_2$) catalyst prepared via Method C in Comparative Example 2.

This example illustrates that titanium dioxide is an unsuitable precursor for preparing a catalytically active V—Ti—P catalyst. Notably, the BET surface area was comparatively low, as were the total acid sites and the overall bulk molar composition, relative to vanadium. This material failed to generate acrylic acid from formaldehyde and acetic acid. Powder X-ray diffraction analysis of the catalyst revealed that it is a mixture of an unknown amorphous material and crystalline rutile (FIG. 3).

Comparative Example 3

Preparation of a Crystalline $VO(HPO)_4(H_2O)_{0.5}$ Catalyst Via Method D and Reactor Screening with an Anhydrous Liquid Feed The catalyst in this example was prepared according to the procedure described in J. K. Bartley et al., "Vanadium Phosphate Catalysts," *Metal Oxide Catalysis*, pp. 499-537 (S. D. Jackson & J. S. J Hargreaves eds. 2009).

Figure 4:
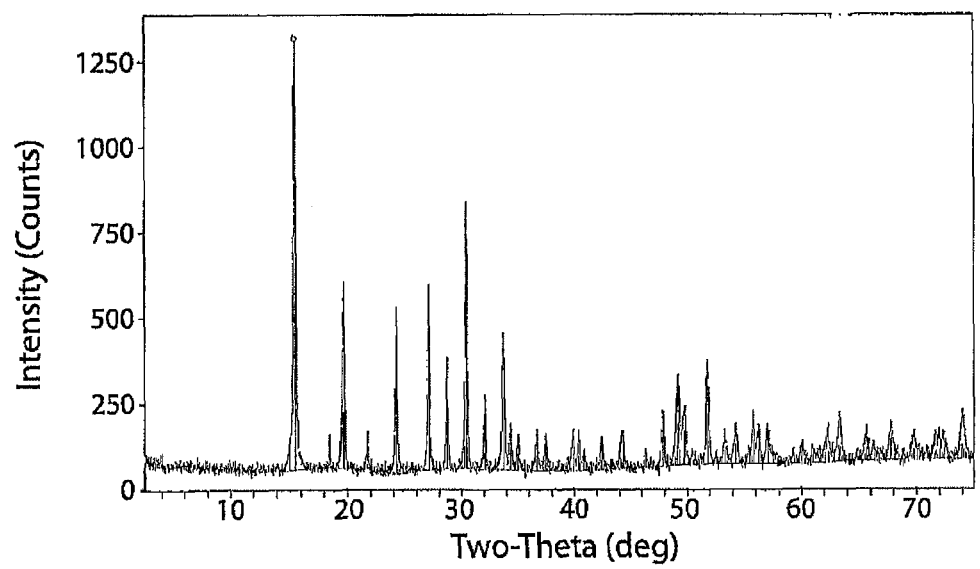
FIG. 4 is a graph showing the X-ray diffraction pattern of the crystalline [$VO(HPO_4)(H_2O)_{0.5}$] catalyst prepared via Method D in Comparative Example 3.

A 1-L kettle reactor equipped with a mechanical stirrer, a condenser, and an addition funnel was charged with 100.08 g of vanadium pentoxide and 600 mL of isobutyl alcohol all under a nitrogen atmosphere. The contents were heated at reflux (oil bath set at 130° C.) for 1 hour, then 139.44 g of 85% phosphoric acid was added slowly, and the reaction temperature was maintained at reflux for 22 hours. The resulting sky blue suspension contained small amounts of dark insoluble materials. Another 5.53 g of 85% phosphoric acid was then added along with an additional 150 mL of iso-butanol. The reflux was then continued for another seven hours. Upon cooling to room temperature, the blue suspension was poured on to a Buchner funnel with filter paper; the heavier insoluble impurities remained in the reaction flask. The blue solid was then isolated by vacuum filtration and washed with 200 mL of ethanol and dried at room temperature while pulling a vacuum. Water soluble impurities were removed by heating a suspension of the blue solid in water to reflux overnight under a nitrogen atmosphere. The mixture was then filtered while still hot, leaving a blue solid on the filter paper and a yellow filtrate in the filter flask. The blue solid was then dried at 110° C. for 22 hours in air to give a blue-green cake. This material was then crushed and sieved through an 8×14 mesh. XRD analysis of this material (FIG. 4) showed it to be crystalline $VO(HPO_4)(H_2O)_{0.5}$. The surface properties and bulk composition of the catalyst prepared in this example are summarized in Table 1. The vapor-phase condensation experiment was carried out according to the description in Example 1. The performance of the catalyst is summarized in Table 4.

This example demonstrates that the catalyst prepared via Method D was not as effective at producing acrylic acid as the invention V—Ti—P catalyst in Example 1 or the V—Ti—P catalyst in Comparative Example 1. As depicted in the XRD pattern, the surface of this catalyst was composed of crystalline vanadyl hydrogen phosphate hemihydrate. This discrete species was not observed from similar XRD analysis of the amorphous catalysts described in either Example 1 or Comparative Example 1.

Comparative Example 4

Preparation of a Crystalline $(VO)_2(P_2O_7)$ Catalyst Via Method E and Reactor Screening with an Anhydrous Liquid Feed The catalyst in this example was prepared according to the procedure described in M. Abon et al., *J. Catalysis*, Vol. 156, pp. 28-36 (1995).

Figure 5:
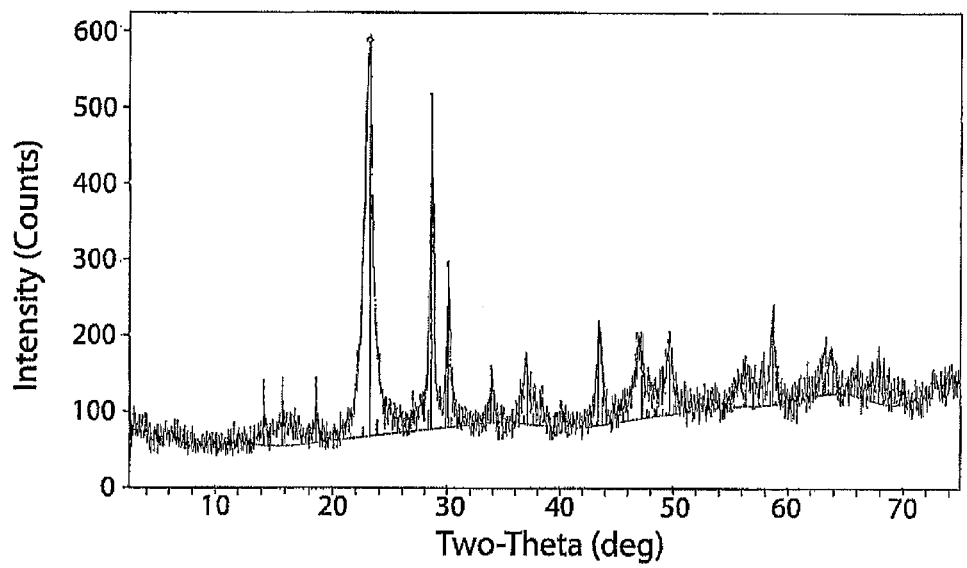
FIG. 5 is a graph showing the X-ray diffraction pattern of the crystalline catalyst [$(VO)_2(P_2O_7)$] prepared via Method E in Comparative Example 4.

Approximately 46 g of the 8×14-mesh $VO(HPO_4)(H_2O)_{0.5}$ prepared in Comparative Example 3 was heated at 500° C. under a 100 SCCM nitrogen flow for 47 hours to give 37.91 g of light brown particles. XRD analysis (FIG. 5) of this material showed it to be crystalline vanadyl pyrophosphate $(VO)_2(P_2O_7)$. The surface properties and bulk composition of the catalyst prepared in this example are summarized in Table 1. The vapor phase condensation experiment was carried out according to the description in Example 1. The performance of the catalyst is summarized in Table 4.

This example demonstrates that this catalyst was not as effective at producing acrylic acid as the invention V—Ti—P catalyst in Example 1 or the V—Ti—P catalyst in Comparative Example 1. As depicted in the XRD pattern, the surface of this catalyst was composed of crystalline vanadyl pyrophosphate. This discrete species was not observed from similar XRD analysis of the amorphous catalysts described in either Example 1 or Comparative Example 1.

Comparative Example 5

Preparation of a Crystalline V—Ti—P—Mo Catalyst Via Method F and Reactor Screening with an Aqueous Liquid Feed The catalyst was prepared according to the procedure described in C. D. Rodica et al., RO 114 084 B1 (1999), except that graphite was not added to the catalyst.

Figure 6:
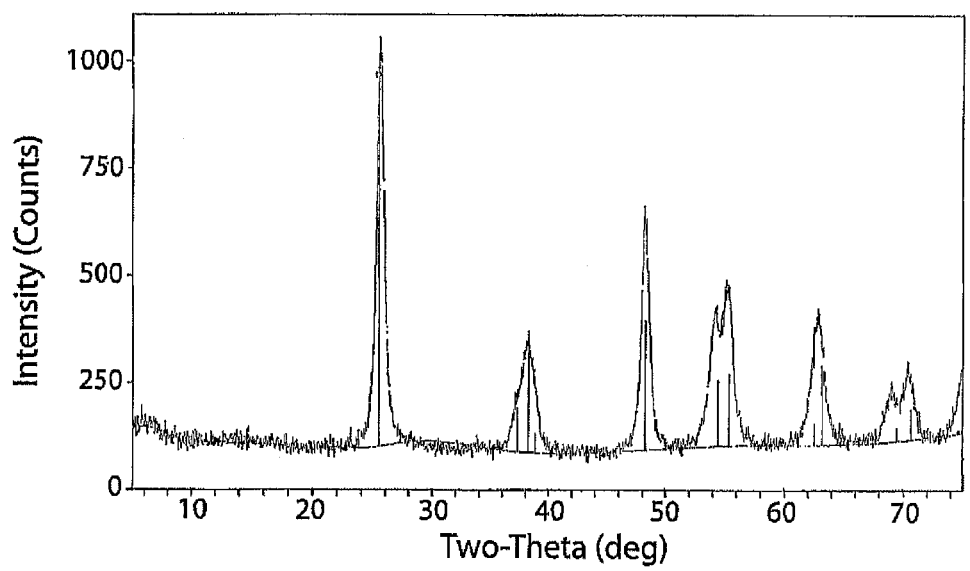
FIG. 6 is a graph showing the X-ray diffraction pattern of the crystalline catalyst ($TiO_2$) prepared via Method F in Comparative Example 5.

Vanadium(V) oxide (3.9 g) was mixed with titanium dioxide (6.65 g), molybdenum(VI) oxide (0.45 g), and 85% phosphoric acid (17 mL) in a ceramic dish to give a thick paste. This material was then dried at 200° C. in a muffle furnace in air for 3 hours to give a hard yellow solid. The solid was then crushed and sieved through an 8×14 mesh. The meshed particles were calcined in a muffle furnace in air at 300° C. for 2 hours. XRD analysis (FIG. 6) of this material showed it to be crystalline titanium dioxide; vanadium and phosphorus components were not observed. The surface properties and bulk composition of the catalyst prepared in this example are summarized in Table 1.

The vapor-phase condensation experiment was carried out as described in Comparative Example 1, except that the reaction conditions were set to those described in RO 114 084 B1. The furnace temperature was set to 350° C., liquid feed rate to 0.025 mL/minute, and nitrogen flow to 51 SCCM. The feed was composed of a 4:0.67:9 molar mixture of acetic acid, trioxane, and water; the run time was 360 minutes. The performance of the catalyst is summarized in Table 4.

This example attempted to reproduce the results disclosed in RO 114 084 B1, which claims an acrylic acid yield of 86.3%. However, the actual yield to acrylic acid was found to be less than one percent. This result, combined with the observation that the catalyst contains crystalline $TiO_2$, provides support for the assertion that titanium dioxide is an unsuitable precursor for preparing active formaldehyde alkanoic acid condensation catalysts.

Example 2

Figure 7:
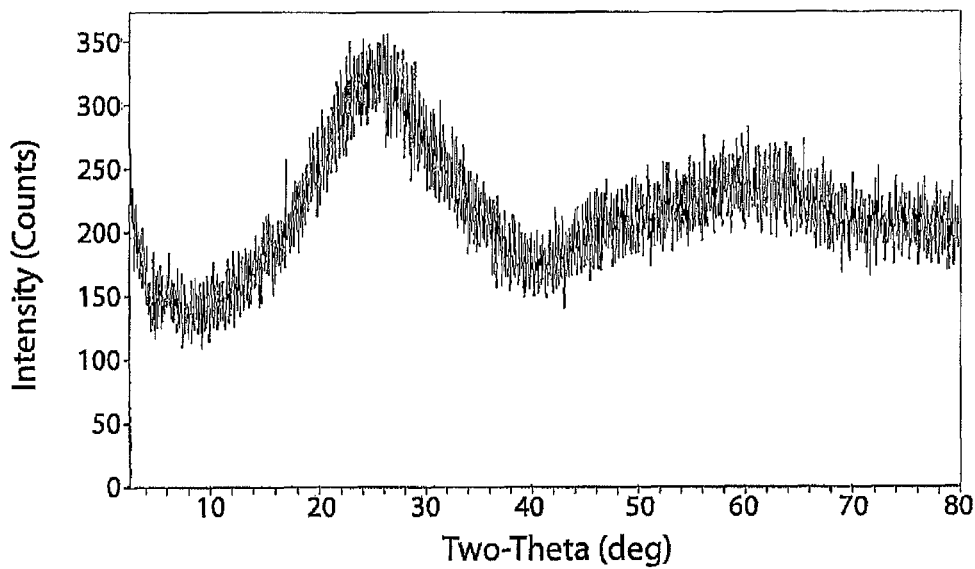
FIG. 7 is a graph showing the X-ray diffraction pattern of the amorphous catalyst prepared via Method G in Example 2.

Preparation of an Amorphous V—Ti—P Catalyst Via Method G and Reactor Screening with an Aqueous Liquid Feed The catalyst in this example was first prepared by suspending ammonium metavanadate (19.54 g) in 218.41 g of a 50 wt % titanium(IV) bis(ammonium lactate)dihydroxide solution followed by addition of 200 mL of deionized water in a 1-L three-neck kettle reactor equipped with a distillation head and a mechanical stirrer. The beige suspension was stirred at 700 rpm for 10 min at room temperature then 105.57 g of 85% phosphoric acid was added followed by a rinse with about 50 mL of water. There was an immediate color change to bright yellow and thickening of the mixture, then a change to green then pale green over 20 min. The suspension was then heated to reflux (oil bath set at 130° C.) and 220 mL of water collected via distillation over three hours. After cooling to room temperature, the resulting pale green semi-solid was scraped into a ceramic dish and calcined at 300° C. for 16 hr in a muffle furnace in air to give black-green solids, which were sieved through an 8×14 mesh. The 8×14 meshed pellets were then calcined at 450° C. in a quartz tube furnace for 6 hr with a 60 SCCM air flow to give pale green pellets. XRD analysis (FIG. 7) of this material showed it to be primarily amorphous. The surface properties and bulk composition of the catalyst prepared in this example are summarized in Table 1.

The condensation reaction of acetic acid and trioxane (the formaldehyde source) in this example was performed as described in Example 1, except that a liquid feed composed of molar ratio 12 acetic acid/1 trioxane/4.09 water was used at 325° C., 0.089 mL liquid feed/minute and the carrier gas, nitrogen, was set at 70 SCCM. The performance of the catalyst is summarized in Table 5.

This example demonstrates that (a) using the water-soluble TBALDH allows for a more rapid catalyst synthesis in that all three catalyst precursors are combined in a one-pot approach and (b) using TBALDH as the titanium source for the V—Ti—P material produces an active catalyst for acrylic acid production, even though lactic acid was absent in the catalyst preparation. The resulting catalyst was amorphous by XRD and has a surface area very similar to the catalyst described in Example 1 and bulk composition very similar to those of the catalysts described in Example 1 and Comparative Example 1.

Comparative Example 6

Figure 8:
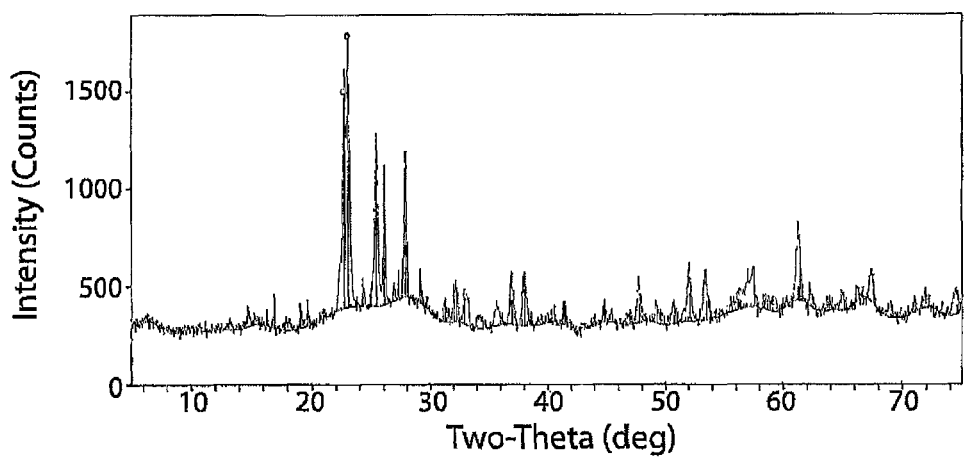
FIG. 8 is a graph showing the X-ray diffraction pattern of the crystalline catalyst [$V(PO_3)_3$ and $Ti(P_2O_7)$] prepared via Method H in Comparative Example 6.

Preparation of a Crystalline V—Ti—P Catalyst Via Method H and Reactor Screening with an Anhydrous Liquid Feed The catalyst in this example was prepared according to the procedure described in Comparative Example 1, except that lactic acid was excluded from the procedure. XRD analysis (FIG. 8) of this material showed it to be a mixture of crystalline vanadium(III) catena-phosphate and titanium diphosphate. The surface properties and bulk composition of the catalyst prepared in this example are summarized in Table 1. The vapor-phase condensation reaction was carried out as described in Example 1. The performance of the catalyst is summarized in performance Table 5.

This example demonstrates that a V—Ti—P material having low acidity and surface area is obtained when tetrachlorotitanium was used as the titanium precursor and lactic acid was excluded during the catalyst synthesis. The surface of the resulting solid was a mixture of crystalline compounds, which evidently displayed poor catalytic activity toward acrylic acid synthesis. The yield was less than 10%, and the selectivity less than 12%. This example also highlights the fact that TBALDH is a more attractive V—Ti—P precursor, since the lactate groups inherent in the salt are sufficient to reduce vanadium during catalyst synthesis, which assists in forming an amorphous surface and creating increased surface area upon calcination.

Example 3

V—Ti—P Catalyst (Method A at 2× Scale) Lifetime Study with an Anhydrous Liquid Feed The catalyst in this example was prepared via Method A (Example 1), but at twice the scale. The condensation reaction of acetic acid and trioxane (the formaldehyde source) in this example was performed as described in Example 1, except that a liquid feed composed of molar ratio 12 acetic acid/1 trioxane was used at 325° C., 0.083 mL liquid feed/minute, and the carrier gases were nitrogen (49 SCCM) and air (21 SCCM). The reaction was run for twenty-seven hours. Also, a 25-mm outer diameter (21 mm inner diameter) quartz reactor tube with length=79 cm (31 inches) was used. Heat to the reactor was provided by an Applied Test Systems series 3210 three-element electric furnace having a heated zone 50 cm (19.5 inches) in length. Liquid products were collected in a three-necked flask fitted with a glycol chilled (0° C.) jacket. The third neck of the flask was connected to a water-cooled condenser, which was connected to a dry ice trap. The base of the receiver flask was fitted with a stopcock to allow for draining of the liquid products.

The quartz reactor had indentations 13 cm (5 inches) up from the base of the tube. The region of the reactor with the indentations was situated near the base of the heated section of the furnace. The reactor was also fitted with a thermowell that extended from the top of the reactor to about an inch below the indentations. The reactor was first loaded with quartz chips to about 8 inches in height above the indentations to allow the catalyst to be positioned in the middle of the 3-element furnace. The reactor was then loaded with a 5.0 g charge of catalyst. The thermocouple in the thermowell was placed 1.5 inches up from the base of the catalyst bed. Sufficient quartz chips were added to the region above the catalyst charge to reach the top of the heated region of the 3-element furnace.

Liquid samples were collected over a measured time period, weighed, and analyzed by gas chromatography and HPLC. Performance of the catalyst is summarized in Table 6.

This example demonstrates that the invention V—Ti—P catalyst prepared with TBALDH afforded acrylic acid in moderate yield and selectivity over a twenty-seven hour period. The presence of oxygen contributed to an extended catalyst lifetime. As a consequence of using an anhydrous liquid feed, high coking rates are suspected to have caused the decreased yield observed in the last data point.

Comparative Example 7

V—Ti—P Catalyst (Method B at 2× Scale) Lifetime Study with an Anhydrous Liquid Feed The catalyst in this example was prepared via Method B (Comparative Example 1), but at twice the scale. The vapor-phase condensation experiment was carried out as described in Example 3. The performance of the catalyst is summarized in Table 7.

This example demonstrates that the V—Ti—P catalyst prepared according to the prior art performed similarly to the invention catalyst when an anhydrous liquid feed was employed over a twenty-seven hour period. Again, the decreased yield observed in the third data point is attributed to a high rate of coking.

Example 4

V—Ti—P Catalyst (Method a at 2× Scale) Lifetime Study with an Aqueous Liquid Feed The catalyst used in this example was the same catalyst charge used in Example 3, except that it was regenerated after that example by heating at 400° C. under 6 vol % oxygen (94 vol % nitrogen) for 16 hours. The vapor-phase condensation reaction was then carried out according to Example 3, except that a liquid feed composed of molar ratio 12 acetic acid/1 trioxane/4.09 water was used at 325° C., 0.089 mL liquid feed/minute. The carrier gases were nitrogen (49 SCCM) and air (21 SCCM). The reaction was run for twenty-seven hours. The performance of the catalyst is summarized in Table 8.

This example demonstrates that the V—Ti—P catalyst prepared with TBALDH maintained (1) a very high selectivity toward acrylic acid when an aqueous liquid feed was used and (2) a consistent moderate yield. The final yield of nearly 55% is comparatively higher than the same point in Example 3, presumably due to a lower rate of coking.

Comparative Example 8

V—Ti—P Catalyst (Method B at 2× Scale) Lifetime Study with an Aqueous Liquid Feed The catalyst used in this example was the same catalyst charge used in Comparative Example 7, except that it was regenerated after that example by heating at 400° C. under 6 vol % oxygen (94 vol % nitrogen) for 16 hours. The vapor-phase condensation reaction was then carried out according to Example 3, except that a liquid feed composed of molar ratio 12 acetic acid/1 trioxane/4.09 water was used at 325° C., 0.089 mL liquid feed/minute. The carrier gases were nitrogen (49 SCCM) and air (21 SCCM). The reaction was run for twenty-seven hours. The performance of the catalyst is summarized in Table 9.

This example demonstrates that the V—Ti—P catalyst prepared according to the prior art did not afford acrylic acid in as high a yield as the invention catalyst when an aqueous liquid feed was used. Even though the selectivity toward acrylic acid was similarly high and the reaction lifetime was comparable, the formaldehyde conversion was consistently lower than observed in Example 4 by more than twenty percent. This is surprising given that both V—Ti—P catalysts demonstrated similar activity and selectivity when the anhydrous liquid feed was used.

Example 5

Preparation of an Amorphous V—Ti—P Catalyst Using Anti-Solvent Via Method I and Reactor Screening with an Aqueous Liquid Feed The catalyst used in this example was prepared by first suspending ammonium metavanadate (19.65 g) in 218.54 g of a 50 wt % titanium(IV) bis(ammonium lactate)dihydroxide solution followed by addition of 150 mL of deionized water in a 1-L three-neck kettle reactor equipped with a reflux condenser and a mechanical stirrer. The beige suspension was stirred at 700 rpm for 10 min at room temperature. Then 105.06 g of 85% phosphoric acid were added slowly followed by a rinse with 50 mL of deionized water. There was an immediate color change to bright yellow, then a change to green then pale green over 20 min. The suspension was then heated to reflux for one hour, after which no further color change was observed. The reactor was cooled to about 6° C. in an ice-water bath, and 700 to 800 mL of absolute ethanol was added, causing the mixture to thicken. The contents were stirred for 20 min at 6° C. and the solids were collected on a medium porosity frit while pulling a vacuum. The emerald green filtrate (405.28 g) was collected and subjected to elemental analysis.

The filtered solid was allowed to air dry while pulling a vacuum on the frit to give a pale green powder. The powder was calcined initially by heating at 300° C. for 16 hr in a muffle furnace in air to give grey-green solids. The solids were then sieved through an 8×14 mesh. The 8×14 meshed pellets were then calcined at 450° C. in a quartz tube furnace for 6 hr with a 60 SCCM air flow to give pale green irregularly shaped pellets.

Figure 9:
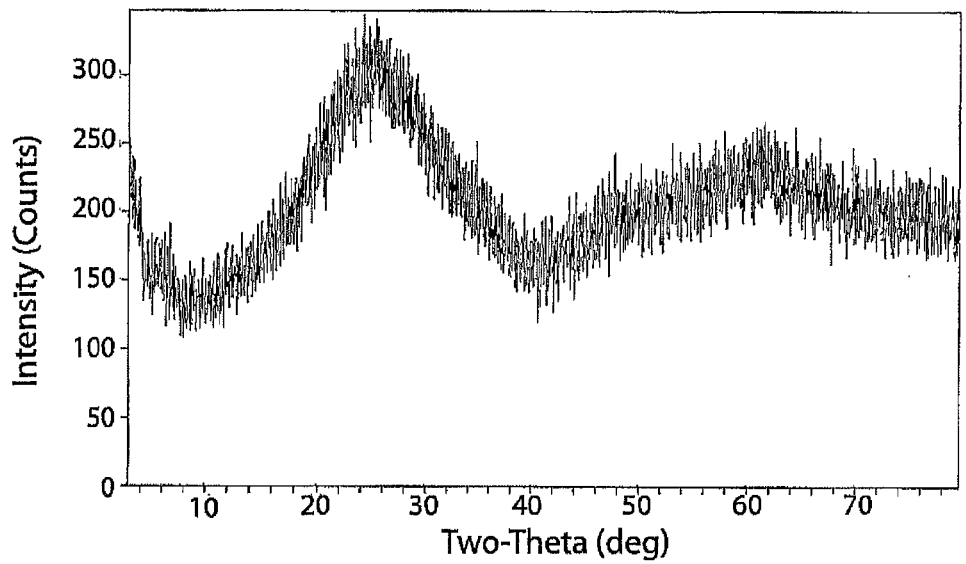
FIG. 9 is a graph showing the X-ray diffraction pattern of the amorphous catalyst prepared via Method I in Example 5.

The X-ray diffraction pattern (FIG. 9) shows that the catalyst is primarily amorphous. The surface properties and bulk composition of the catalyst prepared in this example are summarized in Table 1. The percent vanadium, titanium, and phosphorus lost in the filtrate are summarized in Table 2. The vapor-phase condensation experiment was performed according to Example 4. The performance of the catalyst is summarized in Table 10.

This example demonstrates that the V—Ti—P material obtained by precipitation from ethanol effectively catalyzed the condensation of formaldehyde with acetic acid to form acrylic acid. Specifically, the catalyst maintained a formaldehyde conversion of around 78% after 27 hours and a product selectivity of approximately 80% after the same time period. Only 7 wt % of the vanadium components and 15.5 wt % of the phosphorus components were lost as a result of filtration.

Example 6

Preparation of an Amorphous V—Ti—P Catalyst without Anti-Solvent Via Method J and Reactor Screening with an Aqueous Liquid Feed The catalyst used in this example was prepared by first suspending ammonium metavanadate (19.52 g) in 218.34 g of a 50 wt % titanium(IV) bis(ammonium lactate)dihydroxide solution followed by addition of 150 mL of deionized water in a 1-L three-neck kettle reactor equipped with a reflux condenser and a mechanical stirrer. The beige suspension was stirred at 700 rpm for 10 min at room temperature. Then 105.32 g of 85% phosphoric acid were added slowly followed by a rinse with 50 mL of deionized water. There was an immediate color change to bright yellow, then a change to green then pale green over 20 min. The suspension was then heated to reflux for one hour, after which no further color change was observed. The reactor was cooled to about 6° C. in an ice-water bath and 800 mL of deionized water were added. The contents were stirred for 20 min at 6° C. and the solids were collected on a medium porosity frit while pulling a vacuum. The deep blue filtrate (459.9 g) was collected and subjected to elemental analysis.

The filtered solid was allowed to air dry while pulling a vacuum on the frit to give a pale green powder that was calcined initially by heating at 300° C. for 16 hr in a muffle furnace in air to give grey-green solids. The solids were then sieved through an 8×14 mesh. The 8×14 meshed pellets were then calcined at 450° C. in a quartz tube furnace for 6 hr with a 60 SCCM air flow to give yellow irregularly shaped pellets.

Figure 10:
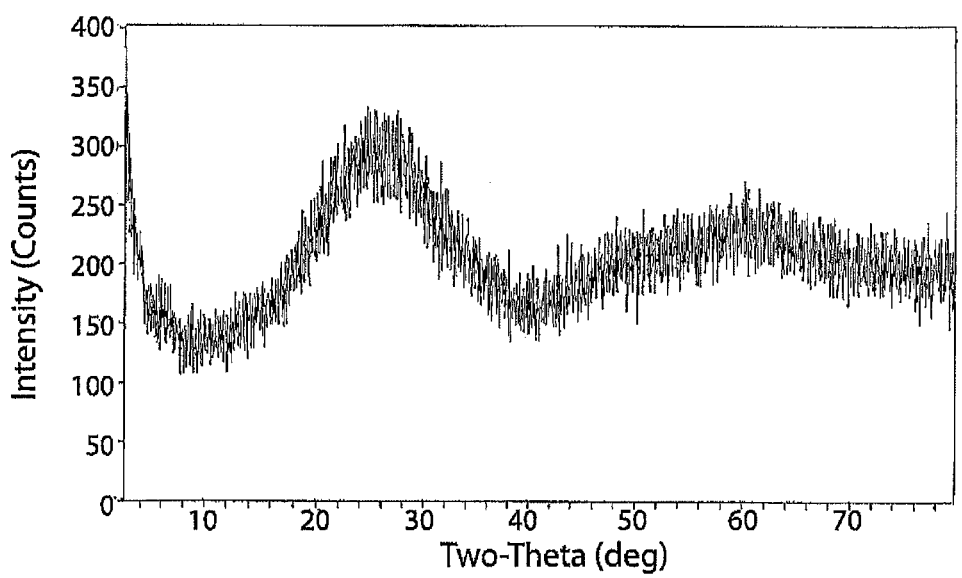
FIG. 10 is a graph showing the X-ray diffraction pattern of the amorphous catalyst prepared via Method J in Example 6.

The X-ray diffraction pattern (FIG. 10) shows that the catalyst was primarily amorphous. The surface properties and bulk composition of the catalyst prepared in this example are summarized in Table 1. The percent vanadium, titanium, and phosphorus lost in the filtrate are summarized in Table 2. The vapor-phase condensation experiment was carried out as described in Example 4. The performance of the catalyst is summarized in Table 11.

This example demonstrates that isolating the V—Ti—P catalyst by filtration in the absence of an anti-solvent such as ethanol led to a material with a relatively high titanium content and a loss of nearly 36 wt % of both the vanadium and phosphorus components. Moreover, the resulting material did not carry out the condensation reaction as effectively as the V—Ti—P material in Example 5. For example, although the formaldehyde conversion was initially high (>90%), the selectivity to acrylic acid was comparatively low (approximately 59% after a 27-hour period). Moreover, the yield of this reaction at 27 hours was about twenty percent lower than that of Example 5.

A summary of the XRD measurements for the catalysts produced is given below.

Semi-Crystalline Catalysts:

| Example No. | Crystalline Phase Identified | Calculated Weight % of Phase from Rietveld Method | Estimated Crystallite Size of Phase (Å) |
| --- | --- | --- | --- |
| Comp. Ex. 2 (FIG. 3) | Rutile Titanium dioxide ($TiO_2$) | 21 | 191 |
| Comp. Ex. 3 (FIG. 4) | Vanadyl Hydrogenphosphate Hemihydrate | 96 | 723 |
| Comp. Ex. 4 (FIG. 5) | Bis(oxovandium) Diphosphate | 94 | 198 |
| Comp. Ex. 5 (FIG. 6) | Titanium Dioxide | 97 | 116 |
| Comp. Ex. 6 (FIG. 8) | Vanadium (III) Catena $V(PO_3)_3$ | 34 | 670 |
| | Titanium Diphosphate(V) - $Ti(P_2O_7)$ | 66 | 424 |

Amorphous Catalysts:

| Example No. | 2-Theta Peak Locations | | | | Relative Area | | | | Estimated Crystallite Size (Å) | |
|---|---|---|---|---|---|---|---|---|---|---|
| Ex. 1 (FIG. 1) | 26.0 | 59.3 | | | 100 | 58 | | | <30 | <30 |
| Ex. 2 (FIG. 7) | 25.6 | 60.2 | | | 100 | 61 | | | <30 | <30 |
| Ex. 5 (FIG. 9) | 25.3 | 61.4 | | | 100 | 82 | | | <30 | <30 |
| Comp. Ex. 1 (FIG. 2) | 25.6 | 59.2 | | | 100 | 57 | | | <30 | <30 |
| Ex. 6 (FIG. 10) | 25.7 | 60.2 | | | 100 | 86 | | | <30 | <30 |

TABLE 1

| Example | Catalyst Descriptor | BET Surface Area (m²/g) | Iso-Propanol TPD Total Acid Sites (μmol/g) | XRD | Mole Ratio Bulk Composition (via XRF) |
|---|---|---|---|---|---|
| Ex. 1 | V—Ti—P (Method A) | 55 | 92.5 | Amorphous | 1.00V:1.92Ti:5.34P |
| Comp. Ex. 1 | V—Ti—P (Method B) | 34 | 64.2 | Amorphous | 1.00V:1.89Ti:5.29P |
| Comp. Ex. 2 | V—Ti—P (Method C) | 1.7 | 2.8 | Rutile | 1.00V:1.07Ti:3.03P |
| Comp. Ex. 3 | V—P (Method D) | 7 | 6.8 | VO(HPO$_4$)(H$_2$O)$_{0.5}$ | 1.00V:0.96P |
| Comp. Ex. 4 | V—P (Method E) | 21 | 17.6 | (VO)$_2$(P$_2$O$_7$) | 1.00V:1.00P |
| Comp. Ex. 5 | V—Ti—P—Mo (Method F) | 73 | 89.4 | TiO$_2$ | n/a |
| Ex. 2 | V—Ti—P (Method G) | 55 | n/a | Amorphous | 1.00V:2.00Ti:5.33P |
| Comp. Ex. 6 | V—Ti—P (Method H) | 5.3 | 13.6 | V(PO$_3$)$_3$ and Ti(P$_2$O$_7$) | 1.00V:1.78Ti:5.22P |
| Ex. 5 | V—Ti—P (Method I) | 46 | 84.5 | Amorphous | 1.00V:1.94Ti:4.92P |
| Ex. 6 | V—Ti—P (Method J) | 78 | 143.4 | Amorphous | 1.00V:2.61Ti:4.58P |

TABLE 2

| | Example 5 | Example 6 |
|---|---|---|
| Catalyst Descriptor | V—Ti—P (Method I) | V—Ti—P (Method J) |
| Vanadium in precursor (g) | 8.56 | 8.5 |
| Titanium in precursor (g) | 17.78 | 17.77 |
| Phosphorus in precursor (g) | 28.23 | 28.3 |
| Vanadium in filtrate (g), measured via XRF | 0.6 | 3.054 |
| Titanium in filtrate (g), measured via XRF | 0.002 | 0.056 |
| Phosphorus in filtrate (g), measured via XRF | 4.377 | 10.256 |
| Wt Percent vanadium lost in catalyst synthesis | 7.0 | 35.9 |
| Wt Percent titanium lost in catalyst synthesis | 0.0 | 0.3 |
| Wt Percent phosphorus lost in catalyst synthesis | 15.5 | 36.2 |

TABLE 3

| | Example 1 | Comp. Example 1 | Comp. Example 2 |
|---|---|---|---|
| Catalyst Descriptor | V—Ti—P (Method A) | V—Ti—P (Method B) | V—Ti—P (Method C) |
| Furnace temperature (° C.) | 325 | 325 | 325 |
| Reaction time (min.) | 180 | 180 | 180 |
| Nitrogen flow rate (SCCM) | 80 | 80 | 80 |
| Liquid feed molar ratio (HOAc/Trioxane) | 12/1 | 12/1 | 12/1 |
| Liquid feed rate (mL/min) | 0.083 | 0.083 | 0.083 |
| Product, g | 14.4 | 14.083 | 13.53 |
| Reactants fed, g | 15.84 | 15.84 | 15.84 |
| GC Results | | | |
| Acetone, wt % | 0.16 | 0 | 0 |
| MeOAc, wt % | 0.11 | 0 | 0 |
| Water, wt % | 6.96 | 5.99 | 0.52 |
| HOAc, wt % | 70.71 | 70.14 | 87.1 |
| Acrylic acid, wt % | 18.75 | 20.07 | 0 |
| HOPr, wt % | 0 | 0.06 | 0 |
| Total knowns, wt % | 96.73 | 96.26 | 87.62 |
| Key Metrics | | | |
| % yield acrylic acid from H2CO | 64.35 | 68.06 | 0.00 |
| total mole acrylates/kg-hr | 2.5 | 2.66 | 0.00 |
| mole ratio AA/acetone | 94.45 | 182.78 | 0.00 |
| % HOAc accountability | 88.68 | 88.01 | 83.72 |

TABLE 4

| | Comp. Example 3 | Comp. Example 4 | Comp. Example 5 |
|---|---|---|---|
| Catalyst Descriptor | V—P (Method D) | V—P (Method E) | V—Ti—P—Mo (Method F) |
| Furnace temperature (° C.) | 325 | 325 | 350 |
| Reaction time (min.) | 180 | 180 | 360 |
| Nitrogen flow rate (SCCM) | 80 | 80 | 51 |
| Liquid feed molar ratio (HOAc/Trioxane/H2O) | 12/1/0 | 12/1/0 | 4/0.67/9 |
| Liquid feed rate (mL/min) | 0.083 | 0.083 | 0.025 |
| Product, g | 13.62 | 14.29 | 8.61 |
| Reactants fed, g | 15.84 | 15.84 | 9.7 |

TABLE 4-continued

|  | Comp. Example 3 | Comp. Example 4 | Comp. Example 5 |
|---|---|---|---|
| GC Results |  |  |  |
| Acetone, wt % |  | 0.06 |  |
| MeOAc, wt % |  |  | 0.11 |
| Water, wt % | 2.67 | 4.13 | 33.87 |
| HOAc, wt % | 73.91 | 75.79 | 52.08 |
| Acrylic acid, wt % | 4.89 | 13.32 | 0.49 |
| HOPr, wt % |  |  |  |
| Total knowns, wt % | 87.83 | 99.19 | 86.55 |
| Key Metrics |  |  |  |
| % yield acrylic acid from $H_2CO$ | 15.87 | 45.37 | 1.4 |
| total mole acrylates/kg-hr | 0.62 | 1.76 | 0.02 |
| mole ratio AA/acetone |  |  |  |
| % HOAc accountability | 75.39 | 88.26 | 63.4 |

TABLE 5

|  | Example 2 | Comparative Example 6 |
|---|---|---|
| Catalyst Descriptor | V—Ti—P (Method G) | V—Ti—P (Method H) |
| Nitrogen flow rate (SCCM) | 70 | 80 |
| Liquid feed molar ratio (HOAc/Trioxane/H2O) | 12/1/4.09 | 12/1/0 |
| Liquid feed rate (mL/min) | 0.089 | 0.083 |
| Product, g | 14.45 | 10.08 |
| Reactants fed, g | 16.19 | 15.84 |
| GC/HPLC Results |  |  |
| Formaldehyde, wt % | 2.68 | 5.71 |
| Acetone, wt % | 0.013 | 0.29 |
| MeOAc, wt % | 0.031 |  |
| Water, wt % | 13.06 | 1.28 |
| HOAc, wt % | 72.21 | 89.33 |
| Acrylic acid, wt % | 17.33 | 3.18 |
| HOPr, wt % |  |  |
| Total knowns, wt % | 105.32 | 99.79 |
| Key Metrics |  |  |
| % H2CO conversion | 77.84 | 67.08 |
| % selectivity to acrylic acid from H2CO | 76.74 | 11.39 |
| % yield acrylic acid from H2CO | 59.73 | 7.64 |
| % HOAc accountability | 89.69 | 66.24 |
| mole acrylic acid/kg-hr | 2.32 | 0.3 |

TABLE 6

|  | Example 3 | | |
|---|---|---|---|
| Catalyst Descriptor | V—Ti—P, Method A (2X Scale) | | |
| Liquid feed molar ratio (HOAc/Trioxane) | 12/1 | | |
| Liquid feed flow rate (mL/min) | 0.083 | | |
| Nitrogen flow rate (SCCM) | 49 | | |
| Air flow rate (SCCM) | 21 | | |
| Time between samples (h) | 1.0 | 3.0 | 23 |
| Total run time (h) | 1.0 | 4.0 | 27 |
| Product, g | 4.37 | 15.19 | 116.2 |
| Reactants fed, g | 5.24 | 15.84 | 121.41 |
| GC/HPLC Results |  |  |  |
| Formaldehyde, wt % | 2.33 | 3.21 | 5.31 |
| Acetone, wt % | 0.195 | 0.23 | 0.227 |
| MeOAc, wt % | 0.084 | 0.073 | 0.092 |
| Water, wt % | 7.57 | 6.53 | 4.58 |
| HOAc, wt % | 68.34 | 69.98 | 76.33 |
| Acrylic acid, wt % | 17.53 | 15.97 | 10.27 |
| HOPr, wt % |  | 0.035 | 0.047 |
| Total knowns, wt % | 96.05 | 96.03 | 96.85 |
| Key Metrics |  |  |  |
| % H2CO conversion | 82.54 | 72.31 | 54.28 |
| % selectivity to acrylic acid from H2CO | 66.35 | 79.38 | 67.88 |
| % yield acrylic acid from H2CO | 54.76 | 57.40 | 36.85 |
| % HOAc accountability | 78.19 | 90.42 | 91.99 |
| mole acrylic acid/kg-hr | 2.14 | 2.24 | 1.44 |

TABLE 7

|  | Comparative Example 7 | | |
|---|---|---|---|
| Catalyst Descriptor | V—Ti—P, Method B (2X Scale) | | |
| Liquid feed molar ratio (HOAc/Trioxane) | 12/1 | | |
| Liquid feed flow rate (mL/min) | 0.083 | | |
| Nitrogen flow rate (SCCM) | 49 | | |
| Air flow rate (SCCM) | 21 | | |
| Time between samples (h) | 1.0 | 3.0 | 23 |
| Total run time (h) | 1.0 | 4.0 | 27 |
| Product, g | 4.85 | 15.48 | 119.01 |
| Reactants fed, g | 5.39 | 15.77 | 121.46 |
| GC/HPLC Results |  |  |  |
| Formaldehyde, wt % | 3.94 | 3.28 | 5.64 |
| Acetone, wt % | 0.08 | 0.18 | 0.24 |
| MeOAc, wt % | 0.08 |  |  |
| Water, wt % | 8.7 | 5.49 | 3.28 |
| HOAc, wt % | 68.67 | 71.21 | 78.05 |
| Acrylic acid, wt % | 15.36 | 17.86 | 11.07 |
| HOPr, wt % |  |  |  |
| Total knowns, wt % | 96.83 | 98.02 | 98.28 |
| Key Metrics |  |  |  |
| % H2CO conversion | 68.12 | 71.04 | 50.29 |
| % selectivity to acrylic acid from H2CO | 76.05 | 92.50 | 80.87 |
| % yield acrylic acid from H2CO | 51.80 | 65.71 | 40.66 |
| % HOAc accountability | 82.68 | 95.47 | 96.75 |
| mole acrylic acid/kg-hr | 2.02 | 2.57 | 1.59 |

TABLE 8

|  | Example 4 | | |
|---|---|---|---|
| Catalyst Descriptor | V—Ti—P, Method A (2X Scale) | | |
| Liquid feed molar ratio (HOAc/Trioxane/H2O) | 12/1/4.09 | | |
| Liquid feed rate (mL/min) | 0.089 | | |
| Nitrogen flow rate (SCCM) | 49 | | |
| Air flow rate (SCCM) | 21 | | |
| Time between samples (h) | 1.0 | 3.0 | 23.1 |
| Total run time (h) | 1.0 | 4.0 | 27.1 |
| Product, g | 5.34 | 16.70 | 130.42 |
| Reactants fed, g | 5.835 | 17.079 | 131.680 |
| GC/HPLC Results |  |  |  |
| Formaldehyde, wt % | 4.18 | 4.47 | 4.72 |
| Acetone, wt % | 0.073 | 0.096 | 0.096 |
| MeOAc, wt % | 0.184 | 0.195 | 0.206 |
| Water, wt % | 17.15 | 13.44 | 12.56 |
| HOAc, wt % | 66.14 | 70.01 | 69.44 |
| Acrylic acid, wt % | 12.84 | 13.68 | 13.57 |
| HOPr, wt % | 0.016 | 0.005 | 0.005 |
| Total knowns, wt % | 100.58 | 101.90 | 100.60 |
| Key Metrics |  |  |  |
| % H2CO conversion | 62.49 | 57.14 | 54.15 |
| % selectivity to acrylic acid from H2CO | 76.85 | 95.67 | 101.43 |
| % yield acrylic acid from H2CO | 48.02 | 54.67 | 54.93 |
| % HOAc accountability | 86.62 | 98.10 | 98.58 |
| mole acrylic acid/kg-hr | 1.86 | 2.12 | 2.13 |

TABLE 9

| | Comparative Example 8 | | |
|---|---|---|---|
| Catalyst Descriptor | V—Ti—P, Method B (2X Scale) | | |
| Liquid feed molar ratio (HOAc/Trioxane/H2O) | 12/1/4.09 | | |
| Liquid feed flow rate (mL/min) | 0.089 | | |
| Nitrogen flow rate (SCCM) | 49 | | |
| Air flow rate (SCCM) | 21 | | |
| Time between samples (h) | 1.0 | 3.0 | 23 |
| Total reaction time (h) | 1.0 | 4.0 | 27 |
| Product, g | 5.42 | 16.72 | 130.91 |
| Reactants fed, g | 5.762 | 17.1 | 131.39 |
| GC/HPLC Results | | | |
| Formaldehyde, wt % | 6.61 | 6.87 | 6.78 |
| Acetone, wt % | 0.068 | 0.063 | 0.065 |
| MeOAc, wt % | | | |
| Water, wt % | 8.83 | 8.96 | 9.15 |
| HOAc, wt % | 72.59 | 73.16 | 72.15 |
| Acrylic acid, wt % | 8.68 | 8.35 | 8.98 |
| HOPr, wt % | | | |
| Total knowns, wt % | 96.85 | 97.4 | 97.12 |
| Key Metrics | | | |
| % H2CO conversion | 39.03 | 34.13 | 33.75 |
| % selectivity to acrylic acid from H2CO | 85.49 | 97.78 | 108.32 |
| % yield acrylic acid from H2CO | 33.37 | 33.37 | 36.56 |
| % HOAc accountability | 92.36 | 96.28 | 97.52 |
| mole acrylic acid/kg-hr | 1.29 | 1.29 | 1.42 |

TABLE 10

| | Example 5 | | |
|---|---|---|---|
| Catalyst Descriptor | V—Ti—P, Method I | | |
| Liquid feed molar ratio (HOAc/Trioxane/H2O) | 12/1/4.09 | | |
| Liquid feed rate (mL/min) | 0.089 | | |
| Nitrogen flow rate (SCCM) | 49 | | |
| Air flow rate (SCCM) | 21 | | |
| Time between samples (h) | 1.0 | 3.0 | 23.1 |
| Total run time (h) | 1.0 | 4.0 | 27.1 |
| Product, g | 4.85 | 16.06 | 128.97 |
| Reactants fed, g | 5.71 | 17.14 | 132.12 |
| GC/HPLC Results | | | |
| Formaldehyde, wt % | 1.88 | 2.12 | 2.31 |
| Acetone, wt % | 0.076 | 0.068 | 0.062 |
| MeOAc, wt % | 0.131 | 0.102 | 0.092 |
| Water, wt % | 16.51 | 15.72 | 15.52 |
| HOAc, wt % | 67.38 | 65.84 | 66.89 |
| Acrylic acid, wt % | 16.76 | 16.84 | 15.57 |
| HOPr, wt % | | 0.012 | 0.012 |
| Total knowns, wt % | 102.74 | 100.70 | 100.46 |
| Key Metrics | | | |
| % H2CO conversion | 84.35 | 80.52 | 77.89 |
| % selectivity to acrylic acid from H2CO | 68.93 | 80.09 | 79.75 |
| % yield acrylic acid from H2CO | 58.15 | 64.49 | 62.12 |
| % HOAc accountability | 85.01 | 92.09 | 95.91 |
| mole acrylic acid/kg-hr | 2.26 | 2.50 | 2.41 |

TABLE 11

| | Example 6 | | |
|---|---|---|---|
| Catalyst Descriptor | V—Ti—P, Method J | | |
| Liquid feed molar ratio (HOAc/Trioxane/H2O) | 12/1/4.09 | | |
| Liquid feed rate (mL/min) | 0.089 | | |
| Nitrogen flow rate (SCCM) | 49 | | |
| Air flow rate (SCCM) | 21 | | |
| Time between samples (h) | 1.0 | 3.0 | 23.0 |
| Total run time (h) | 1.0 | 4.0 | 27.0 |
| Product, g | 4.75 | 16.21 | 126.52 |
| Reactants fed, g | 5.69 | 17.12 | 131.40 |
| GC/HPLC Results | | | |
| Formaldehyde, wt % | 0.889 | 0.917 | 3.27 |
| Acetone, wt % | 0.023 | 0.024 | 0.035 |
| MeOAc, wt % | 0.143 | 0.154 | 0.184 |
| Water, wt % | 19.89 | 16.97 | 15.27 |
| HOAc, wt % | 65.42 | 68.77 | 72.24 |
| Acrylic acid, wt % | 14.86 | 13.69 | 10.34 |
| HOPr, wt % | 0.026 | 0.064 | 0.065 |
| Total knowns, wt % | 101.25 | 100.58 | 101.40 |
| Key Metrics | | | |
| % H2CO conversion | 92.72 | 91.48 | 69.12 |
| % selectivity to acrylic acid from H2CO | 54.71 | 57.92 | 58.86 |
| % yield acrylic acid from H2CO | 50.72 | 52.99 | 40.68 |
| % HOAc accountability | 79.90 | 93.38 | 95.79 |
| mole acrylic acid/kg-hr | 1.97 | 2.06 | 1.58 |

Condensation Reaction for Examples 7-9

The catalyst used in these examples was a 5.0 g charge obtained from the invention catalyst batch described in Example 3. The vapor phase condensation reactions were carried out as described in Example 3. The space velocities were varied in Examples 7 and 8, but the molar ratios of the feed components remained constant. Counting trioxane as three formaldehyde equivalents and inerts as being nitrogen plus air components other than oxygen, the molar ratios of the feed components acetic acid/formaldehyde/water/inerts/oxygen were 1.31/0.33/0.45/2.93/0.19.

Samples were taken after 16.02 mL (17.3 g) of the liquid had been fed in order to minimize any effects due to possible reactant induced catalyst deactivation. Then the samples were weighed and analyzed. The last sample was taken 1 hour after the liquid feed was stopped. Generally, three samples were taken at each set of conditions, and the results are presented as an average of the results from the samples collected at each set of conditions. The results are summarized in Table 12 below. After the reaction at a given set of conditions was completed, the catalyst was regenerated by subjecting to 10 SCCM nitrogen plus 20.8 SCCM air at 405° C. overnight.

Example 7

This example illustrates the invention performed in the lower space velocity region of the preferred range. The 1.31/0.33/0.45/2.93/0.19 molar ratio of acetic acid/formaldehyde/water/inerts/oxygen mixture was delivered to the reactor under the conditions described above at a space velocity of 60 moles of all feed components/kg-hr. The reaction evolved heat, and the catalyst bed temperature during this run was 339.5° C. The results are summarized in Table 12 below.

Example 8

This example illustrates the invention performed in the most preferred space velocity region. The 1.31/0.33/0.45/2.93/0.19 molar ratio of acetic acid/formaldehyde/water/inerts/oxygen mixture was delivered to the reactor under the conditions described above at a space velocity of 138 moles of all feed components/kg-hr. The reaction evolved heat, and the catalyst bed temperature during this run was 352.9° C. The results are summarized in Table 12 below.

Example 9

This example was performed at a low space velocity value outside of the preferred range of the invention. The 1.31/0.33/0.45/2.93/0.19 molar ratio of acetic acid/formaldehyde/water/inerts/oxygen mixture was delivered to the reactor under the conditions described above at a space velocity of 26 moles of all feed components/kg-hr. The reaction evolved heat, and the catalyst bed temperature during this run was 334.2° C. The results are summarized in the Table 12 below.

TABLE 12

|  | Ex. 7 | Ex. 8 | Ex. 9 |
|---|---|---|---|
| Space velocity (total moles feed/(kg catalyst · hr) | 60 | 138 | 26 |
| % acetic acid accountability | 87.2 | 92.9 | 80.4 |
| Total moles acrylates/kg-hr | 2.7 | 6.1 | 1.0 |
| % $H_2CO$ conversion | 85.0 | 80.1 | 91.4 |
| % yield acrylates from $H_2CO$ fed | 68.5 | 68.8 | 60.8 |
| % selectivity to acrylates from $H_2CO$ reacted | 80.6 | 86.0 | 66.5 |

Thus, the high space velocity conditions of the invention produced less acetic acid destruction, higher space time yields, higher yields of acrylates from formaldehyde equivalents fed and a higher selectivity to acrylates from the formaldehyde reacted. These improvements in performance more than offset the small decrease in formaldehyde conversion, since the difference in formaldehyde conversion is due primarily to less formaldehyde being destroyed by the process of the invention. Also, formaldehyde would be recycled in a commercial process.

Example 10

This example illustrates that the preferred conditions of the invention allow for high selectivity and activity to be maintained over an extended period of time without the need for catalyst regeneration. The reactor set up for this example was similar to that of Examples 7-9, except for two differences. A different furnace was used, and the walls of this furnace were about 1.5 inches (3.8 cm) from the reactor. This configuration resulted in lower catalyst bed temperatures than in the previous examples. The furnace was set at 320° C., and the catalyst bed temperatures during the reaction ranged between about 327 and 332° C. The second difference is that the receiver was kept at ambient temperature instead of 0° C. The 1.31/0.33/0.45/2.93/0.19 molar ratio of acetic acid/formaldehyde/water/inerts/oxygen mixture was delivered to the reactor at a space velocity of 138 moles of all feed components/kg-hr. The reaction was run continuously without interruption or any catalyst regeneration. Two samples were collected during the first day of operation. Then one sample was collected per day. Table 13 below summarizes the performance of the preferred process of the invention on day 4, 17, and 31 of continuous operation without any regeneration.

TABLE 13

| Day | 4 | 17 | 31 |
|---|---|---|---|
| % acetic acid accountability | 98.7 | 99.7 | 98.9 |
| Total moles acrylates/kg-hr | 4.7 | 4.4 | 4.4 |

TABLE 13-continued

| Day | 4 | 17 | 31 |
|---|---|---|---|
| % $H_2CO$ conversion | 55.0 | 50.6 | 54.5 |
| % yield acrylates from $H_2CO$ fed | 52.5 | 49.6 | 49.3 |
| % selectivity to acrylates from $H_2CO$ reacted | 95.4 | 97.9 | 90.4 |

Examples 11 through 25 below exemplify the preparation of the supported catalysts of the invention. Examples 26 through 37 demonstrate the utility of the supported catalysts of the invention in the preparation of acrylic acid from acetic acid and a formaldehyde source.

Example 11

A solution was prepared from ammonium vanadate (0.97 g, 8.29 mmole), water (10 mL), and oxalic acid (2.09 g, 16.58 mmole). The ammonium vanadate dissolved without heating with the evolution of gas to form a blue solution. The soluble Ti source used in this example was titanium(IV) bis(ammonium lactate)dihydroxide, 50 wt % in water (TBALDH), certified to contain 13.4 wt % $TiO_2$. 9.886 g (0.0166 mole Ti) of the TBALDH solution were added to the aqueous V/oxalic acid solution. The solution remained clear blue with no precipitate. Since gas was evolved from the solution, an accurate weight was needed for this solution to be used for impregnations. By weighing the flask+stirrer+solution and subtracting the weight of the dry flask and stirrer, the weight of the solution was 22.42 g (22.28 g was transferred to a storage bottle). Each gram of this solution contained 0.3698 mmole V (18.83 mg) and 0.7395 mmole Ti (35.42 mg). The density of this solution was 1.15 g/mL.

Example 12

A test was performed to test how the solution of Example 11 behaved when dried and how the dried mass reacted with aqueous $H_3PO_4$. 1.560 g of the solution of Example 11 was placed in an evaporating dish and heated on the steam bath. This produced a dark blue-green glass (0.440 g). This glass was treated with a solution prepared from 0.401 g 85% $H_3PO_4$ (calculated amount 0.379 g) diluted to 1.3 mL with water. At first, about 20% of the glass dissolved to form a clear green solution, but then the whole system set up as a thick light-green paste.

Example 13

A $TiO_2$ supported catalyst precursor was prepared using a portion of the solution from Example 11 (4.08 g) and $TiO_2$ ⅟₁₆-inch extrudates (5.0 g, Alfa Aesar lot # K21S005). These conditions were about incipient wetness. The white $TiO_2$ turned gray upon impregnation. The impregnated $TiO_2$ was dried on the steam bath with occasional stirring. The steam bath-dried material was light gray. This material was dried in the muffle furnace overnight at 110° C. The material was light gray-tan upon removal from the muffle furnace. Phosphorus was added to the catalyst precursor using an aqueous solution of phosphoric acid by incipient wetness with the solution prepared to contain sufficient phosphorus to give a PN molar ratio=5.5. The amount of solution required was calculated from the measured density of solution of Example 11 (1.15 g/mL) that was used to prepare the original catalyst precursor such that the volume of the aqueous phosphoric acid solution was the same as that of the solution of Example 11 originally used. A solution was prepared from 0.996 g 85% $H_3PO_4$ (calculated amount 0.992 g) diluted to 3.5 mL with water and used to impregnate the material recovered from the muffle furnace. The resulting impregnated material was very light-green. The phosphoric acid impregnated sample appeared to be at incipient wetness and was stirred with a Teflon spatula in its evaporating dish on the steam bath until free flowing. The color remained green, but became a lighter shade as the water evaporated. The sample in its evaporating dish was placed in the muffle furnace and heated to 110° C. for 2 hours then heated to 450° C. for 6 hours. The resulting catalyst (5.912 g) was yellow.

Example 14

A $SiO_2$ supported catalyst precursor was prepared using a portion of the solution from Example 11 (6.82 g) and 8 mesh Davison grade 57 $SiO_2$ (5.0 g, lot 557). These conditions were about incipient wetness. The wet impregnated $SiO_2$ was dark blue. This material was dried on the steam bath with occasional stirring. The steam bath-dried material was light blue. This material was dried in the muffle furnace over night at 110° C. The material was dark blue upon removal from the muffle furnace.

Phosphorus was added to the catalyst precursor using an aqueous solution of phosphoric acid by incipient wetness with the solution prepared to contain sufficient phosphorous to give a P/N molar ratio=5.5. The amount of solution required was calculated from the measured density of solution of Example 11 (1.15 g/mL) that was used to prepare the original catalyst precursor such that the volume of the aqueous phosphoric acid solution was the same as that of the solution of Example 11 originally used. A solution was prepared from 1.654 g 85% $H_3PO_4$ (calculated amount 1.658 g) diluted to 5.9 mL with water and used to impregnate the material recovered from the muffle furnace. The resulting impregnated material was very dark green.

The phosphoric acid impregnated sample appeared to be at incipient wetness and was stirred with a Teflon spatula in its evaporating dish on the steam bath until free flowing. The color remained green, but became a lighter shade as the water evaporated. The sample in its evaporating dish was placed in the muffle furnace and heated to 110° C. for 2 hours, then heated to 450° C. for 6 hours. The resulting catalyst (6.572 g) was green with orange regions and looked most like the bulk V/2Ti/5.5P oxide catalyst.

Example 15

An alumina supported catalyst precursor was prepared using a portion of the solution from Example 11 (7.24 g) and high surface area aluminum oxide ⅛-inch extrudates (5.0 g, Alfa Aesar lot no A22M20, stock no 43832, bimodal pore distribution, surface area approximately 255 m2/g). During the preparation, too much solution (9.094 g) was added, and a portion (discarded) was removed with a dropper to bring the amount of the solution remaining to 7.24 g. With this amount of solution, the catalyst was wet, but little solution was visible on the evaporating dish. The catalyst precursor was blue when initially impregnated. It was dried on the steam bath with occasional stirring. The steam bath-dried material was light gray. This material was dried in the muffle furnace over night at 110° C. The material was light gray-tan upon removal from the muffle furnace.

Phosphorus was added to the catalyst precursor using an aqueous solution of phosphoric acid by incipient wetness with the solution prepared to contain sufficient phosphorous to give a P/N molar ratio=5.5. The amount of solution required was calculated from the measured density of solution of Example 11 (1.15 g/mL) that was used to prepare the original catalyst precursor such that the volume of the aqueous phosphoric acid solution was the same as that of the solution of Example 11 originally used. A solution was prepared from 1.761 g 85% $H_3PO_4$ (calculated amount 1.760 g) diluted to 6.3 mL with water and used to impregnate the material recovered from the muffle furnace. The resulting impregnated material was light-green.

The phosphoric acid impregnated sample appeared to be at incipient wetness and was stirred with a Teflon spatula in its evaporating dish on the steam bath until free flowing. The color remained green, but became a lighter shade as the water evaporated. The sample in its evaporating dish was placed in the muffle furnace and heated to 110° C. for 2 hours, then heated to 450° C. for 6 hours. The resulting catalyst (6.802 g) was light-green and the extrudates had some cracks in them.

Example 16

An aqueous V/Ti solution was prepared as follows. Ammonium vanadate (0.97 g, 8.28 mmole) and oxalic acid dehydrate (2.09 g, 16.58 mmole) were dissolved in water with stirring at room temperature. The color of this solution changed over the course of an hour from orange to red to brown to brown/green (with the evolution of bubbles) to dark green to dark blue. After waiting about an additional hour, no gas evolution was seen from the blue solution. About 240 mg gas had evolved based on the weight loss of the solution. TBALDH solution (9.89 g, 16.6 mmole Ti) was added to yield a dark blue solution (22.62 g). Each gram of this solution contained 0.3665 mmole V (18.67 mg) and 0.7339 mmole Ti (35.15 mg).

A zirconium oxide supported catalyst was prepared from a portion of this solution (2.355 g) and zirconium oxide catalyst support (5.0 g, Alfa Aesar lot # B21T010) ⅛-inch extrudates. This amount was close to incipient wetness and the wet catalyst in the evaporating dish had a light blue color. The impregnated material was dried with stirring on the steam bath to yield a material with very light blue color. This material was placed in the muffle furnace and dried overnight at 110° C. The material recovered from the muffle furnace was light gray-tan colored.

In theory, this catalyst contained 0.8631 eq V, so 5.5 times that amount (4.747 mmole) of phosphorus was required for the second impregnation or 547.3 mg 85% $H_3PO_4$. A solution was prepared from 547 mg 85% $H_3PO_4$ and diluted with water to a volume=2.0 mL. The sample of the material recovered from the muffle furnace was placed in a clean evaporating dish and impregnated with the aqueous $H_3PO_4$ solution. The conditions used in this impregnation were close to incipient wetness (some liquid also wetted the evaporating dish). The mixture was dried with stirring with a Teflon spatula until free flowing. The steam bath dried material was light-green and looked homogeneous. It was placed in the muffle furnace and dried at 110° C. for 2 hours.

The material recovered from the muffle furnace was gray-tan colored. It was kept in the same evaporating dish and calcined in the muffle furnace for 6 hours at 450° C. The material recovered from the muffle furnace (5.45 g) was uniformly yellow.

Example 17

The catalyst of this example was designed to have the approximate ratios of added species: V/Ti/P=1/2/5.5 (neglecting the $TiO_2$ support). The catalyst precursor was 2.4 wt % V on TiO$_2$ extrudates prepared from aqueous VCl$_3$ and ⅟₁₆-inch TiO$_2$ extrudates followed by calcinations at 500° C. for 2 hours. 5.0 grams of this catalyst were placed in an evaporating dish and impregnated with 2.81 g titanium(IV) bis(ammonium lactate)dihydroxide, 50 wt % in water (TBALDH), certified to contain 13.4 wt % TiO$_2$, while stirring. This amount of the TBALDH solution (ca. 2.3 mL) was about right for incipient wetness impregnation, and the catalyst surface was wet, but there was no puddle in the evaporating dish. The starting charge of the V/TiO$_2$ catalyst contained approximately 2.356 mmole V, and the TBALDH solution contained about twice this amount of Ti (about 4.71 mmole). The evaporating dish containing the Ti-impregnated V/TiO$_2$ material was placed into a muffle furnace and heated at 110° C. overnight. The catalyst recovered from the muffle furnace has a gray color whereas the starting V/TiO$_2$ catalyst was light tan. This material was impregnated with a mixture prepared from 85% H$_3$PO$_4$ (1.494 g, 12.96 mmole P) diluted to 2.3 mL with water. This amount of solution was also very close to incipient wetness, although the base of the evaporating dish was also wet. The evaporating dish was placed on the steam bath and heated with occasional stirring until the extrudates appeared dry. The evaporating dish was placed in the muffle furnace and dried at 110° C. for two hours, then at 500° C. for 6 hours. The material recovered from the muffle furnace (6.16) g was a darker tan than the starting V/TiO$_2$ material (sort of a gray-tan).

Example 18

This example illustrates the use a more concentrated V/Ti aqueous solution where the ammonium vanadate and oxalic acid were not dissolved in water first (unlike the case of Example 11). This allows for a single incipient wetness impregnation of these two metals to provide about twice the loading on the silica support as in Example 14. A solution was prepared from ammonium vanadate (0.97 g, 8.29 mmole), titanium(IV) bis(ammonium lactate)dihydroxide (50 wt % in water (TBALDH) certified to contain 13.4 wt % TiO$_2$) (9.886 g, 16.6 mmole Ti, of the TBALDH solution), and oxalic acid dehydrate (2.09 g, 16.58 mmole). After an hour, a dark blue solution resulted with mass=12.89 g. 1 gram of this solution contained 0.643 mmole V (32.76 mg) and 1.288 mmole Ti (61.69 mg).

Davison 8 mesh grade 57 SiO$_2$ (5.0 g, Lot 557) was loaded into an evaporating dish. This SiO$_2$ was loaded with the V/Ti aqueous solution (7.959 g) to the point of incipient wetness (7.63 g were required for about a 5 wt % V loading). This material was stirred on the steam bath until dry and free flowing. It was then transferred to the muffle furnace and heated to 110° C. for 4 hours. The material recovered from the muffle furnace (8.454 g) was light blue and was fairly uniformly impregnated (note the material Example 14 was dark blue at this stage of the process).

A solution was prepared from 85% phosphoric acid (3.245 g, 28.147 mmole) and diluted to 5.9 mL with water. This amount of P is a 5.5 molar excess over the amount of V already on the silica. The silica containing the V and Ti in the evaporating dish was impregnated with all of the aqueous phosphoric acid solution. The 5.9 mL charge was slightly in excess of the amount required for incipient wetness (perhaps by about 0.5 mL). The catalyst immediately became dark green, and the residual liquid portion was green. The mixture was heated on the steam bath with stirring until the material was free flowing and there was no sign of any precipitation in the green liquid as it was evaporated (suggesting some degree of solubility of the V in the aqueous phosphoric acid solution). Steam bath dried material was light-green and appeared to be fairly uniformly impregnated. It was placed in the muffle furnace and heated overnight at 110° C. The material obtained from the 110° C. muffle furnace (10.381 g) was light-green. 10.326 g of this material were transferred to a new evaporating dish. This material was placed in the muffle furnace and heated at 450° C. for 6 hours. 8.194 g of green catalyst were recovered from the muffle furnace.

Example 19

A solution was prepared from ammonium vanadate (4.85 g, 41.5 mmole), oxalic acid (10.45 g, 82.9 mmole), and water (50 mL). The initial mass of this solution was 64.91 g, and the mass after the gas evolution had ceased was 63.31 g (loss of 1.60 g). The aqueous TBALDH solution (49.43 g, 83.0 mmole Ti) was added to the ammonium vanadate solution. The mass of the resulting solution was 112.76 g. Each gram of this solution was calculated to contain 0.368 mmole V (18.74 mg) and 0.736 mmole Ti (35.26 mg).

Silica chunks (50.02 g, 8 mesh, Davison Grade 57, Lot 557) were placed in an evaporating dish. The silica in the evaporating dish was impregnated to incipient wetness with a portion of the solution (76.43 g). The mixture was dried with occasional stirring on the steam bath until free flowing and light blue, then dried further in the muffle furnace at 110° C. overnight. 64.31 grams were recovered from the muffle furnace. The catalyst contained 28.13 mmole V. Each gram contained 0.4374 mmole V (22.28 mg). The catalyst was divided up into 6 gram portions for phosphorus loading, so a 6 g charge contained 2.2244 mmole V.

One feature of the invention is that once the V and Ti are on the support, many different catalysts can be prepared by using different amounts of the phosphorus component to be loaded onto the catalyst as illustrated in Examples 20 through 23.

Example 20

This example illustrates the preparation of a molar ratio V/2Ti/3.5P oxide catalyst. 6.0 g of the Example 19 catalyst were placed in an evaporating dish. This catalyst was impregnated with a solution prepared from 85% H$_3$PO$_4$ (1.06 g, 9.18 mmole P) diluted to 5.5 mL (the 5.5 mL dilution provided incipient wetness with this amount of catalyst precursor). The mixture was stirred on the steam bath until free flowing. The catalyst precursor sample was placed in the muffle furnace and dried at 110° C. for one hour. The dried catalyst was transferred to a clean evaporating dish, returned to the muffle furnace, and then calcined at 450° C. for 6 hours. 5.789 g were recovered.

Example 21

This example illustrates the preparation of a molar ratio V/2Ti/4.0P oxide catalyst. 6.0 g of the Example 19 catalyst were placed in an evaporating dish. This catalyst was impregnated with a solution prepared from 85% H$_3$PO$_4$ (1.21 g, 10.50 mmole P) diluted to 5.5 mL. The mixture was stirred on the steam bath until free flowing. The catalyst precursor sample was placed in the muffle furnace and dried at 110° C. for one hour. The dried catalyst was transferred to a clean evaporating dish, returned to the muffle furnace, and then calcined at 450° C. for 6 hours. 5.855 g were recovered.

Example 22

This example illustrates the preparation of a molar ratio V/2Ti/4.5P oxide catalyst. 6.0 g of the Example 19 catalyst were placed in an evaporating dish. This catalyst was impregnated with a solution prepared from 85% $H_3PO_4$ (1.36 g, 11.81 mmole P) diluted to 5.5 mL. The mixture was stirred on the steam bath until free flowing. The catalyst precursor sample was placed in the muffle furnace and dried at 110° C. for one hour. The dried catalyst was transferred to a clean evaporating dish, returned to the muffle furnace, and then calcined at 450° C. for 6 hours. 5.999 g were recovered.

Example 23

This example illustrates the preparation of a molar ratio V/2Ti/5.0P oxide catalyst. 6.0 g of the Example 19 catalyst were placed in an evaporating dish. This catalyst was impregnated with a solution prepared from 85% $H_3PO_4$ (1.51 g, 13.12 mmole P) diluted to 5.5 mL. The mixture was stirred on the steam bath until free flowing. The catalyst precursor sample was placed in the muffle furnace and dried at 110° C. for one hour. The dried catalyst was transferred to a clean evaporating dish, returned to the muffle furnace, and then calcined at 450° C. for 6 hours. 6.085 g were recovered.

Example 24

A supported catalyst comprising 5 mole % vanadium and 10 mole % phosphorus was prepared in the following way: A white crystalline titanium pyrophosphate ($TiP_2O_7$) with a specific surface area of 100 $m^2$/g was first prepared according to the procedure described in I. C. Marcu et al., *J. Mol. Catal.*, Vol. 203, pp. 241-250 (2003), then crushed and sieved through an 8×14 mesh. A solution was prepared from ammonium vanadate (0.164 g, 0.0014 mole), 85% $H_3PO_4$ (0.326 g, 2.83 mmole), water (10 mL), and lactic acid (1.13 g, 12.54 mmole). The ammonium vanadate dissolved without heating to form a green solution. The solution was then added to 6.21 g of the $TiP_2O_7$ 8×14 meshed material (0.028 mole) in a 100 mL single necked round bottomed flask. The flask was then placed on a roto-evaporator with a water bath set to 65° C. and rotated in the bath under ambient pressure for 20 minutes, the supernatant turned blue during this time. The flask contents were then dried under vacuum at 65° C. and calcined at 450° C. in air for 16 hours to give yellow-green irregular shaped particles.

Example 25

A supported catalyst comprising 5 mole % vanadium, 10 mole titanium, and 10 mole % phosphorus was prepared in the following way: A white crystalline titanium pyrophosphate ($TiP_2O_7$) with a specific surface area of 100 $m^2$/g was first prepared according to the procedure described in I. C. Marcu et al., *J. Mol. Catal.*, Vol. 203, pp. 241-250 (2003), then crushed and sieved through an 8×14 mesh. A solution was prepared from ammonium vanadate (0.163 g, 0.0014 mole), TBALDH (1.67 g, 2.84 mmole), water (10 mL), and lactic acid (1.13 g, 12.54 mmole). The ammonium vanadate dissolved without heating to form an orange solution. The solution was then added to 6.21 g of the $TiP_2O_7$ 8×14 meshed material (0.028 mole) in a 100 mL single necked round bottomed flask. The flask was then placed on a roto-evaporator with a water bath set to 65° C. and rotated in the bath under ambient pressure for 20 minutes, the supernatant turned green during this time. The flask contents were then dried under vacuum at 65° C. followed by addition of a solution of 85% $H_3PO_4$ (0.33 g, 2.86 mmole) in water (15 mL). The resulting suspension was then dried under vacuum on the roto-evaporator at 65° C., then calcined at 450° C. in air for 16 hours to give yellow irregular shaped particles.

Examples 26-37

The condensation reaction of acetic acid and trioxane (the formaldehyde source) for Examples 26-35, using the supported catalysts from Examples 13-18 and 20-23, respectively, were performed following the procedures of Comparative Example 1.

The condensation reactions of acetic acid and trioxane (the formaldehyde source) for Examples 36-37, using the supported catalysts from Examples 24-25, respectively, were performed following the procedures of Example 1.

The vapor-phase condensation experiments of Examples 26-37 were performed for three hours with a 12 acetic acid/1 trioxane molar ratio feed (density 1.06 g/mL) at 325° C., 0.083 mL liquid feed/minute, and 80 SCCM $N_2$. The performance of these catalysts is summarized in Tables 14 and 15 below. These examples show that a supported V—Ti—P catalyst can be produced using the water soluble redox-active organo-titanium compound. One skilled in the art recognizes that titanium chloride is not amendable to impregnation on a solid support catalyst; the hydrochloric acid generated from titanium chloride hydrolysis can be destructive to the support material.

TABLE 14

| Example No. | 26 | 27 | 28 | 29 | 30 | 31 | 32 |
|---|---|---|---|---|---|---|---|
| Catalyst from Example No. | 13 | 14 | 15 | 16 | 17 | 18 | 20 |
| Catalyst charge, g | 5 | 5 | 5 | 5 | 5 | 5 | 5 |
| Catalyst charge, mL | 5.5 | 9.5 | 9.5 | 4.5 | 5 | 7.5 | 7.5 |
| Product, g | 13.738 | 14.391 | 13.576 | 13.638 | 13.714 | 14.255 | 13.992 |
| Reactants fed, g | 15.836 | 15.836 | 15.836 | 15.836 | 15.836 | 15.836 | 15.836 |
| GC Results | | | | | | | |
| Acetone, wt % | 0 | 0 | 0.18 | 0 | 0 | 0 | 0 |
| MeOAc, wt % | 0.21 | 0 | 0.58 | 0.17 | 0.16 | 0.09 | 0.16 |
| MA, wt % | 0 | 0 | 0 | 0 | 0 | 0 | 0.03 |
| Water, wt % | 7.46 | 6.31 | 6.93 | 4.11 | 5.25 | 6.12 | 6.22 |
| HOAc, wt % | 80.66 | 74.92 | 80.03 | 80.85 | 81.98 | 75.77 | 74.57 |
| Acrylic acid, wt % | 11.81 | 16 | 4.9 | 6.71 | 12.83 | 15.12 | 16.02 |
| HOPr, wt % | 0.21 | | | | | | |
| Total knowns, wt % | 100.35 | 97.23 | 92.62 | 91.84 | 100.22 | 97.09 | 97 |

TABLE 14-continued

| Example No. | 26 | 27 | 28 | 29 | 30 | 31 | 32 |
|---|---|---|---|---|---|---|---|
| Key Metrics | | | | | | | |
| Total mole acrylates/kg-hr | 1.5 | 2.1 | 0.6 | 0.8 | 1.6 | 2.0 | 2.1 |
| % yield acrylic acid from H2CO | 38.4 | 54.5 | 15.8 | 21.7 | 41.7 | 51.0 | 53.1 |
| % HOAc conv to AA | 9.6 | 13.6 | 3.9 | 5.4 | 10.4 | 12.8 | 13.3 |
| mmol HOAc unaccounted for | 27.0 | 22.9 | 42.4 | 37.8 | 22.5 | 24.5 | 29.2 |
| % HOAc accountability | 88.5 | 90.2 | 81.9 | 83.9 | 90.4 | 89.6 | 87.5 |

TABLE 15

| Example No. | 33 | 34 | 35 | 36 | 37 |
|---|---|---|---|---|---|
| Catalyst from Example No. | 21 | 22 | 23 | 24 | 25 |
| Catalyst charge, g | 5 | 5 | 5 | 5 | 5 |
| Catalyst charge, mL | 9.5 | 9.5 | 10 | 9.75 | 9.75 |
| Product, g | 14.415 | 14.248 | 14.315 | 14.1 | 14.4 |
| Reactants fed, g | 15.836 | 15.836 | 15.836 | 15.836 | 15.836 |
| GC Results | | | | | |
| Acetone, wt % | 0 | 0 | 0 | 0.06 | 0.09 |
| MeOAc, wt % | 0.14 | 0.12 | 0.07 | 0.11 | 0.17 |
| MA, wt % | 0 | 0.02 | 0.02 | 0 | 0 |
| Water, wt % | 7.09 | 6.81 | 6.33 | 6.52 | 6.66 |
| HOAc, wt % | 78.01 | 77.92 | 74.74 | 73.77 | 75.36 |
| Acrylic acid, wt % | 16.62 | 17.17 | 15.95 | 15.7 | 12.39 |
| HOPr, wt % | | | | | |
| Total knowns, wt % | 101.86 | 102.04 | 97.11 | 98.13 | 97.07 |
| Key Metrics | | | | | |
| Total mole acrylates/kg-hr | 2.2 | 2.3 | 2.1 | 2.05 | 1.65 |
| % yield acrylic acid from H2CO | 56.7 | 57.9 | 54.1 | 52.76 | 42.52 |
| % HOAc conv to AA | 14.2 | 14.5 | 13.5 | 13.09 | 10.55 |
| mmol HOAc unaccounted for | 13.6 | 15.3 | 24.4 | 30.17 | 28.36 |
| % HOAc accountability | 94.2 | 93.5 | 89.6 | 87.14 | 87.91 |

Example 38

Synthesis of V—Ti—P Catalyst

The catalyst was prepared by suspending ammonium metavanadate (19.455 g) in 300 mL of deionized water in a 500 mL single necked round bottomed flask. After heating at 70° C. for 1 hour, 85% orthophosphoric acid (105.4 g) was added at 70° C. over a 15 minute period to give a light orange solution. Residual reactants were washed into the reaction flask with a minimal amount of water. The 50 wt % titanium(IV) bis(ammonium lactato)dihydroxide (TBALDH) solution (218.45 g) was added to a 1 L three necked kettle reactor equipped with a condenser and a mechanical stirrer. The V/P solution was slowly poured into the TBALDH solution to give a pale green suspension. The V/P flask was rinsed with 30 mL of water and the contents added to the reaction flask. The mixture was then stirred at 700 to 800 rpm at 100° C. for 16 hours. The water was then removed via distillation over 4 to 6 hr and the resulting damp pale green solid transferred to a ceramic dish and heated in air at 90° C. for 16 hours in a muffle furnace. The resulting solid was crushed to fine particles using a mortar and a pestle. This material was then calcined for 6 hours at 450° C. in air (60 SCCM) in a quartz tube to give pale green catalyst particles. This material had a BET surface area of 37.9 m$^2$/g, was amorphous via X-ray diffraction and had a molar composition of 1.0V-1.9Ti-5.2P, as determined by X-ray Fluorescence Spectroscopy. The catalyst was regenerated in air (100 SCCM) at 400° C. overnight after each experiment.

Examples 39-44

Synthesis of Methylene Diacetate

A 5 L round-bottom flask was fitted with a condenser, thermowell, overhead stirrer, inert gas bubbler, and heating mantle. To this flask was added 885 grams of paraformaldehyde followed by 3,324 mL of acetic anhydride. The mixture was stirred at room temperature and 12 mL of concentrated sulfuric acid was added. An exotherm heated the solution to approximately 80° C. and then the heating mantle was turned on. The mixture was held at reflux for almost 10 hours and sampled periodically to check for completion by gas chromatography. Upon completion, 35 g of NaOAc was added to the mixture to neutralize the sulfuric acid. The mixture was transferred to another flask and essentially pure MDA was distilled.

Condensation Reaction

The condensation reaction reactor was a 25 mm outer diameter (21 mm inner diameter) quartz reactor tube with length=61 cm (24 inches). Heat to the reactor was provided by a Barnstead International electric tube furnace (type F21100). The reactor was charged with 10 g of 8 by 14 mesh V—Ti—P catalyst (Example 38). Liquid products were collected in an atmosphere-air cooled three necked flask. The base of the receiver flask was fitted with a stopcock to allow for draining of the liquid products. 0.2 mL/minute of liquid methylene diacetate was vaporized and fed to the reactor which was heated at temperatures ranging from 190° C. to 310° C. Nitrogen was fed as a diluent at varying rates (SCCM) to produce a contact time between the total feed and catalyst of approximately one second. No water was fed to the reactor. The reaction was performed for 4 hours. As a substantial exotherm was observed in the first 3 to 10 minutes of the reaction, the first hour of reaction product was discarded; liquid product was then collected after this first hour. A liquid product sample from the last three hours of the experimental run was collected, weighed and analyzed by gas chromatography. The results are presented in Table 16. In Table 16, the conversions are based on moles of methylene diacetate converted to initial moles of methylene diacetate fed and the space time yield (STY) of acrylic acid is equal to moles of acrylic acid produced per kg of catalyst per hour.

The vapor phase condensation experiment was repeated at temperatures ranging from 310° C. to 190° C., as given in Table 16. In Example 43, water was added to the feed at a molar ratio of one mole of methylene diacetate to one mole of water. For Example 43, the diluent gas flow rate was lowered to maintain a contact time between reactants and the catalyst at approximately one second. The diluent for Examples 39-43 was nitrogen, whereas the diluent for Example 44 was 6% oxygen and 94% nitrogen. The results are summarized in Table 16.

TABLE 16

| Example | MDA/ Water | Furnace Temp. (° C.) | Contact Time (sec.) | MDA Conversion (%) | Acrylic Acid STY (moles/kg catalyst/hr) | Paraformaldehyde by-product |
|---|---|---|---|---|---|---|
| 39 | 1/0 | 310 | 1.02 | 75 | 3.60 | No |
| 40 | 1/0 | 250 | 1.01 | 57 | 3.01 | No |
| 41 | 1/0 | 220 | 1.02 | 35 | 1.40 | No |
| 42 | 1/0 | 190 | 1.02 | 25 | 0.70 | No |
| 43 | 1/1 | 250 | 1.02 | 97 | 3.30 | Yes |
| 44 | 1/0 | 250 | 1.01 | 68 | 3.23 | No |

As can be seen from Examples 39-44 in Table 16, methylene diacetate can be used as a feed to synthesize acrylic acid over a V—Ti—P catalyst. As expected, the STY of acrylic acid and methylene diacetate conversions decrease with temperature. The STY do not decrease in the presence of an equal molar amount of water when using methylene diacetate as a feed (comparing Examples 40 and 43).

Comparative Examples 9-18

The same reactor, catalyst, and experimental procedure as used in Examples 39-44 was repeated using acetic acid and formaldehyde as the feed in place of methylene diacetate. The feed was a 2:1 acetic acid to formaldehyde (fed as trioxane) feed. The amount of water in each feed as well as the temperatures are given in Table 17. The residence time was maintained constant at approximately 1 second for comparison purposes by changing the diluent $N_2$ flow rate as the total feed rate (inclusive of organics, water and diluent gas) changed based upon the amount of water in a given example. The results are summarized in Table 17. In Table 17, the conversions are based on moles of formaldehyde, fed as trioxane, converted to initial moles of formaldehyde and the space time yield (STY) of acrylic acid is equal to moles of acrylic acid produced per kg of catalyst per hr. The diluent gas in Comparative Examples 9-17 was nitrogen, whereas the diluent gas in Comparative Example 18 was 6% oxygen and 94% nitrogen.

TABLE 17

| Comparative Example | Acetic Acid/ $CH_2O$/ Water | Furnace Temp. (° C.) | Contact Time (sec.) | Formaldehyde Conversion (%) | Acrylic Acid STY (moles/kg catalyst/hr) | Paraformaldehyde by-product |
|---|---|---|---|---|---|---|
| 9 | 2/1/3 | 310 | 1.00 | 20 | 1.17 | No |
| 10 | 2/1/3 | 280 | 1.00 | 8 | 0.38 | No |
| 11 | 2/1/3 | 250 | 1.00 | 10 | 0.05 | No |
| 12 | 2/1/1 | 310 | 0.97 | 34 | 2.24 | No |
| 13 | 2/1/1 | 280 | 1.03 | 26 | 0.94 | No |
| 14 | 2/1/1 | 250 | 1.02 | 22 | 0.19 | No |
| 15 | 2/1/0 | 310 | 1.01 | 58 | 3.77 | Yes |
| 16 | 2/1/0 | 280 | 1.01 | 50 | 2.93 | Yes |
| 17 | 2/1/0 | 250 | 1.01 | 33 | 1.43 | Yes |
| 18 | 2/1/0 | 250 | 1.01 | 41 | 1.52 | Yes |

This set of experiments evaluated the effect of water on STY by varying temperature and the molar ratio of acetic acid to formaldehyde to water between 2/1/3, 2/1/1 and 2/1/0 while keeping the other reactor parameters constant. As shown in Table 17, water has a deleterious effect on conversion and space time yield. To attempt to maintain the same space time yield of acrylic acid, the temperature must increase with the presence of water in the feed solution; this is another major drawback of using water. For example, a space time yield of 1.43 moles of acrylic acid/kg catalyst/hr (Comparative Example 17) was obtained at 250° C. with a feed ratio of 2/1/0. By contrast, a lower space time yield of 0.94 moles of acrylic acid/kg catalyst/hr (Comparative Example 13) was obtained with the addition of water to give the feed ratio of 2/1/1 even at the elevated temperature of 280° C.

To reduce the negative effects of water, trioxane can be employed in the liquid feed in the absence of additional water. Although this increases the reaction conversion and acrylic acid yield, generally the yields and conversions are substantially lower than the values obtained when methylene diacetate is used as the feed. This is observed even when using trioxane (without water addition) and acetic acid because the net solution still contains one mole of latent molecular water. This underscores the primary advantage of using methylene diacetate, i.e., improvement in space time yields and conversions due to complete elimination of water in the feed. For example, at 250° C. the space time yield of acrylic acid is 1.43 (Comparative Example 17) when using a conventional feed (defined as a solution of acetic acid and trioxane) whereas at the same temperature the space time yield is more than double at 3.01 (Example 40) when using a methylene diacetate feed.

Example 45

The ability of the V—Ti—P catalyst to be regenerated and yield the same reproducible experimental results is advantageous. The same catalyst that was used in Example 40 was regenerated overnight at 400° C. in a continuous flow of 100 SCCM air. The same reactor, catalyst, and experimental procedure as used in Example 40 were reproduced to give Example 45. The results are summarized in Table 18. Examples 45 and 40 demonstrate that the catalyst activity is reproducible after the regeneration step in air. The methylene diacetate conversion (57%) and the space time yield of acrylic acid (3.01 moles/kg catalyst/hr) are the same for each example. Moreover, paraformaldehyde was not formed in either example as observed from a lack of solids accumulated in the collection vessel.

TABLE 18

| Example | MDA/ Water | Furnace Temp. (° C.) | Contact Time (sec.) | MDA Conversion (%) | Acrylic Acid STY (moles/kg catalyst/hr) | Paraformaldehyde by-product |
|---|---|---|---|---|---|---|
| 40 | 1/0 | 250 | 1.01 | 57 | 3.01 | No |
| 45 | 1/0 | 250 | 1.01 | 57 | 3.01 | No |

Comparative Example 19

To verify the acrylic acid production was directly related to the V—Ti—P catalyst, the same reactor and experimental procedure as used in Examples 39-44 was repeated except the V—Ti—P catalyst powder was removed from the reaction tube and replaced with quartz chips. Just as the V—Ti—P catalyst is treated prior to the reaction, the quartz chips were calcined at 400° C. overnight in air. The results are given in Table 19. Comparative Example 19 demonstrates that the thermal treatment of a quartz surface alone is insufficient for the equivalent production of acrylic acid from a V—Ti—P catalyst.

TABLE 19

| Comparative Example | MDA/ Water | Furnace Temp. (° C.) | Contact Time (sec.) | MDA Conversion (%) | Acrylic Acid STY (moles/kg catalyst/ hr) | Paraformaldehyde by-product |
|---|---|---|---|---|---|---|
| 19 | 1/0 | 310 | — | 3 | 0.09 | No |

Comparative Examples 20 and 21

To further illustrate that the production of acrylic acid with MDA as a feed is a unique ability of the V—Ti—P catalyst, the catalyst powder was removed from the reaction tube and replaced with 10 g anatase titanium dioxide ($TiO_2$). Just as the V—Ti—P catalyst is treated prior to the reaction, the titanium dioxide material was calcined at 400° C. overnight in air. The same reactor and experimental procedure as used in Examples 39-44 was repeated. The results are given in Table 20. The Table 20 data demonstrates that the $TiO_2$ catalyst did not produce appreciable amounts of acrylic acid. The STY's are lower, 0.03 and 0.42, for the anatase $TiO_2$, (Comparative Examples 20 and 21, respectively) than the corresponding values, 3.60 and 3.01, when using the V—Ti—P catalyst (Examples 39 and 40, respectively). This comparison demonstrates that the anatase $TiO_2$ is not as desirable as the inventive V—Ti—P catalyst for the conversion of methylene diacetate to acrylic acid.

TABLE 20

| Comparative Example | MDA/ Water | Furnace Temp. (° C.) | Contact Time (sec.) | MDA Conversion (%) | Acrylic Acid STY (moles/kg catalyst/ hr) | Paraformaldehyde by-product |
|---|---|---|---|---|---|---|
| 20 | 1/0 | 310 | 1.02 | 24 | 0.03 | No |
| 21 | 1/0 | 250 | 1.01 | 15 | 0.42 | No |

Comparative Example 22

To even further exemplify the ability of the V—Ti—P catalyst to catalyze the production of acrylic acid from MDA, the V—Ti—P catalyst powder was removed from the reaction tube and replaced with 10 g of tungsten oxide ($WO_3$). Tungsten oxide was chosen since it is a typical oxide used for catalyzing aldol chemistry. Just as the V—Ti—P catalyst is treated prior to the reaction, the tungsten oxide material was calcined at 400° C. overnight in air. The same reactor and experimental procedure as used in Examples 39-44 was repeated. The results are given in Table 21. The Table 21 results show that the tungsten oxide's STY of 0.15 (Comparative Example 22) is lower than the STY of 3.01 for the inventive V—Ti—P catalyst (Example 40) at catalyzing the aldol condensation chemistry for MDA.

TABLE 21

| Comparative Example | MDA/ Water | Furnace Temp. (° C.) | Contact Time (sec.) | MDA Conversion (%) | Acrylic Acid STY (moles/kg catalyst/ hr) | Paraformaldehyde by-product |
|---|---|---|---|---|---|---|
| 22 | 1/0 | 250 | 1.01 | 7 | 0.15 | No |

Examples 46 and 47

To demonstrate the improved ability of the inventive V—Ti—P catalyst synthesized from a water-soluble, redox-active organo-titanium (Example 38) over the 'prior-art' V—Ti—P catalyst where the titanium source is from a non-water-soluble tetrachlorotitanium compound (Comparative Example 1), 10 g of the V—Ti—P catalyst described in Comparative Example 1 was substituted in for the inventive V—Ti—P catalyst. This 'prior-art' V—Ti—P material was calcined at 400° C. overnight in air before use and the same reactor and experimental procedure was used as in Examples 39-44. The results are summarized in Table 22. Examples 46 and 47 have STY of 1.58 and 1.51, respectively. These values are about 50% less than the corresponding STY, 3.60 and 3.01, of Examples 39 and 43, respectively.

TABLE 22

| Example | MDA/ Water | Furnace Temp. (° C.) | Contact Time (sec.) | MDA Conversion (%) | Acrylic Acid STY (moles/kg catalyst/ hr) | Paraformaldehyde by-product |
|---|---|---|---|---|---|---|
| 46 | 1/0 | 310 | 1.02 | 17 | 1.58 | No |
| 47 | 1/0 | 250 | 1.01 | 13 | 1.51 | No |

Examples 48 and 49

Synthesis of Methylene Dipropionate

Methylene dipropionate (MDP) was produced from a refluxing mixture of paraformaldehyde and propionic anhydride in the presence of a small amount of sulfuric acid. The reaction was followed by using gas chromatography. Upon completion of the reaction, sodium propionate was added to the mixture to neutralize the sulfuric acid. The mixture was distilled to give 99% pure methylene dipropionate.

Condensation Reaction

The condensation reaction conditions were the same as those used for the acrylic acid in Examples 39-44 with adjustment of the $N_2$ flow rate to maintain the 1 second residence time for the methylene dipropionate. Examples 48 and 49 presented here demonstrate the ability of methylene dipropionate to be used for the production of methacrylic acid; the results are presented in Table 23. Examples 48 and 49 show that the V—Ti—P catalyst is highly active towards the production of methacrylic acid from methylene dipropionate (MDP) with 98 mole % and 63 mole % conversion and space time yields of 3.83 and 2.00, respectively, for the methacrylic acid product. The results of Table 23 demonstrate that the STY of methacrylic acid from the conversion of methylene dipropionate decrease with temperature.

TABLE 23

| Example | MDP/ Water | Furnace Temp. (° C.) | Contact Time (sec.) | MDP Conversion (%) | Methacrylic Acid STY (moles/kg catalyst/ hr) | Paraformaldehyde by-product |
|---|---|---|---|---|---|---|
| 48 | 1/0 | 310 | 1.02 | 98 | 3.83 | No |
| 49 | 1/0 | 250 | 1.01 | 63 | 2.00 | No |

Comparative Examples 23-28

The vapor phase condensation experiments with a 2:1 propionic acid to formaldehyde (fed as trioxane) feed along with varying amounts of water were performed at temperatures ranging from 250° C. to 310° C., 0.2 mL liquid feed/minute for 4 hours. The residence time was maintained constant at approximately 1 second for comparison purposes by changing the diluent $N_2$ flow rate. The performance of the catalyst is summarized in Table 24. In Table 24, the conversions are based on moles of propionic acid converted to initial moles of propionic acid and the space time yield (STY) of methacrylic acid is equal to moles of methacrylic acid produced per kg of catalyst per hr. The reactor and experimental protocol used for these experiments was the same as those described in Examples 48 and 49. The catalyst was the same V—Ti—P material made in Example 38 but was regenerated prior to each experiment by an overnight calcination step in air at 400° C.

TABLE 24

| Comparative Example | Propionic Acid/ CH$_2$O/ Water | Furnace Temp. (° C.) | Contact Time (sec.) | Propionic Acid Conversion (%) | Methacrylic Acid STY (moles/kg catalyst/ hr) | Paraformaldehyde by-product |
|---|---|---|---|---|---|---|
| 23 | 2/1/3 | 310 | 1.02 | 12 | 0.16 | No |
| 24 | 2/1/3 | 250 | 1.03 | 13 | 0.01 | No |
| 25 | 2/1/1 | 310 | 1.03 | 13 | 0.55 | No |
| 26 | 2/1/1 | 250 | 1.05 | 10 | 0.04 | No |
| 27 | 2/1/0 | 310 | 1.00 | 9 | 0.73 | Yes |
| 28 | 2/1/0 | 250 | 1.02 | 3 | 0.18 | Yes |

The space time yields of methacrylic acid from the conversion of methylene dipropionate over the V—Ti—P catalyst were unexpected. Comparative Example 30 shows the STY of methacrylic acid at 250° C. is 0.18 when using a conventional feed of propionic acid and trioxane but a space time yield of 2.00 is obtained at the same temperature when using a feed of methylene dipropionate (Example 49). This more than eleven times higher STY is a benefit of using methylene dipropionate as the feed.

Tables 23 and Table 24 underscore the differences in space time yields depending on whether the production of methacrylic acid uses a conventional feed comprising varying ratios of propionic acid to formaldehyde to water of 2/1/3, 2/1/1 and 2/1/0 or the production of methacrylic acid with methylene dipropionate as the feed. When the conventional feed is used (Table 24, Comparative Examples 23-28) the STY's ranged from 0.01 to 0.73 while when the methylene dipropionate feed is used (Table 23, Examples 48 and 49) the STY's ranged from 2.00 to 3.83.

Comparative Example 29

To verify the methacrylic acid production was directly related to the V—Ti—P catalyst, the same reactor and experimental procedure as used in Examples 48 and 49 was repeated except the V—Ti—P catalyst powder was removed from the reaction tube and replaced with quartz chips. Just as the V—Ti—P catalyst was treated prior to the reaction, the quartz chips were calcined at 400° C. overnight in air. The results are given in Table 25. The Table 25 data demonstrates that the thermal treatment of a quartz surface alone is insufficient to prepare acrylic acid from a V—Ti—P catalyst and methylene dipropionate.

TABLE 25

| Comparative Example | MDP/ Water | Furnace Temp. (° C.) | Contact Time (sec.) | MDP Conversion (%) | Methacrylic Acid STY (moles/kg catalyst/ hr) | Paraformaldehyde by-product |
|---|---|---|---|---|---|---|
| 29 | 1/0 | 310 | — | 0 | 0 | — |

Example 50

Synthesis of V—Ti—P Catalyst

This catalyst was prepared by suspending ammonium metavanadate (19.53 g) and 90% lactic acid (121 g) in 200 mL of deionized water in a 500 mL single necked round bottomed flask. After heating at 70° C. for 1 hour, 85% orthophosphoric acid (105.2 g) was added at 70° C. over a 15 minute period to give a blue-green solution. Residual reactants were washed into the reaction flask with a minimal amount of water. The 50 wt % titanium(IV) bis(ammonium lactato)dihydroxide (TBALDH) solution (218.32 g) was added to a 1 L three necked kettle reactor equipped with a condenser and a mechanical stirrer. The V/P solution was slowly poured into the TBALDH solution to give a blue-green suspension. The V/P flask was rinsed with 30 mL of water and the contents added to the reaction flask. The mixture was then stirred at 700 to 800 rpm at 100° C. for 16 hours. The water was then removed via distillation over 4 to 6 hr and the resulting damp pale green solid transferred to a ceramic dish and heated in air at 90° C. for 16 hours in a muffle furnace. The resulting solid was crushed and sieved to 8×14 mesh particles using a mortar and a pestle. This material was then calcined for 6 hours at 450° C. in air (60 SCCM) in a quartz tube to give pale green catalyst particles. This material had a BET surface area of 47.0 m$^2$/g, was primarily amorphous via X-ray diffraction but showed traces of crystalline oxovanadium phosphate phases and had a molar composition of 1.0V-1.92Ti-5.26P, as determined by X-ray Fluorescence Spectroscopy.

Example 51

Condensation Reaction with No Oxygen Present

Reactor set-up: The condensation reaction of acetic acid and trioxane were conducted in a 25 mm outer diameter (21 mm inner diameter) quartz reactor tube with length=107 cm (42 inches). The reactor was heated using a 3-zone electric furnace while the liquid products were collected in a three-neck flask with a bottom outlet. One neck of the receiver flask was fitted to a water cooled condenser which was attached to a dry ice condenser with a trap. Samples were collected by draining the bottom outlet during the reaction and these respective collection times were recorded. The samples were then weighed and analyzed by gas chromatography and liquid chromatography. The quartz reactor was fitted with a thermowell at the center. The reactor was first loaded with quartz chips to allow the catalyst to be positioned in the middle of the 3-zone furnace. The reaction was then loaded with a 5.0 g (14.5 mL) charge of the catalyst from Example 50. The catalyst bed height was 4.1 cm (1.6 inches). The thermocouple in the thermowell was placed at the middle of the catalyst bed. Additional quartz chips were then added to the reactor until they reached the top of the furnace.

Condensation reaction: The vapor phase condensation reaction was conducted at 325° C. A mixture of acetic acid/trioxane/water (molar ratio 12/1/4.09) was fed to the reactor at 0.089 mL/min with a nitrogen feed at 70 SCCM with no oxygen. The reaction was run continuously for 72.53 hours under nitrogen with no oxygen present. Samples were taken periodically, then weighed and analyzed. The last sample was taken 2 hours after the liquid feed was stopped. Results are summarized in Table 26 and the conversions and selectivities are plotted in FIGS. 11 and 12, respectively. After the reaction, the catalyst was coked and black. The catalyst was regenerated in 80 SCCM nitrogen plus 13 SCCM air at 400° C. overnight, followed by heating in 60 SCCM air at 400° C. for 2 hours, and then heating at 450° C. for 7.5 hours.

TABLE 26

| Sample | Percent Oxygen (O$_2$) in Total Feed | Total Reaction Time (hr) | STY (mole/kg catalyst/hr) | Formaldehyde Conversion (%) | Selectivity HCHO to AA (%) |
| --- | --- | --- | --- | --- | --- |
| 1 | 0 | 3.00 | 2.11 | 68.0 | 79.2 |
| 2 | 0 | 6.00 | 1.81 | 59.3 | 77.7 |
| 3 | 0 | 21.42 | 1.14 | 47.5 | 61.3 |
| 4 | 0 | 24.42 | 0.83 | 34.1 | 61.8 |
| 5 | 0 | 27.42 | 0.74 | 31.1 | 61.0 |
| 6 | 0 | 30.42 | 0.67 | 27.9 | 61.3 |
| 7 | 0 | 45.42 | 0.53 | 23.1 | 58.9 |
| 8 | 0 | 48.92 | 0.41 | 19.8 | 53.1 |
| 9 | 0 | 53.92 | 0.35 | 18.1 | 49.8 |
| 10 | 0 | 69.53 | 0.27 | 14.4 | 48.3 |
| 11 | 0 | 72.53 | 0.23 | 10.8 | 53.3 |

As can be seen from Samples 1-11 recorded in Table 26, the space time yield, conversion, and selectivity decrease as the reaction progresses. A maximum value for the space time yield, conversion, and selectivity is noted at the beginning of the reaction since the catalyst is expected to be minimally coked and the reactive sites of the catalyst are still available to promote the reaction.

Examples 52-59

Condensation Reactions with Oxygen Present

The Reactor set-up and Condensation reactions for the catalyst runs with oxygen were conducted as described in Example 51 except that the nitrogen carrier gas was replaced with a mixture of nitrogen and air. The flow rates of nitrogen and air were adjusted to achieve the specified oxygen concentration in the total feed. Eight different Example reactions with varying oxygen amounts were carried out with 2.0% oxygen (Example 52), 2.4% oxygen (Example 53), 2.9% oxygen (Example 54), 3.0% oxygen (Example 55), 3.6% oxygen (Example 56), 3.9% oxygen (Example 57), 4.0% oxygen (Example 58), and 6.0% oxygen (Example 59) in the total feed. The three-neck receiver flask was half-jacketed and cooled at 0° C. with a circulating bath. The reaction exhibited a constant 10° C. exotherm, resulting in a catalyst bed temperature of 335° C. The reaction was run continuously for the specified run time. Multiple Samples were taken periodically for each of the Example runs, then weighed and analyzed. The results for each Example in terms of Samples taken are summarized in Tables 27 to 34 and the conversions and selectivities are plotted in FIGS. 11 and 12, respectively. After the reaction, the catalyst was coked and black. The number of samples taken during each of the following runs varied because of the permitted time for sampling.

TABLE 27

| Sample | Percent Oxygen (O$_2$) in Total Feed | Total Reaction Time (hr) | STY (mole/kg catalyst/hr) | Formaldehyde Conversion (%) | Selectivity HCHO to AA (%) |
| --- | --- | --- | --- | --- | --- |
| 1 | 2.0 | 2.00 | 4.83 | 59.4 | 85.3 |
| 2 | 2.0 | 4.00 | 4.24 | 49.9 | 89.3 |

TABLE 28

| Sample | Percent Oxygen (O$_2$) in Total Feed | Total Reaction Time (hr) | STY (mole/kg catalyst/hr) | Formaldehyde Conversion (%) | Selectivity HCHO to AA (%) |
| --- | --- | --- | --- | --- | --- |
| 1 | 2.4 | 23.35 | 2.36 | 71.3 | 84.3 |
| 2 | 2.4 | 47.82 | 2.24 | 69.7 | 82.1 |
| 3 | 2.4 | 72.12 | 2.24 | 68.3 | 83.7 |
| 4 | 2.4 | 97.62 | 2.24 | 70.7 | 80.9 |
| 5 | 2.4 | 120.92 | 2.29 | 66.6 | 87.6 |
| 6 | 2.4 | 143.72 | 2.13 | 68.4 | 79.3 |
| 7 | 2.4 | 167.98 | 2.11 | 68.4 | 78.6 |
| 8 | 2.4 | 192.08 | 2.19 | 67.4 | 83.1 |
| 9 | 2.4 | 216.03 | 1.95 | 69.0 | 72.1 |

TABLE 29

| Sample | Percent Oxygen (O$_2$) in Total Feed | Total Reaction Time (hr) | STY (mole/kg catalyst/hr) | Formaldehyde Conversion (%) | Selectivity HCHO to AA (%) |
| --- | --- | --- | --- | --- | --- |
| 1 | 2.9 | 2.00 | 6.53 | 70.0 | 74.4 |
| 2 | 2.9 | 4.00 | 5.72 | 64.7 | 70.4 |

TABLE 30

| Sample | Percent Oxygen (O$_2$) in Total Feed | Total Reaction Time (hr) | STY (mole/kg catalyst/hr) | Formaldehyde Conversion (%) | Selectivity HCHO to AA (%) |
| --- | --- | --- | --- | --- | --- |
| 1 | 3.0 | 3.03 | 2.20 | 68.0 | 82.5 |

TABLE 31

| Sample | Percent Oxygen (O$_2$) in Total Feed | Total Reaction Time (hr) | STY (mole/kg catalyst/hr) | Formaldehyde Conversion (%) | Selectivity HCHO to AA (%) |
| --- | --- | --- | --- | --- | --- |
| 1 | 3.6 | 3.87 | 4.64 | 55.2 | 94.0 |
| 2 | 3.6 | 22.87 | 4.74 | 53.9 | 98.3 |
| 3 | 3.6 | 46.90 | 4.78 | 52.1 | 102.6 |
| 4 | 3.6 | 74.20 | 4.70 | 55.0 | 95.5 |
| 5 | 3.6 | 94.42 | 4.76 | 52.6 | 101.3 |

TABLE 31-continued

| Sample | Percent Oxygen (O$_2$) in Total Feed | Total Reaction Time (hr) | STY (mole/kg catalyst/hr) | Formaldehyde Conversion (%) | Selectivity HCHO to AA (%) |
|---|---|---|---|---|---|
| 6 | 3.6 | 117.93 | 4.50 | 53.3 | 94.5 |
| 7 | 3.6 | 141.43 | 4.61 | 52.3 | 98.6 |
| 8 | 3.6 | 165.97 | 4.60 | 55.1 | 93.2 |
| 9 | 3.6 | 189.85 | 4.62 | 54.8 | 94.3 |
| 10 | 3.6 | 212.98 | 4.67 | 52.4 | 99.7 |
| 11 | 3.6 | 241.68 | 4.56 | 50.9 | 100.1 |
| 12 | 3.6 | 261.77 | 4.50 | 55.3 | 91.0 |
| 13 | 3.6 | 283.93 | 4.57 | 53.0 | 96.6 |
| 14 | 3.6 | 309.52 | 4.63 | 49.2 | 105.2 |
| 15 | 3.6 | 335.27 | 4.54 | 49.8 | 101.9 |
| 16 | 3.6 | 358.10 | 4.45 | 49.3 | 100.7 |
| 17 | 3.6 | 384.60 | 4.43 | 50.6 | 97.9 |
| 18 | 3.6 | 409.02 | 4.43 | 49.9 | 99.3 |
| 19 | 3.6 | 432.43 | 4.53 | 50.7 | 100.0 |
| 20 | 3.6 | 456.68 | 4.44 | 51.4 | 96.7 |
| 21 | 3.6 | 477.72 | 3.42 | 62.7 | 61.0 |
| 22 | 3.6 | 503.72 | 4.45 | 62.5 | 79.7 |
| 23 | 3.6 | 525.82 | 4.63 | 50.2 | 103.2 |
| 24 | 3.6 | 547.48 | 4.42 | 51.1 | 96.7 |
| 25 | 3.6 | 575.48 | 4.39 | 52.0 | 94.5 |
| 26 | 3.6 | 598.75 | 4.46 | 54.2 | 91.9 |
| 27 | 3.6 | 621.90 | 4.48 | 56.3 | 89.0 |
| 28 | 3.6 | 648.05 | 4.50 | 53.9 | 93.3 |
| 29 | 3.6 | 671.97 | 4.48 | 53.9 | 93.0 |
| 30 | 3.6 | 696.30 | 4.44 | 54.8 | 90.7 |
| 31 | 3.6 | 718.72 | 4.41 | 54.5 | 90.4 |
| 32 | 3.6 | 745.38 | 4.56 | 54.4 | 93.6 |
| 33 | 3.6 | 769.22 | 4.17 | 57.0 | 81.8 |
| 34 | 3.6 | 793.30 | 4.11 | 54.7 | 83.9 |
| 35 | 3.6 | 816.13 | 4.17 | 54.4 | 85.7 |

TABLE 32

| Sample | Percent Oxygen (O$_2$) in Total Feed | Total Reaction Time (hr) | STY (mole/kg catalyst/hr) | Formaldehyde Conversion (%) | Selectivity HCHO to AA (%) |
|---|---|---|---|---|---|
| 1 | 3.9 | 3.00 | 2.36 | 93.1 | 65.9 |
| 2 | 3.9 | 6.00 | 2.51 | 90.9 | 71.7 |
| 3 | 3.9 | 8.00 | 2.52 | 90.5 | 72.3 |
| 4 | 3.9 | 36.48 | 2.53 | 90.0 | 72.9 |
| 5 | 3.9 | 50.95 | 2.47 | 89.7 | 71.6 |
| 6 | 3.9 | 71.75 | 2.43 | 89.6 | 70.5 |
| 7 | 3.9 | 74.75 | 2.43 | 89.6 | 70.3 |
| 8 | 3.9 | 80.07 | 2.39 | 89.9 | 68.9 |
| 9 | 3.9 | 96.00 | 2.74 | 86.2 | 82.2 |
| 10 | 3.9 | 99.00 | 2.73 | 86.0 | 82.1 |
| 11 | 3.9 | 104.00 | 2.75 | 85.7 | 82.9 |
| 12 | 3.9 | 120.00 | 2.73 | 85.2 | 82.8 |
| 13 | 3.9 | 123.00 | 2.68 | 84.8 | 81.8 |
| 14 | 3.9 | 128.00 | 2.73 | 84.8 | 83.2 |

TABLE 33

| Sample | Percent Oxygen (O$_2$) in Total Feed | Total Reaction Time (hr) | STY (mole/kg catalyst/hr) | Formaldehyde Conversion (%) | Selectivity HCHO to AA (%) |
|---|---|---|---|---|---|
| 1 | 4.0 | 3.12 | 2.14 | 69.2 | 79.0 |

TABLE 34

| Sample | Percent Oxygen (O$_2$) in Total Feed | Total Reaction Time (hr) | STY (mole/kg catalyst/hr) | Formaldehyde Conversion (%) | Selectivity HCHO to AA (%) |
|---|---|---|---|---|---|
| 1 | 6.0 | 3.07 | 2.44 | 80.1 | 77.6 |
| 2 | 6.0 | 6.07 | 2.32 | 83.7 | 70.8 |
| 3 | 6.0 | 9.07 | 2.41 | 79.3 | 77.6 |
| 4 | 6.0 | 11.83 | 2.34 | 78.1 | 76.5 |
| 5 | 6.0 | 30.42 | 2.42 | 76.2 | 81.0 |
| 6 | 6.0 | 33.42 | 2.21 | 75.9 | 74.3 |
| 7 | 6.0 | 36.42 | 2.43 | 73.3 | 84.4 |
| 8 | 6.0 | 39.55 | 2.30 | 80.8 | 72.8 |
| 9 | 6.0 | 42.92 | 2.48 | 79.4 | 79.5 |
| 10 | 6.0 | 61.45 | 2.47 | 77.5 | 81.3 |
| 11 | 6.0 | 85.32 | 2.48 | 76.9 | 82.1 |
| 12 | 6.0 | 110.68 | 2.47 | 76.5 | 82.4 |
| 13 | 6.0 | 134.43 | 2.42 | 76.5 | 80.8 |
| 14 | 6.0 | 161.75 | 2.40 | 77.8 | 78.6 |
| 15 | 6.0 | 185.48 | 2.39 | 75.8 | 80.2 |
| 16 | 6.0 | 208.48 | 2.36 | 84.2 | 71.6 |
| 17 | 6.0 | 233.37 | 2.35 | 76.1 | 78.7 |
| 18 | 6.0 | 256.68 | 2.29 | 76.2 | 76.5 |
| 19 | 6.0 | 280.97 | 2.34 | 76.6 | 78.1 |
| 20 | 6.0 | 306.00 | 2.33 | 77.4 | 76.8 |
| 21 | 6.0 | 329.67 | 2.32 | 77.2 | 76.7 |
| 22 | 6.0 | 354.82 | 2.41 | 79.0 | 77.8 |
| 23 | 6.0 | 378.40 | 2.39 | 79.8 | 76.4 |
| 24 | 6.0 | 401.72 | 2.31 | 81.0 | 72.7 |
| 25 | 6.0 | 426.10 | 2.11 | 83.8 | 64.1 |
| 26 | 6.0 | 450.23 | 1.83 | 87.5 | 53.2 |
| 27 | 6.0 | 475.40 | 1.26 | 93.2 | 34.4 |
| 28 | 6.0 | 498.27 | 1.12 | 94.2 | 30.4 |
| 29 | 6.0 | 515.90 | 1.11 | 94.1 | 30.1 |

Figure 11:
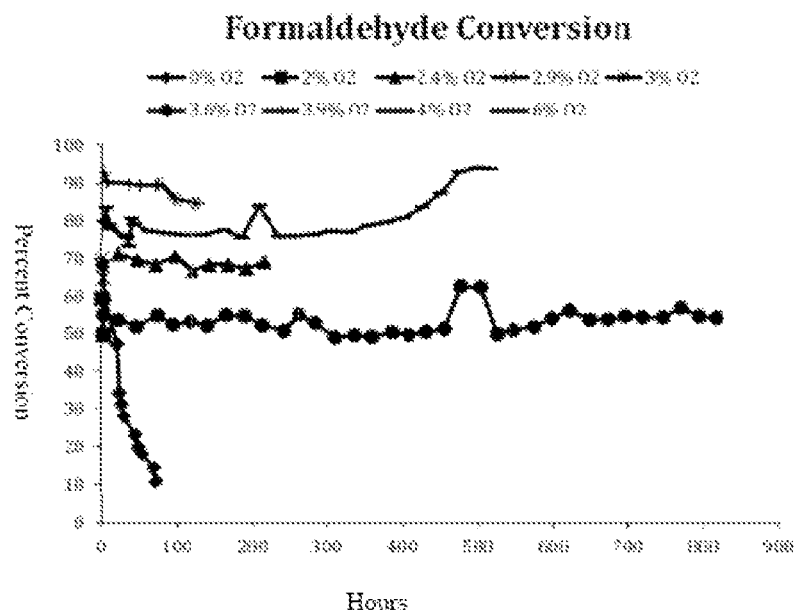
FIG. 11 is a graph showing the formaldehyde conversion for various oxygen amounts in the feed.
Figure 12:
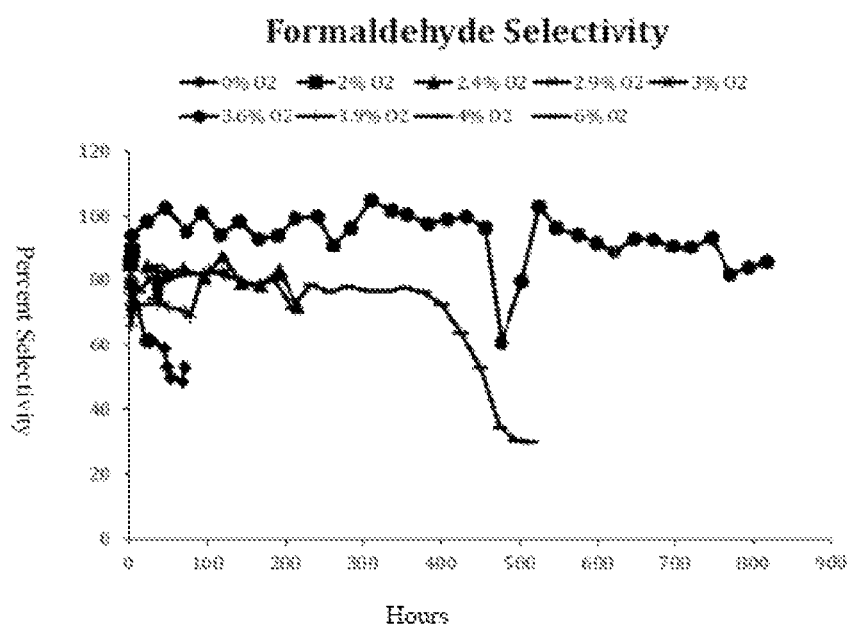
FIG. 12 is a graph showing the formaldehyde selectivity for various oxygen amounts in the feed.

As can be seen from Tables 27-34, oxygen can be introduced to the feed to improve the catalyst stability to synthesize acrylic acid over a V—Ti—P catalyst. As expected, the space time yield, conversion, and selectivity is better maintained when using an amount of oxygen in the feed as compared to Example 51. This set of experiments evaluated what the ideal range or amounts of oxygen would be to best improve the efficiency of the reaction. FIGS. 11 and 12 show a surprisingly narrow range of oxygen that is ideal for prolonging the reactivity of the catalyst while maintaining the space time yield, conversion, and selectivity. The data in Tables 27-34 also demonstrate that the formaldehyde conversion is frequently inversely related to the formaldehyde selectivity. The Samples from the 3.6%, 3.9%, 6.0% Examples graphed in Tables 11 and 12 generally show that when the conversion increases the selectivity decreases and when the conversion decreases the selectivity increases. An element of error is inherently present in analyzing the Samples of these different reactions since the formaldehyde is in constant equilibrium with other formaldehyde species as demonstrated by some of the conversion and selectivity values in Tables 11 and 12 being over 100%.

The invention has been described in detail with particular reference to preferred embodiments thereof, but it will be understood that variations and modifications can be effected within the spirit and scope of the invention.

What is claimed is:

1. A process for preparing a 2,3-unsaturated carboxylic acid comprising:
   contacting a formaldehyde source, a carboxylic acid, and a diluent gas with a condensation catalyst under vapor-phase condensation conditions to obtain the 2,3-unsaturated carboxylic acid;
   wherein the condensation catalyst comprises a mixed oxide of vanadium (V), titanium (Ti), and phosphorus (P);

wherein the diluent gas comprises from about 3 mol % to about 5 mol °le oxygen, based on the total moles of feed; and wherein the process has a selectivity of greater than about 40% and a conversion of greater than about 40%;

wherein the formaldehyde source is a methylene dicarboxylate having the general formula (I):

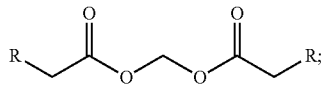
(I)

and wherein R is selected from the group consisting of a hydrogen, methyl, ethyl, propyl, iso-propyl, and an alkyl group having 1 to 8 carbons.

2. The process according to claim 1, wherein the diluent gas comprises from about 3 mol % to about 4 mol % oxygen, based on the total moles of feed.

3. The process according to claim 1, wherein the diluent gas comprises from about 3.5 mol % to about 4 mol % oxygen, based on the total moles of feed.

4. The process according to claim 1, wherein the process has a selectivity of greater than about 60% and a conversion of greater than about 50%.

5. The process according to claim 1, wherein the condensation catalyst has the formula $VTi_aP_bO_c$, wherein a is a number from 0.3 to 6.0, b is a number from 2.0 to 13.0, and c is the number of atoms required to satisfy the valences of the components other than oxygen.

6. The process according to claim 1, wherein the titanium component is the residue of a water-soluble, redox-active organo-titanium compound.

7. The process according to claim 6, wherein the organo-titanium compound comprises titanium(IV) bis(ammonium lactate) dihydroxide.

8. The process according to claim 1, wherein the condensation reaction has a total space feed velocity of from 50 to 400 moles of feed/(kg catalyst·hr).

9. The process according to claim 1, wherein the space time yield of the 2,3 unsaturated carboxylic acid is from about A to about 200 moles of 2,3 unsaturated carboxylic acid per kg catalyst per hour.

10. A process for preparing acrylic acid comprising:
contacting a formaldehyde source, acetic acid, and a diluent gas with a condensation catalyst under vapor-phase condensation conditions to obtain the acrylic acid;
wherein the condensation catalyst comprises a mixed oxide of vanadium (V), titanium (Ti), and phosphorus (P);
wherein the diluent gas comprises from about 3 mol % to about 5 mol % oxygen, based on the total moles of feed (liquids and diluent gas); and
wherein the process has a selectivity of greater than 40% and a conversion of greater than 40%
wherein the formaldehyde source comprises a methylene diacetate having the general formula (I):

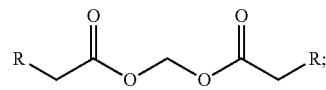
(I)

and wherein R is a hydrogen.

11. The process according to claim 10, wherein the diluent gas comprises from about 3.5 mol % to about 4 mol % oxygen, based on the total moles of feed (liquids and diluent gas).

12. The process according to claim 10, wherein the process has a selectivity of greater than 60% and a conversion of greater than 50%.

13. The process according to claim 10, wherein the titanium component is the residue of a water-soluble, redox-active organo-titanium compound and wherein the organo-titanium compound comprises titanium(IV) bis(ammonium lactate) dihydroxide.

14. A process for preparing methacrylic acid comprising:
contacting a formaldehyde source, propionic acid, and a diluent gas with a condensation catalyst under vapor-phase condensation conditions to obtain the methacrylic acid;
wherein the condensation catalyst comprises a mixed oxide of vanadium (V), titanium (Ti), and phosphorus (P);
wherein the diluent gas comprises from about 3 mol % to about 5 mol % oxygen, based on the total moles of feed (liquids and diluent gas); and
wherein the process has a selectivity of greater than 40% and a conversion of greater than 40%
wherein the formaldehyde source comprises a methylene dipropionate having the general formula (I):

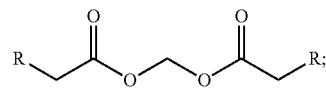
(I)

and wherein R is a methyl group.

15. The process according to claim 14, wherein the diluent gas comprises from about 3.5 mol % to about 4 mol % oxygen, based on the total moles of feed (liquids and diluent gas).

16. The process according to claim 14, wherein the process has a selectivity of greater than 60% and a conversion of greater than 50%.

17. The process according to claim 14, wherein the titanium component is the residue of a water-soluble, redox-active organo-titanium compound and wherein the organo-titanium compound comprises titanium(IV) bis(ammonium lactate) dihydroxide.

* * * * *

UNITED STATES PATENT AND TRADEMARK OFFICE
CERTIFICATE OF CORRECTION

PATENT NO.         : 9,573,119 B2                                     Page 1 of 1
APPLICATION NO.    : 14/859751
DATED              : February 21, 2017
INVENTOR(S)        : Deng et al.

It is certified that error appears in the above-identified patent and that said Letters Patent is hereby corrected as shown below:

In the Claims

Column 61, Line 2, Claim 1: "about 5 mol ° le oxygen," should read -- about 5 mol % oxygen, --

Column 61, Line 44, Claim 9: "about A to about 200 moles," should read -- about .1 to about 200 moles --

Signed and Sealed this
Sixteenth Day of May, 2017

Michelle K. Lee
*Director of the United States Patent and Trademark Office*